United States Patent
Fung et al.

(10) Patent No.: US 9,486,281 B2
(45) Date of Patent: Nov. 8, 2016

(54) METHODS AND DEVICES FOR ACCESSING AND DELIVERING DEVICES TO A HEART

(71) Applicant: SentreHEART, Inc., Redwood City, CA (US)

(72) Inventors: Gregory W. Fung, Redwood Shores, CA (US); Russell A. Seiber, Redwood City, CA (US); Robert Strasser, Mountain View, CA (US); Ryan Douglas Helmuth, Saratoga, CA (US)

(73) Assignee: SENTREHEART, INC., Redwood City, CA (US)

( * ) Notice: Subject to any disclaimer, the term of this patent is extended or adjusted under 35 U.S.C. 154(b) by 6 days.

(21) Appl. No.: 14/309,835

(22) Filed: Jun. 19, 2014

(65) Prior Publication Data

US 2014/0303721 A1 Oct. 9, 2014

Related U.S. Application Data

(63) Continuation of application No. 13/086,390, filed on Apr. 13, 2011, now Pat. No. 8,795,310.

(60) Provisional application No. 61/323,816, filed on Apr. 13, 2010, provisional application No. 61/323,801, filed on Apr. 13, 2010, provisional application No. 61/323,796, filed on Apr. 13, 2010.

(51) Int. Cl.
*A61F 2/24* (2006.01)
*A61B 18/14* (2006.01)
(Continued)

(52) U.S. Cl.
CPC ....... *A61B 18/1492* (2013.01); *A61B 18/1815* (2013.01); *A61B 18/24* (2013.01);
(Continued)

(58) Field of Classification Search
CPC .......... A61B 2017/00243; A61B 2017/00247; A61F 2/24; A61F 2/2427; A61F 2/243; A61F 2/2433; A61F 2/2436; A61F 2/2442; A61F 2/2457; A61F 2/2466
See application file for complete search history.

(56) References Cited

U.S. PATENT DOCUMENTS 3,496,932 A 2/1970 Prisk et al.
3,677,597 A 7/1972 Stipek
(Continued)

FOREIGN PATENT DOCUMENTS

CN 2624615 Y 7/2004
EP 0 598 219 A2 5/1994
(Continued)

OTHER PUBLICATIONS

AFIBFACTS.COM (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.
(Continued)

*Primary Examiner* — Ryan J Severson
(74) *Attorney, Agent, or Firm* — Cooley LLP

(57) ABSTRACT

Described here are devices and systems for accessing and delivering devices to a heart. The left atrial appendage may be used as an access port to allow pericardial access to internal structures of the heart. Systems that may be used to provide access to the heart via the left atrial appendage may comprise a first access element with a first alignment member, a second access element with a second alignment member, a piercing element, and an exchange element. A piercing element may be advanced to pierce the wall of the left atrial appendage to form an access site therethrough. Optionally, an exchange element may be advanced to initiate a track between the inside and outside of the left atrial appendage, which may be used for device delivery. Some systems may further comprise a left atrial appendage stabilization device.

20 Claims, 38 Drawing Sheets

(51) Int. Cl.
*A61B 18/24* (2006.01)
*A61N 7/02* (2006.01)
*A61B 18/18* (2006.01)
*A61B 17/00* (2006.01)
*A61B 18/02* (2006.01)
*A61B 18/00* (2006.01)
*A61N 7/00* (2006.01)

(52) U.S. Cl.
CPC .............. *A61F 2/24* (2013.01); *A61F 2/2427* (2013.01); *A61F 2/2442* (2013.01); *A61N 7/022* (2013.01); *A61B 18/02* (2013.01); *A61B 2017/00243* (2013.01); *A61B 2018/00279* (2013.01); *A61B 2018/1407* (2013.01); *A61B 2018/1861* (2013.01); *A61N 7/00* (2013.01)

(56) References Cited

U.S. PATENT DOCUMENTS

| | | |
|---|---|---|
| 3,802,074 A | 4/1974 | Hoppe |
| 3,841,685 A | 10/1974 | Kolodziej |
| 3,999,555 A | 12/1976 | Person |
| 4,018,229 A | 4/1977 | Komiya |
| 4,030,509 A | 6/1977 | Heilman et al. |
| 4,078,305 A | 3/1978 | Akiyama |
| 4,181,123 A | 1/1980 | Crosby |
| 4,249,536 A | 2/1981 | Vega |
| 4,257,278 A | 3/1981 | Papadofrangakis et al. |
| 4,319,562 A | 3/1982 | Crosby |
| 4,596,530 A | 6/1986 | McGlinn |
| 4,662,377 A | 5/1987 | Heilman et al. |
| 4,765,341 A | 8/1988 | Mower et al. |
| 4,817,608 A | 4/1989 | Shapland et al. |
| 4,901,405 A | 2/1990 | Grover et al. |
| 4,944,753 A | 7/1990 | Burgess et al. |
| 4,991,578 A | 2/1991 | Cohen |
| 4,991,603 A | 2/1991 | Cohen et al. |
| 4,998,975 A | 3/1991 | Cohen et al. |
| 5,033,477 A | 7/1991 | Chin et al. |
| 5,108,406 A | 4/1992 | Lee |
| 5,163,942 A | 11/1992 | Rydell |
| 5,163,946 A | 11/1992 | Li |
| 5,176,691 A | 1/1993 | Pierce |
| 5,181,123 A | 1/1993 | Swank |
| 5,226,535 A | 7/1993 | Rosdhy et al. |
| 5,226,908 A | 7/1993 | Yoon |
| 5,242,459 A | 9/1993 | Buelna |
| 5,243,977 A | 9/1993 | Trabucco et al. |
| 5,269,326 A | 12/1993 | Verrier |
| 5,281,238 A | 1/1994 | Chin et al. |
| 5,300,078 A | 4/1994 | Buelna |
| 5,306,234 A | 4/1994 | Johnson |
| 5,318,578 A | 6/1994 | Hasson |
| 5,336,229 A | 8/1994 | Noda |
| 5,336,252 A | 8/1994 | Cohen |
| 5,385,156 A | 1/1995 | Oliva |
| 5,387,219 A | 2/1995 | Rappe |
| 5,403,331 A | 4/1995 | Chesterfield et al. |
| 5,405,351 A | 4/1995 | Kinet et al. |
| 5,417,684 A | 5/1995 | Jackson et al. |
| 5,423,821 A | 6/1995 | Pasque |
| 5,423,830 A | 6/1995 | Schneebaum et al. |
| 5,433,457 A | 7/1995 | Wright |
| 5,433,730 A | 7/1995 | Alt |
| 5,443,481 A | 8/1995 | Lee |
| 5,449,637 A | 9/1995 | Saito et al. |
| 5,458,597 A | 10/1995 | Edwards et al. |
| 5,494,240 A | 2/1996 | Waugh |
| 5,498,228 A | 3/1996 | Royalty et al. |
| 5,540,711 A | 7/1996 | Kieturakis et al. |
| 5,571,161 A | 11/1996 | Starksen |
| 5,591,177 A | 1/1997 | Lehrer |
| 5,609,597 A | 3/1997 | Lehrer |
| 5,624,430 A | 4/1997 | Eton et al. |
| 5,624,453 A | 4/1997 | Ahmed |
| 5,634,895 A | 6/1997 | Igo et al. |
| 5,676,162 A | 10/1997 | Larson, Jr. et al. |
| 5,676,651 A | 10/1997 | Larson, Jr. et al. |
| 5,678,547 A | 10/1997 | Faupel et al. |
| 5,681,278 A | 10/1997 | Igo et al. |
| 5,682,906 A | 11/1997 | Sterman et al. |
| 5,683,348 A | 11/1997 | Diener |
| 5,683,364 A | 11/1997 | Zadini et al. |
| 5,683,445 A | 11/1997 | Swoyer |
| 5,693,059 A | 12/1997 | Yoon |
| 5,693,091 A | 12/1997 | Larson, Jr. et al. |
| 5,699,748 A | 12/1997 | Linskey, Jr. et al. |
| 5,702,430 A | 12/1997 | Larson, Jr. et al. |
| 5,707,336 A | 1/1998 | Rubin |
| 5,716,367 A | 2/1998 | Koike et al. |
| 5,716,392 A | 2/1998 | Bourgeois et al. |
| 5,727,569 A | 3/1998 | Benetti et al. |
| 5,728,151 A | 3/1998 | Garrison et al. |
| 5,735,877 A | 4/1998 | Pagedas |
| 5,741,281 A | 4/1998 | Martin |
| 5,752,526 A | 5/1998 | Cosgrove |
| 5,766,151 A | 6/1998 | Valley et al. |
| 5,766,216 A | 6/1998 | Gangal et al. |
| 5,766,217 A | 6/1998 | Christy |
| 5,769,863 A | 6/1998 | Garrison |
| 5,779,727 A | 7/1998 | Orejola |
| 5,792,151 A | 8/1998 | Heck et al. |
| 5,797,870 A | 8/1998 | March et al. |
| 5,797,929 A | 8/1998 | Andreas et al. |
| 5,797,946 A | 8/1998 | Chin |
| 5,799,661 A | 9/1998 | Boyd et al. |
| 5,810,845 A | 9/1998 | Yoon |
| 5,814,052 A | 9/1998 | Nakao et al. |
| 5,823,946 A | 10/1998 | Chin |
| 5,827,216 A | 10/1998 | Igo et al. |
| 5,840,059 A | 11/1998 | March et al. |
| 5,855,586 A | 1/1999 | Habara et al. |
| 5,865,791 A | 2/1999 | Whayne et al. |
| 5,871,531 A | 2/1999 | Struble |
| 5,873,876 A | 2/1999 | Christy |
| 5,879,375 A | 3/1999 | Larson, Jr. et al. |
| 5,882,299 A | 3/1999 | Rastegar et al. |
| 5,893,869 A | 4/1999 | Barnhart et al. |
| 5,895,298 A | 4/1999 | Faupel et al. |
| 5,897,586 A | 4/1999 | Molina |
| 5,900,433 A | 5/1999 | Igo et al. |
| 5,906,579 A | 5/1999 | Vander Salm et al. |
| 5,906,620 A | 5/1999 | Nakao et al. |
| 5,908,429 A | 6/1999 | Yoon |
| 5,908,435 A | 6/1999 | Samuels |
| 5,910,124 A | 6/1999 | Rubin |
| 5,910,129 A | 6/1999 | Koblish et al. |
| 5,921,994 A | 7/1999 | Andreas et al. |
| 5,924,424 A | 7/1999 | Stevens et al. |
| RE36,269 E | 8/1999 | Wright |
| 5,941,819 A | 8/1999 | Chin |
| 5,961,440 A | 10/1999 | Schweich, Jr. et al. |
| 5,964,699 A | 10/1999 | Rullo et al. |
| 5,968,010 A | 10/1999 | Waxman et al. |
| 5,972,013 A | 10/1999 | Schmidt |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,010,531 A | 1/2000 | Donlon et al. |
| 6,015,382 A | 1/2000 | Zwart et al. |
| 6,027,499 A | 2/2000 | Johnston et al. |
| 6,045,570 A | 4/2000 | Epstein et al. |
| 6,048,329 A | 4/2000 | Thompson et al. |
| 6,059,750 A | 5/2000 | Fogarty et al. |
| 6,067,942 A | 5/2000 | Fernandez |
| 6,071,281 A | 6/2000 | Burnside et al. |
| 6,081,738 A | 6/2000 | Hinohara et al. |
| 6,083,153 A | 7/2000 | Rullo et al. |
| 6,090,042 A | 7/2000 | Rullo et al. |
| 6,095,968 A | 8/2000 | Snyders |
| 6,110,170 A | 8/2000 | Taylor et al. |
| 6,120,431 A | 9/2000 | Magovern et al. |

(56) References Cited

U.S. PATENT DOCUMENTS

| | | |
|---|---|---|
| 6,132,438 A | 10/2000 | Fleischman et al. |
| 6,148,230 A | 11/2000 | KenKnight |
| 6,149,595 A | 11/2000 | Seitz et al. |
| 6,152,144 A | 11/2000 | Lesh et al. |
| 6,152,920 A | 11/2000 | Thompson et al. |
| 6,152,936 A | 11/2000 | Christy et al. |
| 6,155,968 A | 12/2000 | Wilk |
| 6,157,852 A | 12/2000 | Selmon et al. |
| 6,161,543 A | 12/2000 | Cox et al. |
| 6,162,195 A | 12/2000 | Igo et al. |
| 6,167,889 B1 | 1/2001 | Benetti |
| 6,199,556 B1 | 3/2001 | Benetti et al. |
| 6,200,303 B1 | 3/2001 | Verrior et al. |
| 6,206,004 B1 | 3/2001 | Schmidt et al. |
| 6,224,584 B1 | 5/2001 | March et al. |
| 6,231,518 B1 | 5/2001 | Grabek et al. |
| 6,237,605 B1 | 5/2001 | Vaska et al. |
| 6,241,667 B1 | 6/2001 | Vetter et al. |
| 6,258,021 B1 | 7/2001 | Wilk |
| 6,266,550 B1 | 7/2001 | Selmon et al. |
| 6,280,415 B1 | 8/2001 | Johnson |
| 6,283,127 B1 | 9/2001 | Sterman et al. |
| 6,290,674 B1 | 9/2001 | Roue et al. |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,346,074 B1 | 2/2002 | Roth |
| 6,379,366 B1 | 4/2002 | Fleischman et al. |
| 6,423,051 B1 | 7/2002 | Kaplan et al. |
| 6,474,340 B1 | 11/2002 | Vaska et al. |
| 6,485,407 B2 | 11/2002 | Alferness et al. |
| 6,488,689 B1 | 12/2002 | Kaplan et al. |
| 6,494,211 B1 | 12/2002 | Boyd et al. |
| 6,551,303 B1 | 4/2003 | Van Tassel et al. |
| 6,561,969 B2 | 5/2003 | Frazier et al. |
| 6,592,552 B1 | 7/2003 | Schmidt |
| 6,610,055 B1 | 8/2003 | Swanson et al. |
| 6,610,072 B1 | 8/2003 | Christy et al. |
| 6,613,062 B1 | 9/2003 | Leckrone et al. |
| 6,632,229 B1 | 10/2003 | Yamanouchi |
| 6,652,555 B1 | 11/2003 | VanTassel et al. |
| 6,656,175 B2 | 12/2003 | Francischelli et al. |
| 6,666,861 B1 | 12/2003 | Grabek |
| 6,692,491 B1 | 2/2004 | Phan |
| 6,733,509 B2 | 5/2004 | Nobles et al. |
| 6,736,774 B2 | 5/2004 | Benetti et al. |
| 6,755,338 B2 | 6/2004 | Hahnen et al. |
| 6,786,898 B2 | 9/2004 | Guenst |
| 6,789,509 B1 | 9/2004 | Motsinger |
| 6,830,174 B2 | 12/2004 | Hillstead et al. |
| 6,830,576 B2 | 12/2004 | Fleischman et al. |
| 6,840,246 B2 | 1/2005 | Downing |
| 6,985,776 B2 | 1/2006 | Kane et al. |
| 7,011,671 B2 | 3/2006 | Welch |
| 7,041,111 B2 | 5/2006 | Chu |
| 7,056,294 B2 | 6/2006 | Khairkhahan et al. |
| 7,063,682 B1 | 6/2006 | Whayne et al. |
| 7,063,693 B2 | 6/2006 | Guenst |
| 7,175,619 B2 | 2/2007 | Koblish et al. |
| 7,186,214 B2 | 3/2007 | Ness |
| 7,207,988 B2 | 4/2007 | Leckrone et al. |
| 7,226,440 B2 | 6/2007 | Gelfand et al. |
| 7,226,458 B2 | 6/2007 | Kaplan et al. |
| 7,264,587 B2 | 9/2007 | Chin |
| 7,294,115 B1 | 11/2007 | Wilk |
| 7,297,144 B2 | 11/2007 | Fleischman et al. |
| 7,309,328 B2 | 12/2007 | Kaplan et al. |
| 7,318,829 B2 | 1/2008 | Kaplan et al. |
| 7,326,221 B2 | 2/2008 | Sakamoto et al. |
| 7,331,979 B2 | 2/2008 | Khosravi et al. |
| 7,473,260 B2 | 1/2009 | Opolski et al. |
| 7,608,091 B2 | 10/2009 | Goldfarb et al. |
| 7,610,104 B2 | 10/2009 | Kaplan et al. |
| 7,618,425 B2 | 11/2009 | Yamamoto et al. |
| 7,681,579 B2 | 3/2010 | Schwartz |
| 7,722,641 B2 | 5/2010 | van der Burg et al. |
| 7,736,347 B2 | 6/2010 | Kaplan et al. |
| 7,828,810 B2 | 11/2010 | Liddicoat et al. |
| 7,846,168 B2 | 12/2010 | Liddicoat et al. |
| 7,905,900 B2 | 3/2011 | Palermo et al. |
| 7,918,865 B2 | 4/2011 | Liddicoat et al. |
| 7,967,808 B2 | 6/2011 | Fitzgerald et al. |
| 8,105,342 B2 | 1/2012 | Onuki et al. |
| 8,157,818 B2 | 4/2012 | Gartner et al. |
| 8,287,561 B2 | 10/2012 | Nunez et al. |
| 8,469,983 B2 | 6/2013 | Fung et al. |
| 8,500,768 B2 | 8/2013 | Cohen |
| 8,636,767 B2 | 1/2014 | McClain |
| 8,721,663 B2 | 5/2014 | Kaplan et al. |
| 8,771,297 B2 | 7/2014 | Miller et al. |
| 8,795,297 B2 | 8/2014 | Liddicoat et al. |
| 8,795,310 B2 | 8/2014 | Fung et al. |
| 8,814,778 B2 | 8/2014 | Kiser et al. |
| 8,974,473 B2 | 3/2015 | Kaplan et al. |
| 8,986,278 B2 | 3/2015 | Fung et al. |
| 8,986,325 B2 | 3/2015 | Miller et al. |
| 8,996,133 B2 | 3/2015 | Kaplan et al. |
| 9,198,664 B2 | 12/2015 | Fung et al. |
| 9,271,819 B2 | 3/2016 | Liddicoat et al. |
| 2001/0003795 A1 | 6/2001 | Suresh et al. |
| 2001/0025132 A1 | 9/2001 | Alferness et al. |
| 2002/0002329 A1 | 1/2002 | Avitall |
| 2002/0017306 A1 | 2/2002 | Cox et al. |
| 2002/0022860 A1 | 2/2002 | Borillo et al. |
| 2002/0045895 A1 | 4/2002 | Sliwa, Jr. et al. |
| 2002/0049457 A1 | 4/2002 | Kaplan et al. |
| 2002/0058925 A1 | 5/2002 | Kaplan et al. |
| 2002/0062136 A1 | 5/2002 | Hillstead et al. |
| 2002/0068970 A1 | 6/2002 | Cox et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111636 A1 | 8/2002 | Fleischman et al. |
| 2002/0111637 A1 | 8/2002 | Kaplan et al. |
| 2002/0123771 A1 | 9/2002 | Ideker et al. |
| 2002/0128639 A1 | 9/2002 | Pless et al. |
| 2003/0014049 A1 | 1/2003 | Koblish et al. |
| 2003/0024537 A1 | 2/2003 | Cox et al. |
| 2003/0045900 A1 | 3/2003 | Hahnen et al. |
| 2003/0069577 A1 | 4/2003 | Vaska et al. |
| 2003/0078465 A1 | 4/2003 | Pai et al. |
| 2003/0083542 A1 | 5/2003 | Alferness et al. |
| 2003/0083674 A1 | 5/2003 | Gibbens, III |
| 2003/0109863 A1 | 6/2003 | Francischelli et al. |
| 2003/0120264 A1 | 6/2003 | Lattouf |
| 2003/0120337 A1 | 6/2003 | Van Tassel et al. |
| 2003/0158464 A1 | 8/2003 | Bertolero |
| 2003/0181942 A1 | 9/2003 | Sutton et al. |
| 2003/0187460 A1 | 10/2003 | Chin et al. |
| 2003/0220667 A1 | 11/2003 | Van der Burg et al. |
| 2003/0236535 A1 | 12/2003 | Onuki et al. |
| 2004/0024414 A1 | 2/2004 | Downing |
| 2004/0030335 A1 | 2/2004 | Zenati et al. |
| 2004/0034347 A1 | 2/2004 | Hall et al. |
| 2004/0044361 A1 | 3/2004 | Frazier et al. |
| 2004/0049210 A1 | 3/2004 | VanTassel et al. |
| 2004/0059280 A1 | 3/2004 | Makower et al. |
| 2004/0059352 A1 | 3/2004 | Burbank et al. |
| 2004/0064138 A1 | 4/2004 | Grabek |
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 | 6/2004 | Chin |
| 2004/0116943 A1 | 6/2004 | Brandt et al. |
| 2004/0122467 A1 | 6/2004 | Van Tassel et al. |
| 2004/0162579 A1 | 8/2004 | Foerster |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |

(56) References Cited

U.S. PATENT DOCUMENTS

| | | |
|---|---|---|
| 2004/0260273 A1 | 12/2004 | Wan |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043745 A1 | 2/2005 | Alferness et al. |
| 2005/0085843 A1 | 4/2005 | Opolski et al. |
| 2005/0101984 A1 | 5/2005 | Chanduszko et al. |
| 2005/0107824 A1 | 5/2005 | Hillstead et al. |
| 2005/0113861 A1 | 5/2005 | Corcoran et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0165466 A1 | 7/2005 | Morris et al. |
| 2005/0187545 A1 | 8/2005 | Hooven et al. |
| 2005/0228422 A1 | 10/2005 | Machold et al. |
| 2005/0256532 A1 | 11/2005 | Nayak et al. |
| 2006/0004323 A1 | 1/2006 | Chang et al. |
| 2006/0004388 A1 | 1/2006 | Whayne et al. |
| 2006/0009715 A1 | 1/2006 | Khairkhahan et al. |
| 2006/0009756 A1 | 1/2006 | Francischelli et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0100545 A1 | 5/2006 | Ayala et al. |
| 2006/0200120 A1 | 9/2006 | DiCarlo et al. |
| 2006/0200169 A1 | 9/2006 | Sniffin |
| 2006/0212045 A1 | 9/2006 | Schilling et al. |
| 2006/0247672 A1 | 11/2006 | Vidlund et al. |
| 2006/0253128 A1 | 11/2006 | Sekine et al. |
| 2007/0016228 A1 | 1/2007 | Salas |
| 2007/0027456 A1 | 2/2007 | Gartner et al. |
| 2007/0038229 A1 | 2/2007 | De la Torre et al. |
| 2007/0043344 A1 | 2/2007 | McAuley |
| 2007/0060951 A1 | 3/2007 | Shannon |
| 2007/0083082 A1 | 4/2007 | Kiser et al. |
| 2007/0083194 A1 | 4/2007 | Kunis et al. |
| 2007/0083225 A1 | 4/2007 | Kiser et al. |
| 2007/0083230 A1 | 4/2007 | Javois |
| 2007/0083232 A1 | 4/2007 | Lee |
| 2007/0088369 A1 | 4/2007 | Shaw et al. |
| 2007/0100405 A1 | 5/2007 | Thompson et al. |
| 2007/0135822 A1 | 6/2007 | Onuki et al. |
| 2007/0149988 A1 | 6/2007 | Michler et al. |
| 2007/0179345 A1 | 8/2007 | Santilli |
| 2007/0203554 A1 | 8/2007 | Kaplan et al. |
| 2007/0219546 A1 | 9/2007 | Mody et al. |
| 2007/0249991 A1 | 10/2007 | Whayne et al. |
| 2007/0260278 A1 | 11/2007 | Wheeler et al. |
| 2007/0270637 A1 | 11/2007 | Takemoto et al. |
| 2007/0270891 A1 | 11/2007 | McGuckin, Jr. |
| 2008/0009843 A1 | 1/2008 | de la Torre |
| 2008/0015571 A1 | 1/2008 | Rubinsky et al. |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0058635 A1 | 3/2008 | Halperin et al. |
| 2008/0097489 A1 | 4/2008 | Goldfarb et al. |
| 2008/0125795 A1 | 5/2008 | Kaplan et al. |
| 2008/0177381 A1 | 7/2008 | Navia et al. |
| 2008/0214889 A1 | 9/2008 | Saadat et al. |
| 2008/0221593 A1 | 9/2008 | Liddicoat et al. |
| 2008/0228265 A1 | 9/2008 | Spence et al. |
| 2008/0269782 A1 | 10/2008 | Stefanchik et al. |
| 2008/0294174 A1 | 11/2008 | Bardsley et al. |
| 2008/0294175 A1 | 11/2008 | Bardsley et al. |
| 2008/0312664 A1 | 12/2008 | Bardsley et al. |
| 2009/0043317 A1 | 2/2009 | Cavanaugh et al. |
| 2009/0093809 A1 | 4/2009 | Anderson et al. |
| 2009/0143791 A1 | 6/2009 | Miller et al. |
| 2009/0157118 A1 | 6/2009 | Miller et al. |
| 2009/0182326 A1 | 7/2009 | Zenati et al. |
| 2010/0069925 A1 | 3/2010 | Friedman et al. |
| 2010/0174296 A1 | 7/2010 | Vakharia et al. |
| 2011/0087247 A1 | 4/2011 | Fung et al. |
| 2011/0144660 A1 | 6/2011 | Liddicoat et al. |
| 2011/0276075 A1 | 11/2011 | Fung et al. |
| 2011/0282250 A1 | 11/2011 | Fung et al. |
| 2012/0022558 A1 | 1/2012 | Friedman et al. |
| 2012/0095434 A1 | 4/2012 | Fung et al. |
| 2012/0330351 A1 | 12/2012 | Friedman et al. |
| 2013/0144311 A1 | 6/2013 | Fung et al. |
| 2013/0218156 A1 | 8/2013 | Kassab et al. |
| 2013/0296880 A1 | 11/2013 | Kelley et al. |
| 2014/0018831 A1 | 1/2014 | Kassab et al. |
| 2014/0171733 A1 | 6/2014 | Sternik |
| 2014/0364901 A1 | 12/2014 | Kiser et al. |
| 2014/0371741 A1 | 12/2014 | Longoria et al. |
| 2015/0018853 A1 | 1/2015 | Friedman et al. |
| 2015/0025312 A1 | 1/2015 | de Canniere |
| 2015/0157328 A1 | 6/2015 | Miller et al. |
| 2015/0173765 A1 | 6/2015 | Miller et al. |
| 2015/0182225 A1 | 7/2015 | Morejohn et al. |
| 2015/0190135 A1 | 7/2015 | Ibrahim et al. |
| 2015/0250482 A1 | 9/2015 | Slaughter et al. |
| 2016/0008061 A1 | 1/2016 | Fung et al. |
| 2016/0120549 A1 | 5/2016 | Fung et al. |

FOREIGN PATENT DOCUMENTS

| | | |
|---|---|---|
| EP | 1 010 397 A1 | 6/2000 |
| GB | 1 506 142 A | 4/1978 |
| JP | 7-296645 A2 | 11/1995 |
| JP | 7-299073 A | 11/1995 |
| JP | 11-507262 A | 6/1999 |
| JP | 2001-120560 A | 5/2001 |
| JP | 2002-540834 A | 12/2002 |
| JP | 2002-540901 A | 12/2002 |
| JP | 2003-225241 A | 8/2003 |
| JP | 2004-601 A | 1/2004 |
| JP | 2005-110860 A | 4/2005 |
| JP | 2005-296645 A | 10/2005 |
| JP | 2005-531360 A | 10/2005 |
| JP | 2007-504886 A | 3/2007 |
| JP | 2007-534355 A | 11/2007 |
| JP | 2008-534085 A | 8/2008 |
| WO | WO-94/01045 A1 | 1/1994 |
| WO | WO-94/04079 A1 | 3/1994 |
| WO | WO-94/08514 A1 | 4/1994 |
| WO | WO-96/40356 A1 | 12/1996 |
| WO | WO-97/11644 A1 | 4/1997 |
| WO | WO-97/43957 A1 | 11/1997 |
| WO | WO-00/59383 A1 | 10/2000 |
| WO | WO-00/61202 A1 | 10/2000 |
| WO | WO-03/028558 A2 | 4/2003 |
| WO | WO-2004/002327 A1 | 1/2004 |
| WO | WO-2004/066828 A2 | 8/2004 |
| WO | WO-2005/034767 A1 | 4/2005 |
| WO | WO-2005/034802 A2 | 4/2005 |
| WO | WO-2006/096805 A1 | 9/2006 |
| WO | WO-2006/110734 A2 | 10/2006 |
| WO | WO-2006/115689 A1 | 11/2006 |
| WO | WO-2007/056502 A1 | 5/2007 |
| WO | WO-2008/017080 A2 | 2/2008 |
| WO | WO-2008/036408 A2 | 3/2008 |
| WO | WO-2008/091612 A2 | 7/2008 |
| WO | WO-2008/121278 A2 | 10/2008 |
| WO | WO-2008/150346 A1 | 12/2008 |
| WO | WO-2009/039191 A2 | 3/2009 |
| WO | WO-2009/045265 A1 | 4/2009 |
| WO | WO-2009/094237 A1 | 7/2009 |
| WO | WO-2010/006061 A2 | 1/2010 |
| WO | WO-2010/048141 A2 | 4/2010 |
| WO | WO-2010/115030 A1 | 10/2010 |
| WO | WO-2011/129893 A1 | 10/2011 |

OTHER PUBLICATIONS

Al-Saady, N.M. et al. (1999). "Left Atrial Appendage: Structure, Function, and Role in Thromboembolism," *Heart* 82:547-554.

Albers, G.W. (Jul. 11, 1994). "Atrial Fibrillation and Stroke: Three New Studies, Three Remaining Questions," *Arch Intern Med* 154:1443-1448.

(56) References Cited

OTHER PUBLICATIONS

Alonso, M. et al. (Mar. 4, 2003). "Complications With Femoral Access in Cardiac Catheterization. Impact of Previous Systematic Femoral Angiography and Hemostasis With VasoSeal-Es®Collagen Plug," *Rev. Esp. Cardiol.* 56(6):569-577.
Aronow, W.S. et al. (Apr. 2009). "Atrial Fibrillation: the New Epidemic of the Age-ing World," *Journal of Atrial Fibrillation* 1(6):337-361.
Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.
Bath, P.M.W. et al. (2005). "Current Status of Stroke Prevention in Patients with Atrial Fibrillation," *European Heart Journal Supplements* 7(Supplement C):C12-C18.
Benjamin, B.A. et al. (1994). "Effect of Bilateral Atrial Appendectomy on Postprandial Sodium Excretion in Conscious Monkeys," *Society for Experimental Biology and Medicine* 206: 1 page.
Beygui, F. et al. (2005, e-pub. Oct. 21, 2005). "Multimodality Imaging of Percutaneous Closure of the Left Atrial Appendage," *Clinical Vignette*, 1 page.
Bisleri, G. et al. (Jun. 3, 2005). "Innovative Monolateral Approach for Closed-Chest Atrial Fibrillation Surgery," *The Annals of Thoracic Surgery* 80:e22-e25.
Björk, V.O. et al. (Aug. 1961). "Sequelae of Left Ventricular Puncture with Angiocardiography," *Circulation* 24:204-212.
Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.
Blackshear, J.L. et al. (Oct. 1, 2003). "Thorascopic Extracardiac Obliteration of the Left Atrial Appendage for Stroke Risk Reduction in Atrial Fibrillation," *J. Am. Coll. Cardiol.* 42(7):1249-1252.
Bonanomi, G. et al. (Jan. 1, 2003). "Left Atrial Appendectomy and Maze," *Journal of the American College of Cardiology* 41(1):169-171.
Bonow, R.O. et al. (1998). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Circulation* 98:1949-1984.
Botham, R.J. et al. (May 1959). "Pericardial Tamponade Following Percutaneous Left Ventricular Puncture," *Circulation* 19:741-744.
Brock, R. et al. (1956). "Percutaneous Left Ventricular Puncture in the Assessment of Aortic Stenosis," *Thorax* 11:163-171.
Burke, R.P. et al. (1992). "Improved Surgical Approach to Left Atrial Appendage Aneurysm," *Journal of Cardiac Surgery* 7(2):104-107.
Canaccord Adams. (Aug. 11, 2008). "A-Fib: Near A Tipping Point," 167 pages.
Chung, M.K. (Jul. 2003). "Current Clinical Issues in Atrial Fibrillation," *Cleveland Clinic Journal of Medicine* 70(Supp. 3):S6-S11.
Coffin, L.H. (Jun. 1985). "Use of the Surgical Stapler to Obliterate the Left Atrial Appendage," *Surgery, Gynecology & Obstetric* 160:565-566.
Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.
Costa, R. et al. (2006). "Bi-Atrial Subxiphoid Epicardial Pacemaker in Superior Vena Cava Syndrome," *Arq. Bras. Cardiol.* 87:e45-e47.
Cox, J.L. et al. (Apr. 1991). "The Surgical Treatment of Atrial Fibrillation: IV. Surgical Technique," *J. Thorac. Cardiovasc. Surg.* 101(4):584-592.
Cox, J.L. et al. (Aug. 1995). "Modification of the Maze Procedure for Atrial Flutter and Atrial Fibrillation I. Rationale and Surgical Results," *J. Thorac. Cardiovasc. Surg.* 110(2):473-484.
Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.
Cox, J.L. et al. (Nov. 1999). "Impact of the Maze Procedure on the Stroke Rate in Patients with Atrial Fibrillation," *J. Thorac. Cardiovasc. Surg.* 118:833-840.
Cox, J.L. et al. (2004). "The Role of Surgical Intervention in the Management of Atrial Fibrillation," *Texas Heart Institute Journal* 31(3):257-265.
Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.
D'Avila, A. et al. (Apr. 2003). "Pericardial Anatomy for the Interventional Electrophysiologist," *Journal of Cardiovascular Electrophysiology* 14(4):422-430.
D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.
Demaria, A.N. et al. (Dec. 17, 2003). "Highlights of the Year JACC 2003," *Journal of the American College of Cardiology* 42(12):2156-2166.
Deneu, S. et al. (Jul. 11, 1999). "Catheter Entrapment by Atrial Suture During Minimally Invasive Port-access Cardiac Surgery," *Canadian Journal of Anasthesia* 46(10):983-986.
Deponti, R. et al. (Mar. 7, 2006). "Trans-Septal Catheterization in the Electrophysiology Laboratory: Data From a Multicenter Survey Spanning 12 Years," *Journal of the American College of Cardiology* 47(5):1037-1042.
Donal, E. et al. (Sep. 2005). "The Left Atrial Appendage, a Small, Blind-Ended Structure: A Review of Its Echocardiographic Evaluation and Its Clinical Role," *Chest* 128(3):1853-1862.
Donnino, R. et al. (2007). "Left Atrial Appendage Thrombus Outside of a 'Successful' Ligation," *European Journal of Echocardiography* pp. 1-2.
Dullum, M.K.C. et al. (1999). "Xyphoid MIDCAB: Report of the Technique and Experience with a Less Invasive MIDCAB Procedure," *Heart Surgery Forum* 2(1):77-81.
Feinberg, W.M. et al. (Mar. 13, 1995). "Prevalence, Age Distribution, and Gender of Patients With Atrial Fibrillation," *Arch Intern Med* 155:469-473.
Fieguth, H.G. et al. (1997). "Inhibition of Atrial Fibrillation by Pulmonary Vein Isolation and Auricular Resection—Experimental Study in a Sheep Model," *European Journal of Cardio-Thoracic Surgery* 11:714-721.
Final Office Action mailed on Jun. 22, 2009, for U.S. Appl. No. 10/963,371, filed on Oct. 11, 2004, 11 pages.
Final Office Action mailed on Apr. 14, 2010, for U.S. Appl. No. 11/600,671, filed on Nov. 15, 2006, 7 pages.
Final Office Action mailed on Jul. 21, 2010, for U.S. Appl. No. 11/400,714, filed on Apr. 7, 2006, 10 pages.
Final Office Action mailed on Apr. 26, 2011, for U.S. Appl. No. 12/037,802, filed on Feb. 26, 2008, 9 pages.
Final Office Action mailed on Sep. 20, 2011, for U.S. Appl. No. 12/212,511, filed on Sep. 17, 2008, 8 pages.
Final Office Action mailed on Oct. 28, 2011, for U.S. Appl. No. 12/055,213, filed on Mar. 25, 2008, 15 pages.
Final Office Action mailed on May 4, 2012, for U.S. Appl. No. 12/363,359, filed on Jan. 30, 2009, 10 pages.
Final Office Action mailed on May 16, 2012, for U.S. Appl. No. 12/363,381, filed on Jan. 30, 2009, 8 pages.
Final Office Action mailed on Jul. 11, 2012, for U.S. Appl. No. 13/033,532, filed on Feb. 23, 2011, 8 pages.
Final Office Action mailed on Jul. 24, 2012, for U.S. Appl. No. 12/212,511, filed on Sep. 17, 2008, 6 pages.
Final Office Action mailed on Oct. 18, 2012, for U.S. Appl. No. 12/124,023, filed on May 20, 2008, 15 pages.
Final Office Action mailed on Nov. 8, 2013, for U.S. Appl. No. 12/037,802, filed on Feb. 26, 2008, 15 pages.
Final Office Action mailed on Jan. 13, 2014, for U.S. Appl. No. 12/752,873, filed on Apr. 1, 2010, 10 pages.
Final Office Action mailed on Oct. 22, 2013 for U.S. Appl. No. 13/086,390, filed Apr. 13, 2011, 6 pages.

(56) References Cited

OTHER PUBLICATIONS

Fisher, D.C. et al. (Dec. 1998). "Large Gradient Across a Partially Ligated Left Atrial Appendage," *Journal of the American Society of Echocardiography* 11(12):1163-1165.
Friberg, L. et al. (2006). "Stroke Prophylaxis in Atrial Fibrillation: Who Gets it and Who Does Not?" *European Heart Journal* 27:1954-1964.
Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.
Fuster, V. et al. (Oct. 2001). "ACC/AHA/ESC Guidelines for the Management of Patients with Atrial Fibrillation," *European Heart Journal* 22(20):1852-1923.
Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.
Gardiner, G.A. Jr. et al. (Apr. 1986). "Complications of Transluminal Angioplasty," *Radiology* 159(1):201-208.
Gillinov, A.M. (Feb. 2007). "Advances in Surgical Treatment of Atrial Fibrillation," *Stroke* 38(part 2):618-623.
Gilman, R.A. et al. (Apr. 1963). "Direct Left Ventricular Puncture," *California Medicine* 98(4):200-203.
Goodwin, W.E. et al. (Nov. 1950). "Translumbar Aortic Puncture and Retrograde Catheterization of the Aorta in Aortography and Renal Arteriography," *Annals of Surgery* 132(5):944-958.
Gottlieb, L.K. et al. (Sep. 12, 1994). "Anticoagulation in Atrial Fibrillation," *Arch. Intern. Med.* 154:1945-1953.
Graffigna, A. et al. (1993). "Surgical Treatment of Wolff-Parkinson-White Syndrome: Epicardial Approach Without the Use of Cardiopulmonary Bypass," *J. Card. Surg.* 8:108-116.
Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.
Halperin, J.L. et al. (Aug. 1988). "Atrial Fibrillation and Stroke: New Ideas, Persisting Dilemmas," *Journal of the American Heart Association* 19(8):937-941.
Halperin, J.L. et al. (Oct. 1, 2003). "Obliteration of the Left Atrial Appendage for Prevention of Thromboembolism," *Journal of the American College of Cardiology* 42(7):1259-1261.
Hammill, S.C. (May 2006). "Epicardial Ablation: Reducing the Risks," *J. Cardiovasc. Electrophysiol.* 17:550-552.
Hara, H. et al. (Jan. 2008). "Percutaneous Left Atrial Appendage Obliteration," *JACC: Cardiovascular Imagin* 1(1):92-93.
Hart, R.G. et al. (Nov. 2, 1999). "Atrial Fibrillation and Thromboembolism: A Decade of Progress in Stroke Prevention," *Annals of Internal Medicine* 131(9):688-695.
Hart, R.G. et al. (Mar. 2001). "Atrial Fibrillation and Stroke: Concepts and Controversies," *Stroke* 32:803-808.
Hart, R.G. (Sep. 11, 2003). "Atrial Fibrillation and Stroke Prevention," *The New England Journal of Medicine* 349(11):1015-1016.
Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," *presented at* the Canadian Cardiovascular Congress 2003, Toronto, Canada, Abstract No. 666, 2 pages.
Healey, J.S. et al. (Aug. 2005). "Left Atrial Appendage Occlusion Study (LAAOS): Results of a Randomized Controlled Pilot Study of Left Atrial Appendage Occlusion During Coronary Bypass Surgery in Patients At Risk for Stroke," *American Heart Journal* 150(2):288-293.
Hein, R. et al. (2005). "Patent Foramen Ovale and Left Atrial Appendage: New Devices and Methods for Closure," *Pediatric Cardiology* 26(3):234-240.
Heist, E.K. et al. (Nov. 2006). "Analysis of the Left Atrial Appendage by Magnetic Resonance Angiography in Patients with Atrial Fibrillation," *Heart Rhythm* 3(11):1313-1318.

Ho, I. et al. (Apr. 24, 2007). "Percutaneous Epicardial Mapping Ablation of a Posteroseptal Accessory Pathway," *Circulation* 115:e418-e421.
Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.
Hoit, B.D. et al. (Jan. 1993). "Altered Left Atrial Compliance After Atrial Appendectomy. Influence on Left Atrial and Ventricular Filling," *Circulation Research* 72(1):167-175.
Inoue, Y. et al. (Jul.-Aug. 1997). "Video Assisted Thoracoscopic and Cardioscopic Radiofrequency Maze Ablation," *Asaio Journal* 43(4):334-337 (Abstract Only).
International Search Report mailed on Oct. 3, 2011, for PCT Patent Application No. PCT/US2011/00677, filed on Apr. 13, 2011, 5 pages.
Jaïs, P. et al. (2003). "Radiofrequency Ablation for Atrial Fibrillation," *European Society of Cardiology* 5(Supplement H):H34-H39.
Johnson, W.D. et al. (2000). "The Left Atrial Appendage: Our Most Lethal Human Attachment! Surgical Implications," *Euro. J. Cardiothoracic. Surg.* 17:718-722.
Jongbloed, M.R.M. et al. (2005). "Clinical Applications of Intracardiac Echocardiography in Interventional Procedures," *Heart* 91:981-990.
Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.
Kanderian, A.S. et al. (2008). "Success of Surgical Left Atrial Appendage Closure: Assessment by Transesophageal Echocardiography," *Journal of the American College of Cardiology* 52(11):924-929.
Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.
Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.
Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.
Kerut, E.K. et al. (Jul. 2008). "Anatomy of the Left Atrial Appendage," *Echocardiography* 25(6):669-673.
Khargi, K. et al. (2005). "Surgical Treatment of Atrial Fibrillation: A Systematic Review," *European Journal of Cardiothoracic Surgery* 27:258-265.
Kim, K.B. et al. (Jan. 1998). "Effect of the Cox Maze Procedure on the Secretion of Atrial Natriuretic Peptide," *J. Thorac. Cardiovasc. Surg.* 115(1):139-146; discussion 146-147.
Kistler, P.M. et al. (May 2007). "The Left Atrial Appendage: Not Just an Innocent Bystander," *J. Cardiovasc Electrophysiol* 18(5):465-466.
Klein, H. et al. (Apr. 1990). "The Implantable Automatic Cardioverter-Defibrillator," *Herz* 15(2):111-125, Abstract Only.
Kolb, C. et al. (Feb. 2004). "Incidence of Antitachycardia Therapy Suspension Due to Magnet Reversion in Implantable Cardioverter Defibrillators," *Pace* 27:221-223.
Krikorian, J.G. et al. (Nov. 1978). "Pericardiocentesis," *Am. J. Med.* 65(5):808-814.
Krum, D. et al. (2004). "Visualization of Remnants of the left Atrial Appendage Following Epicardial Surgical Removal," *Heart Rhythm* 1:249.
Lacomis, J.M. et al. (Oct. 2003). "Multi-Detector Row Ct of the Left Atrium and Pulmonary Veins before Radio-frequency Catheter Ablation for Atrial Fibrillation," *Radio Graphics* 23:S35-S48.
Lacomis, J.M. et al. (2007, e-pub. Oct. 17, 2007). "Dynamic Multidimensional Imaging of the Human Left Atrial Appendage," *Europace* 9:1134-1140.
Lee, R. et al. (1999). "The Closed Heart MAZE: A Nonbypass Surgical Technique," *The Annals of Thoracic Surgery* 67:1696-1702.

(56) References Cited

OTHER PUBLICATIONS

Levinson, M.L. et al. (1998). "Minimally Invasive Atrial Septal Defect Closure Using the Subxyphoid Approach," *Heart Surg. Forum* 1(1):49-53 (Abstract Only).
Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.
Li, H. (2007). "Magnet Decoration, Beautiful But Potentially Dangerous for Patients with Implantable Pacemakers or Defibrillators," *Heart Rhythm* 4(1):5-6.
Lindsay, B.D. (1996). "Obliteration of the Left Atrial Appendage: A Concept Worth Testing," *The Annals of Thoracic Surgery* 61:515-516.
Lip, G.Y.H. et al. (Jun. 2001). "Thromboprophylaxis for Atrial Flutter," *European Heart Journal* 22(12):984-987.
Lustgarten, D.L. et al. (May/Jun. 1999). "Cryothermal Ablation: Mechanism of Tissue Injury and Current Experience in the Treatment of Tachyarrhythmias," *Progress in Cardiovascular Diseases* 41(6):481-498.
Macris, M. et al. (Jan. 1999). "Minimally Invasive Access of the Normal Pericardium: Initial Clinical Experience with a Novel Device," *Clin. Cardiol.* 22(Suppl. I):I-36-I-39.
Maisch, B. et al. (Jan. 1999). "Intrapreicardial Treatment of Inflammatory and Neoplastic Pericarditis Guided by Pericardioscopy and Epicardial Biopsy-Results from a Pilot Study," *Clin. Cardiol.* 22(Supp. I):I-17-I-22.
Mannam, A.P. et al. (Apr. 1, 2002). "Safety of Subxyphoid Pericardial Access Using a Blunt-Tip Needle," *The American Journal of Cardiology* 89:891-893.
Mattox, K.L. et al. (May 1997). "Newer Diagnostic Measure and Emergency Management," *Ches Surg Clin N Am.* 7(2):213-226, Abstract Only.
McCarthy, P.M. et al. (2008). "Epicardial Atrial Fibrillation Ablation," Chapter 23 in *Contemporary Cardiology: Atrial Fibrillation, From Bench to Bedside*, Natale, A. et al. eds., Humana Press,: Totowa, NJ, pp. 323-332.
McCaughan, J.J. Jr., et al. (Nov. 1957). "Aortography Utilizing Percutaneous Left Ventricular Puncture," located at <http://www.archsurg.com>, last visited on Apr. 7, 2009, 73:746-751.
McClelland, R.R. (1978). "Congenital Aneurysmal Dilatation of the Left Auricle Demonstrated by Sequential Cardiac Blood-Pool Scintiscanning," *J. Nucl. Med.* 19(5):507-509.
Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.
Miller, P.S.J. et al. (Feb. 2005). "Are Cost Benefits of Anticoagulation for Stroke Prevention in Atrial Fibrillation Underestimated?" *Stroke* 36:360-366.
Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.
Morris, J.J. Jr. (1979). "Transvenous versus Transthoracic Cardiac Pacing," Chapter 16 in *Cardiac Pacing: A Concise Guide to Clinical Practice*, pp. 239-245.
Mráz, T. et al. (Apr. 2007). "Role of Echocardiography in Percutaneous Occlusion of the left Atrial Appendage," *Echocardiography* 24(4):401-404.
Naclerio, E.A. et al. (1979). "Surgical Techniques for Permanent Ventricular Pacing," Chapter 10 in *Cardiac Pacing: A Concise Guide to Clinical Practice*, pp. 145-168.
Nakai, T. et al. (May 7, 2002). "Percutaneous Left Atrial Appendage Occlusion (PLAATO) for Preventing Cardioembolism: First Experience in Canine Model," *Circulation* 105:2217-2222.
Nakajima, H. et al. (2004). "Consequence of Atrial Fibrillation and the Risk of Embolism After Percutaneous Mitral Commissurotomy: The Necessity of the Maze Procedure," *The Annals of Thoracic Surgery* 78:800-806.

Non-Final Office Action mailed on Feb. 5, 2014 for U.S. Appl. No. 13/086,389, filed on Apr. 13, 2011, 16 pages.
Non-Final Office Action mailed on Mar. 13, 2008 for U.S. Appl. No. 10/963,371, filed on Oct. 11, 2004, 14 pages.
Non-Final Office Action mailed on Aug. 6, 2008 for U.S. Appl. No. 10/963,371, filed on Oct. 11, 2004, 14 pages.
Non-Final Office Action mailed on Jun. 26, 2009, for U.S. Appl. No. 11/600,671, filed on Nov. 15, 2006, 9 pages.
Non-Final Office Action mailed on Dec. 30, 2009, for U.S. Appl. No. 11/400,714, filed on Apr. 7, 2006, 8 pages.
Non-Final Office Action mailed on Jul. 22, 2010, for U.S. Appl. No. 12/037,802, filed on Feb. 26, 2008, 10 pages.
Non-Final Office Action mailed on Nov. 15, 2010, for U.S. Appl. No.12/055,213, filed on Mar. 25, 2008, 18 pages.
Non-Final Office Action mailed on Feb. 17, 2011, for U.S. Appl. No. 12/212,511, filed on Sep. 17, 2008, 14 pages.
Non-Final Office Action mailed on Apr. 28, 2011, for U.S. Appl. No. 12/055,213, filed on Mar. 25, 2008, 20 pages.
Non-Final Office Action mailed on Oct. 27, 2011, for U.S. Appl. No. 12/363,359, filed on Jan. 30, 2009, 11 pages.
Non-Final Office Action mailed on Nov. 9, 2011, for U.S. Appl. No. 12/363,381, filed on Jan. 30, 2009, 10 pages.
Non-Final Office Action mailed on Dec. 22, 2011, for U.S. Appl. No. 13/033,532, filed on Feb. 23, 2011, 8 pages.
Non-Final Office Action mailed on Mar. 7, 2012, for U.S. Appl. No. 12/124,023, filed on May 20, 2008, 13 pages.
Non-Final Office Action mailed on Apr. 2, 2012, for U.S. Appl. No. 12/212,511, filed on Sep. 17, 2008, 5 pages.
Non-Final Office Action mailed on Sep. 18, 2013, for U.S. Appl. No. 12/055,213, filed on Mar. 25, 2008, 15 pages.
Non-Final Office Action mailed on May 31, 2013, for U.S. Appl. No. 12/124,023, filed on May 20, 2008, 14 pages.
Non-Final Office Action mailed on Apr. 2, 2014, for U.S. Appl. No. 13/033,532, filed on Feb. 23, 2011, 8 pages.
Non-Final Office Action mailed on Jun. 17, 2014, for U.S. Appl. No. 12/363,359, filed on Jan. 30, 2009, 7 pages.
Non-Final Office Action mailed on May 3, 2013 for U.S. Appl. No. 13/086,390, filed Apr. 13, 2011, 10 pages.
Notice of Allowance mailed on Mar. 20, 2014 for U.S. Appl. No. 13/086,390, filed Apr. 13, 2011, 8 pages.
Notice of Allowance mailed on Sep. 17, 2010, for U.S. Appl. No. 10/963,371, filed on Oct. 11, 2004, 7 pages.
Notice of Allowance mailed on Sep. 17, 2010, for U.S. Appl. No. 11/600,671, filed on Nov. 15, 2006, 7 pages.
Notice of Allowance mailed on Nov. 24, 2010, for U.S. Appl. No. 11/400,714, filed on Apr. 7, 2006, 8 pages.
Notice of Allowance mailed on Feb. 22, 2013, for U.S. Appl. No. 12/212,511, filed on Sep. 17, 2008, 8 pages.
Notice of Allowance mailed on Mar. 18, 2013, for U.S. Appl. No. 12/212,511, filed on Sep. 17, 2008, 6 pages.
Notice of Allowance mailed on Mar. 4, 2014, for U.S. Appl. No. 12/055,213, filed on Mar. 25, 2008, 9 pages.
Notice of Allowance mailed on Apr. 1, 2014, for U.S. Appl. No. 12/363,381, filed on Jan. 30, 2009, 9 pages.
Notice of Allowance mailed on Apr. 3, 2014, for U.S. Appl. No. 12/037,802, filed on Feb. 26, 2008, 8 pages.
Odell, J.A. et al. (1996). "Thorascopic Obliteration of the Left Atrial Appendage: Potential for Stroke Reduction?" *Ann. Thorac. Surg.* 61:565-569.
O'Donnell, M. et al. (2005). "Emerging Therapies for Stroke Prevention in Atrial Fibrillation," *European Heart Journal* 7(Supplement C):C19-C27.
Omran, H. et al. (1997). "Left Atrial Appendage Function in Patients with Atrial Flutter," *Heart* 78:250-254.
Onalan, O. et al. (2005). "Nonpharmacologic Stroke Prevention in Atrial Fibrillation," *Expert Rev. Cardiovasc. Ther.* 3(4):619-633.
Onalan, O. et al. (2007). "Left Atrial Appendage Exclusion for Stroke Prevention in Patients With Nonrheumatic Atrial Fibrillation," *Stroke* 38(part 2):624-630.
Ostermayer, S. et al. (2003). "Percutaneous Closure of the Left Atrial Appendage," *Journal of Interventional Cardiology* 16(6):553-556.

(56) References Cited

OTHER PUBLICATIONS

Ota, T. et al. (2006). "Epicardial Atrial Ablation Using a Novel Articulated Robotic Medical Probe Via a Percutaneous Subxiphoid Approach," *National Institute of Health* 1(6):335-340.
Ota, T. et al. (Oct. 2007). "Impact of Beating Heart left Atrial Ablation on Left-sided Heart Mechanics," *The Journal of Thoracic and Cardiovascular Surgery* 134(4):982-988.
Pennec, P-Y. et al. (2003). "Assessment of Different Procedures for Surgical Left Atrial Appendage Exclusion," *The Annals of Thoracic Surgery* 76:2167-2168.
Perk, G. et al. (Aug. 2009). "Use of Real Time Three-Dimensional Transesophageal Echocardiography in Intracardiac Catheter Based Interventions," *J. Am Soc Echocardiogr* 22(8):865-882.
Pollick C. (Feb. 2000). "Left Atrial Appendage Myopathy," *Chest* 117(2):297-308.
Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.
Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.
Robicsek, F. (1987). "Closed-Chest Decannulation of Transthoracically Inserted Aortic Balloon Catheter without Grafting," *Journal of Cardiac Surgery* 2(2):327-329.
Ross, J. Jr. et al. (Jun. 3, 2008). "Transseptal Left Heart Catheterization: A 50-Year Odyssey," *Journal of the American College of Cardiology* 51(22):2107-2115.
Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.
Ruchat, P. et al. (2002). "Off-pump Epicardial Compartmentalization for Ablation of Atrial Fibrillation," *Interactive Cardio Vascular and Thoracic Surgery* 1:55-57.
Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.
Sapp, J. et al. (Dec. 2001). "Electrophysiology and Anatomic Characterization of an Epicardial Accessory Pathway," *Journal of Cardiovascular Electrophysiology* 12(12):1411-1414.
Scharf, C. et al. (2005). "Catheter Ablation for Atrial Fibrillation: Pathophysiology, Techniques, Results and Current Indications," *Continuous Medical Education* 8:53-61.
Scherr, D. et al. (Apr. 2009). "Incidence and Predictors of left Atrial Thrombus Prior to Catheter Ablation of Atrial Fibrillation," *Journal of Cardiovascular Electrophysiology* 20(4):379-384.
Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.
Schneider, B. et al. (2005, e-pub. Aug. 22, 2005). "Surgical Closure of the Left Atrial Appendage—A Beneficial Procedure?" *Cardiology* 104:127-132.
Schweikert, R.A. et al. (Sep. 16, 2003). "Percutaneous Pericardial Instrumentation for Endo-Epicardial Mapping of Previously Failed Ablation," *Circulation* 108:1329-1335.
Schweikert, R.A. et al. (2005). "Epicardial Access: Present and Future Applications for Interventional Electrophysiologists," Chapter 25 in *New Arrhythmia Technolqies*, Wang, P.J. ed., Blackwell Publishing, pp. 242-256.
Seferovic, P. et al. (Jan. 1999). "Initial Clinical Experience with the PerDUCER® Device: Promising New Tool in the Diagnosis and Treatment of Pericardial Disease," *Clin. Cardiol.* 22(Supp I):I-30-I-35.
Sengupta, P.P. et al. (2005). "Transoesophageal Echocardiography," *Heart* 91:541-547.
Sharada, K. et al. (2005). "Non-Surgical Transpericardial Catheter Ablation of Post-Infarction Ventricular Tachycardia," *Indian Heart J* 57:58-61.
Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.
Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.
Smith, P.W. et al. (Nov. 1956). "Diagnosis of Mitral Regurgitation by Cardioangiography," *Circulation* 14:847-853.
Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.
Sosa, E. et al. (1996). "A New Technique to Perform Epicardial Mapping in the EP Laboratory," *J. Cardiovasc. Electrophysiol.* 7(6):531-536.
Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.
Sosa, E. et al. (Dec. 14, 1999). "Different Ways of Approaching the Normal Pericardial Space," *Circulation* 100(24):e115-e116.
Sosa, E. et al. (Jul. 15, 2002). "Gaining Access to the Pericardial Space," *The American Journal of Cardiology* 90:203-204.
Sosa, E. et al. (Apr. 2005). "Epicardial Mapping and Ablation Techniques to Control Centricular Tachycardia," *Journal of Cardiovasc. Electrphsiol.* 16(4):449-452.
Sparks, P.B. et al. (2001). "Is Atrial Flutter a Risk Factor for Stroke?" *Journal of the American College of Cardiology* 38(3):785-788.
Spodick, D.H. (Nov. 1970). "Medical History of the Pericardium," *The American Journal of Cardiology* 26:447-454.
Stewart, J.M. et al. (Apr. 1992). "Bilateral Atrial Appendectomy Abolishes Increased Plasma Atrial Natriuretic Peptide Release and Blunts Sodium and Water Excretion During Volume Loading in Conscious Dogs," *Circulation Research* 70(4):724-732.
Stewart, S. (1974). "Placement of the Sutureless Epicardial Pacemaker Lead by the Subxiphoid Approach," *Ann. Of Thoracic Surg.* 18(3):308-313.
Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.
Stokes, K. (Jun. 1990). "Implantable Pacing Lead Technology," *IEEE Engineering in Medicine and Biology* pp. 43-49.
Stöllberger, C. et al. (2000). "Is the Left Atrial Appendage Our Most Lethal Attachment?" *European Journal of Cardio-Thoracic Surgery* 18:625-626.
Stöllberger, C. et al. (Dec. 2003). "Elimination of the Left Atrial Appendage to Prevent Stroke or Embolism?: Anatomic, Physiologic, and Pathophysiologic Considerations," 124(6):2356-2362.
Stöllberger, C. et al. (2006). "Stroke Prevention by Means of Epicardial Occlusion of the Left Atrial Appendage," *Journal of Thoracic and Cardiovascular Surgery* 132(1):207-208.
Stöllberger, C. et al. (2007). "Arguments Against Left Atrial Appendage Occlusion for Stroke Prevention," *Stroke* 38:e77.
Stöllberger, C. et al. (2007). "Leave the Left Atrial Appendage Untouched for Stroke Prevention!" *Journal of Thoracic and Cardiovascular Surgery* 134(2):549-550.
Su, P. et al. (Sep. 2008, e-pub. May 8, 2007). "Occluding the Left Atrial Appendage: Anatomical Considerations," *Heart* 94(9):1166-1170.
Subramanian, V.A. (Jun. 1997). "Less Invasive Arterial CABG on a Beating Heart," *Ann. Thorac. Surg.* 63(6 Suppl.):S68-S71.
Subramanian, V.A. et al. (Dec. 1997). "Minimally Invasive Direct Coronary Artery Bypass Grafting: Two-Year Clinical Experience," *Ann. Thorac. Surg.* 64(6):1648-1653, Abstract Only.
Suehiro, S. et al. (1996). "Echocardiography-Guided Pericardiocentesis With a Needle Attached to a Probe," *Ann. Thoracic Surg.* 61:741-742.

(56) References Cited

OTHER PUBLICATIONS

Sun, F. et al. (Feb. 2006). "Subxiphoid Access to Normal Pericardium with Micropuncture Set: Technical Feasibility Study in Pigs," *Radiology* 238(2):719-724.
Szili-Torok, T. et al. (2001). "Transseptal Left heart Catheterisation Guided by Intracardiac Echocardiography," *Heart* 86:e11-e15.
Tabata, T. et al. (Feb. 1, 1998). "Role of Left Atrial Appendage in left Atrial Reservoir Function as Evaluated by Left Atrial Appendage Clamping During Cardiac Surgery," *The American Journal of Cardiology* 81:327-332.
Tomar, M. et al. (Jul.-Aug. 2006). "Transcatheter Closure of Fossa Ovalis Atrial Septal Defect: A Single Institutional Experience," *Indian Heart Journal* 58(4):325-329.
Troughton, R.W. et al. (Feb. 28, 2004). "Pericarditis," *The Lancet* 363:717-727.
Ulicny K.S. et al. (Jun. 1992). "Conjoined Subrectus Pocket for Permanent Pacemaker Placement in the Neonate," *Ann Thorac Surg.* 53(6):1130-1131, Abstract Only.
Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.
Von Korn, H. et al. (2006). "Simultaneous Combined Interventional Percutaneous Left Atrial Auricle and Atrial Septal Defect Closure," *Heart* 92:1462.
Wang, T.J. et al. (Aug. 27, 2003). "A Risk Score for Predicting Stroke or Death in Individuals With New-Onset Atrial Fibrillation in the Community," *American Medical Association* 290(8):1049-1056.
Watkins, L. et al. (Nov. 1982). "Implantation of the Automatic Defibrillator: The Subxiphoid Approach," *Ann. of Thoracic Surg.* 34(5):515-520.
W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.
Wolber, T. et al. (Jan. 2007). "Potential Interference of Small Neodymium Magnets with Cardiac pacemakers and Implantable Cardioverter-defibrillators," *Heart Rhythm* 4(1):1-4.
Wolf, P.A. et al. (Oct. 1978). "Epidemiologic Assessment of Chronic Atrial Fibrillation and Risk of Stroke: The Fiamingham Study," *Neurology* 28:973-977.
Wolf, P.A. et al. (Aug. 1991). "Atrial Fibrillation as an Independent Risk Factor for Stroke: The Framingham Study," *Stroke* 22(8):983-988.
Wolf, P.A. et al. (Feb. 9, 1998). "Impact of Atrial Fibrillation on Mortality, Stroke, and Medical Costs," *Arch Intern Med* 158:229-234.
Wong, J.W.W. et al. (2006). "Impact of Maze and Concomitant Mitral Valve Surgery on Clinical Outcomes," *The Annals of Thoracic Surgery* 82:1938-1947.
Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.
Wood, M.A. (Jan. 2006). "Percutaneous Pericardial Instrumentation in the Electrophysiology Laboratory: A Case of Need," *Heart Rhythm* 3(1):11-12.
Written Opinion of the International Searching Authority mailed on Oct. 3, 2011, for PCT Patent Application No. PCT/US2011/00677, filed on Apr. 13, 2011, 6 pages.
Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.
Wyse, D.G. et al. (Dec. 5, 2002). "Of 'Left Atrial Appendage Amputation, Ligation, or Occlusion in Patients with Atrial Fibrillation'," *N Engl J Med* 347(23):1825-1833, Abstract Only.
Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.
Zapolanski, A. et al. (May 2008). "Safe and Complete Exclusion of the left Atrial Appendage, A Simple Epicardial Approach," *Innovations* 3(3):161-163.
Zenati, M.A. et al. (Sep. 2003). "Left Heart Pacing Lead Implantation Using Subxiphoid Videopericardioscopy," *Journal of Cardiovascular Electrophysiology* 14(9):949-953.
Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.
Zenati, M.A. et al. (2005). "Modification of the Left Atrial Appendage," Chapter 12 in *Innovative Management of Atrial Fibrillation*, Schwartzman, David ed., Blackwell Science Ltd., 5 pages.
Non-Final Office Action mailed on Jan. 16, 2013, for U.S. Appl. No. 12/037,802, filed on Feb. 26, 2008, 10 pages.
Non-Final Office Action mailed on May 4, 2015, for U.S. Appl. No. 12/124,023, filed on May 20, 2008, 8 pages.
Notice of Allowance mailed on Oct. 21, 2015, for U.S. Appl. No. 12/124,023, filed on May 20, 2008, 8 pages.
Final Office Action mailed on Aug. 12, 2014, for U.S. Appl. No. 13/033,532, filed on Feb. 23, 2011, 6 pages.
Non-Final Office Action mailed on Oct. 28, 2015, for U.S. Appl. No. 13/033,532, filed on Feb. 23, 2011, 9 pages.
Final Office Action mailed Apr. 1, 2016, for U.S. Appl. No. 13/033,532, filed on Feb. 23, 2011, 8 pages.
Final Office Action mailed on Nov. 14, 2014, for U.S. Appl. No. 12/363,359, filed on Jan. 30, 2009, 10 pages.
Non-Final Office Action mailed on Sep. 10, 2015, for U.S. Appl. No. 12/363,359, filed on Jan. 30, 2009, 13 pages.
Non-Final Office Action mailed on Mar. 17, 2016, for U.S. Appl. No. 12/363,359, filed on Jan. 30, 2009, 10 pages.
Notice of Allowance mailed on Dec. 29, 2014, for U.S. Appl. No. 12/363,381, filed on Jan. 30, 2009, 9 pages.
Non-Final Office Action mailed on Mar. 29, 2013, for U.S. Appl. No. 12/752,873, filed on Apr. 1, 2010, 16 pages.
Non-Final Office Action mailed on Nov. 10, 2014, for U.S. Appl. No. 12/752,873, filed on Apr. 1, 2010, 10 pages.
Notice of Allowance mailed on Jul. 22, 2015, for U.S. Appl. No. 12/752,873, filed on Apr. 1, 2010, 8 pages.
Non-Final Office Action mailed on Jan. 15, 2015, for U.S. Appl. No. 13/086,389, filed on Apr. 13, 2011, 17 pages.
Australian Examination Report dated Mar. 14, 2014, for AU Patent Application No. 2011241104 filed on Apr. 13, 2011; 3 pages.
Australian Notice of Acceptance dated Oct. 20, 2014, for AU Patent Application No. 2011241104 filed on Apr. 13, 2011; 6 pages.
Australian Examination Report dated Dec. 21, 2015, for AU Patent Application No. 2015200387 filed on Apr. 13, 2011; 3 pages.
Japanese Notification of Reasons for Refusal dated Dec. 3, 2014, for Japanese Patent Application No. 2013-504891, filed on Apr. 13, 2011, 9 pages.
Japanese Office Action mailed on Aug. 3, 2015, for Japanese Patent Application No. 2013-504891, filed on Apr. 13, 2011, 4 pages.
Japanese Pre-Appeal Examination Report mailed on Mar. 2, 2016, for Japanese Patent Application No. 2013-504891, filed on Apr. 13, 2011, 5 pages.
Chinese Office Action mailed on Sep. 2, 2014, for Chinese Patent Application No. 201180029064.9, filed on Apr. 13, 2011, 18 pages.
Notification of the Decision to Grant mailed on Jun. 4, 2015, for Chinese Patent Application No. 201180029064.9, filed on Apr. 13, 2011, 1 page.

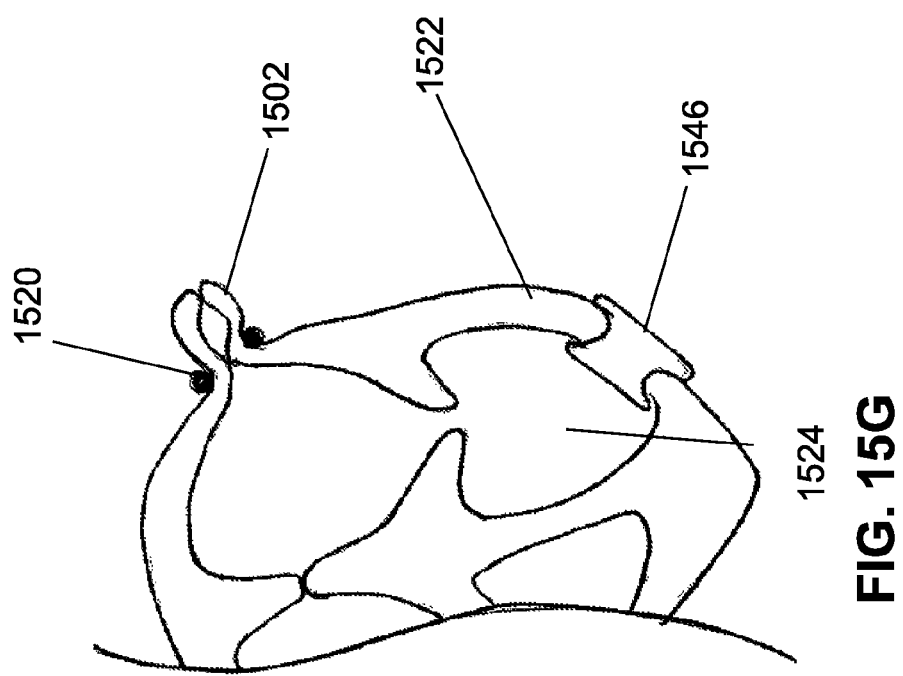

METHODS AND DEVICES FOR ACCESSING AND DELIVERING DEVICES TO A HEART

CROSS-REFERENCE TO RELATED APPLICATIONS

This application is a continuation of U.S. patent application Ser. No. 13/086,390, filed on Apr. 13, 2011, and titled "METHODS AND DEVICES FOR ACCESSING AND DELIVERING DEVICES TO A HEART", the disclosure of which is incorporated herein by reference in its entirety. This application claims priority to U.S. Provisional Patent Application Ser. No. 61/323,816, filed on Apr. 13, 2010, and titled "METHODS AND DEVIECS FOR ACCESSING AND DELIVERING DEVICES TO A HEART"; to U.S. Provisional Patent Application Ser. No. 61/323,801, filed on Apr. 13, 2010, and titled "METHODS AND DEVICES FOR PERICARDIAL ACCESS"; to U.S. Provisional Patent Application No. 61/323,796, filed on Apr. 13, 2010 and titled "METHODS AND DEVICE FOR TREATING ATRIAL FIBRILLATION"; the disclosure of each of which is incorporated herein by reference in its entirety.

FIELD

Described here are devices and methods for delivering one or more devices to the heart.

BACKGROUND

Access to internal and external structures of the heart may be desirable for the treatment of cardiovascular disease. In some cases, the treatment may involve the delivery of devices to the heart. One way in which a heart may be accessed for device delivery is by an intravascular approach. Intravascular pathways to the heart may involve advancing the device from a femoral vein to the vena cava, through which the chambers and valves of the right side of the heart (e.g., right atrium, right ventricle, etc.) may be accessed. The left side of the heart may also be accessed from this approach by a transseptal procedure. Alternatively, the left atrium and left ventricle may be intravascularly accessed by a retrograde pathway from the aorta.

However, intravascular access to the heart may not be ideal in all circumstances, such as for the delivery of larger devices, or for accessing external heart structures. In these circumstances, the heart may be accessed from an epicardial surface. For example, treatment of atrial fibrillation may involve accessing and delivering devices to the left atrial appendage. Such treatments may include closing the left atrial appendage, for example, by suturing along the base or ostial neck of the appendage, where it joins the atrial chamber. Certain treatments to close the appendage may also include cinching the ostial neck, for example, using devices and methods described in U.S. patent application Ser. No. 12/055,213, filed on Mar. 25, 2008, which is hereby incorporated by reference in its entirety. While these devices and methods access external structures of the heart, other devices and methods may be provided to access internal structures of the heart from an epicardial surface.

BRIEF SUMMARY

Described here are devices, methods, and systems for accessing and delivering devices to a heart. In some variations, the left atrial appendage may be used as a port to allow pericardial access to internal structures of the heart. Systems that may be used to provide access to the heart via the left atrial appendage may comprise a first access element with a first alignment member, a second access element with a second alignment member, a piercing element, and a guide/exchange element. Methods of accessing and delivering devices to the heart via the left atrial appendage may comprise advancing a first access element into the left atrial appendage by an intravascular pathway and advancing a second access element towards the left atrial appendage by the pericardial space. The first and second alignment members may attract each other or otherwise form an attachment through the wall of the left atrial appendage so that the first and second access elements are aligned. The first and second access elements may be positioned and aligned in a non-linear configuration (e.g., the first and second access elements may be positioned at an angle or perpendicularly to with respect to each other), or in a linear configuration (e.g., generally at or along their ends). A piercing element may be advanced from either access element to pierce the wall of the left atrial appendage, and an exchange element may be advanced to initiate a track between the inside and outside of the left atrial appendage. Various devices may be delivered to the left atrial appendage from a pericardial surface using the exchange element. Also described here are various methods and devices to close and/or exclude the left atrial appendage.

In one variation, a system for creating an access site through a left atrial appendage comprises a first guide with a first alignment member and a first elongate body with a first longitudinal lumen therethrough, a second guide with a second alignment member and a second elongate body with a second longitudinal lumen therethrough, a piercing element, and a guide element coupled to a proximal end of the piercing element. The guide element may be coupled to the piercing element by an attachment member, such as a spring clamp. The first and second alignment members may be configured to align and/or connect the first and second longitudinal lumens. In some variations, the alignment members may be magnetic, and configured to align the first and second guides in any suitable configuration, for example, in a non-linear configuration (e.g., at an angle), or in a linear configuration (e.g., end-to-end). The first and second longitudinal lumens may be connected along any portion of the first and second alignment members, and/or generally at or along their ends.

One variation of a method for creating an access site through a left atrial appendage comprises advancing a first guide comprising a first longitudinal lumen therethrough to the interior of the left atrial appendage, advancing second guide comprising a second longitudinal lumen therethrough to the exterior of the left atrial appendage, aligning the first and second guides such that the first longitudinal lumen is aligned or in connection with the second longitudinal lumen, advancing a distal portion of a piercing element where a guide element is coupled to a proximal portion of the piercing element, advancing the distal portion of the piercing element until at least a portion of the guide element is in the first longitudinal lumen and the second longitudinal lumen, and withdrawing the piercing element. The piercing element may be advanced from the first longitudinal lumen into the second longitudinal lumen to pierce the left atrial appendage, or may be advanced from the second longitudinal lumen into the first longitudinal lumen to pierce the left atrial appendage. In some variations, the first and second guides are aligned, for example, in a non-linear configuration (e.g., at an angle), or in a linear configuration (e.g., end-to-end). The first and second longitudinal lumens may be connected along any portion of the first and second guides, and/or generally at or along their ends.

Also described here is a system for accessing and delivering devices through the left atrial appendage. One example of such a system comprises a first access element comprising a first alignment member and first longitudinal lumen therethrough, a second access element comprising a second alignment member and second longitudinal lumen therethrough, a piercing element comprising a proximal and distal end, a closure element, and a tissue-affecting device. The first and second alignment members may be configured to align the first and second longitudinal lumens. The first and second alignment members may also be configured to create hemostasis. First and second alignment members may be magnets of opposite polarity, or magnetic components. The first alignment member may comprise a first aperture that is continuous with the first longitudinal lumen, and the second alignment member may comprise a second aperture that is continuous with the second longitudinal lumen. In certain variations, the first and second alignment members may comprise interconnecting members that may communicate through tissue. A system for accessing and delivering devices through the left atrial appendage may further comprise a cannula, an exchange element, and/or a vacuum member. The exchange element may be coupled to the proximal end of the piercing element. The tissue-affecting device may be configured to be advanced over the first or second access device, and may comprise one or more radio-opaque and/or echogenic markers. Some variations of a tissue-affecting device may have one or more configurations, for example, a first collapsed configuration and a second expanded configuration. Tissue-affecting devices may be expandable, and in some cases, may be a balloon. Additionally or alternatively, tissue-affecting devices may be an ablation device or an occlusion device.

Systems for closing a left atrial appendage are also described here. One variation of a system may comprise a first access element having a size and length for accessing the left atrial appendage through the vasculature and comprising a first alignment member, a second access element having a size and length adapted for accessing the pericardial space from a subthoracic region and comprising a second alignment member that is configured to align with the first alignment member, and a piercing element comprising a proximal and distal end. A system for closing a left atrial appendage may also comprise an occlusion member, where the occlusion member may have one or more apertures. In some variations, the occlusion member may be couplable to the first access element, and/or may be expandable. One example of an expandable occlusion member is a balloon. The system may further comprise an exchange element, and in some cases, the exchange element may be coupled to the proximal end of the piercing element. The first and second alignment members may be magnets, where the magnets are located at the distal ends of the first and second access elements. The alignment members may also comprise interconnecting members. Certain variations of alignment members may comprise radio-opaque and/or echogenic markers. Furthermore, instructions for using one or more components of the above system may be included.

Various methods may be used with the devices above to access and deliver devices to the heart via the left atrial appendage. For example, one method may comprise advancing a first access element comprising a first longitudinal lumen to the interior of the left atrial appendage, advancing a second access element comprising a second longitudinal lumen to the exterior of the left atrial appendage, aligning the first and second access elements such that the first and second longitudinal lumens are in communication through the wall of the left atrial appendage, advancing a piercing element through the second longitudinal lumen into the first longitudinal lumen, where the piercing element spans both longitudinal lumens, advancing an exchange element through the second longitudinal lumen into the first longitudinal lumen, where the exchange element spans both longitudinal lumens, and advancing a tissue-affecting device into the left atrial appendage over the exchange element. Some methods may use a first access element further comprising a first alignment member with a first aperture where the s aperture is continuous with the first longitudinal lumen, and a second access element further comprising a second alignment member with a second aperture where the second aperture is continuous with the second longitudinal lumen. Some variations of the method may use an exchange element that is coupled to a proximal end of the piercing element. Various tissue-affecting devices may be used with the method. For example, the tissue-affecting device may be advanced in a collapsed configuration, and/or may be an occluding device, ablation device, or balloon. Echogenic and/or radio-opaque markers may be included with some variations of a piercing element, exchange element, and/or tissue-affecting device. The method may also comprise occluding the left atrial appendage with the tissue-affecting device, and/or may comprise withdrawing the first and second access devices after the tissue-affecting device has been advanced. Some methods may also include closing the left atrial appendage before withdraw the first and second access devices.

Systems that may be used to create an access site through the left atrial appendage using the devices and methods here are also provided. For example, one variation of a system for creating an access site comprises a sheath having a size and length adapted for accessing the pericardial space, a first guide catheter comprising a first alignment member, a second guide catheter comprising a second alignment member, a guide element housed in the second guide catheter, and a suture element coupled to one of the guide element. The first and second guide catheters may be housed in the sheath. The first and second alignment members may be magnetic. A third alignment member may also be included in the system.

Other systems for closing a left atrial appendage may comprise a closure element and a positioning device comprising grooves shaped to accommodate the closure element. In some variations, the closure element may be a continuous loop, and the positioning device may be circular, where the grooves circumscribe the perimeter of the positioning device. In some instances, the positioning device may be configured to occlude the left atrial appendage.

Yet another variation of a system for closing a left atrial appendage is described here. The system may comprise an occlusion device with a geometry that approximates the shape of the anatomical ostium of the left atrial appendage and a suture that is configured to couple the occlusion device to the tissue around the ostium of the left atrial appendage. In some variations, the occlusion device may be stretchable, and/or biocompatible. The occlusion device may be a mesh or a sheet that effectively blocks any exchange between the left atrial appendage and the left atrium.

Another method that may be used to deliver devices to a heart through the left atrial appendage is described here. Such a method may comprise advancing a stabilization device to the exterior of the left atrial appendage, where the stabilization device has a longitudinal lumen therethrough.

The stabilization device may optionally have a closure element. Then, the stabilization device may engage and stabilize the left atrial appendage, and once stabilized, a piercing element may be advanced through the longitudinal lumen to create an access site in the wall of the left atrial appendage. A guide element may then be advanced through the access site to contact a targeted portion of the heart for the delivery of a tissue-affecting device. The tissue-affecting device may be advanced using the guide element. In some variations, the method may further comprise closing the access site after delivering the tissue-affecting site with the closure element. For example, the access site may be closed by closing the left atrial appendage with the closure element.

BRIEF DESCRIPTION OF THE DRAWINGS

FIG. 7I depicts in flowchart fashion, one example of a method for accessing and delivering devices to the heart via the left atrial appendage.

FIG. 8K depicts in flowchart fashion one example of a method for accessing and delivering devices to the heart through an access site or port in the left atrial appendage.

FIGS. 15A-15G and 16A-16D depict variations of methods for accessing internal structures of the heart and delivering one or more devices thereto.

DETAILED DESCRIPTION

Described here are devices, systems, and methods for accessing and delivering devices to a heart using the left atrial appendage as a port or access site to the interior of the heart. When the left atrial appendage is used as a port, a distal portion of one or more treatment devices may be passed from a location outside the heart, through the tissue of the left atrial appendage, and into the heart. Any suitable locations of the heart (e.g. left atrium, left ventricle, the left atrioventricular (mitral) valve, right atrium, right ventricle, the right atrioventricular (tricuspid) valve, the semilunar valves, chordae tendinae, papillary muscles, etc.,) and/or the vasculature (e.g., right pulmonary veins, left pulmonary veins, the aorta, or the like) may be accessed via a left atrial appendage access sites, such that one or more treatment procedures (e.g., an ablation procedure, mitral valve replacement, implant deliver, combinations thereof, or the like) may be performed at one or more of these locations, as will be described in more detail below. At least a portion of the treatment devices may be removed from the left atrial appendage, and the left atrial appendage may be closed, occluded and/or excluded. It should be understood that these devices and methods may be used to access any desired portion of the heart and for the treatment of various heart conditions.

Figure 1:
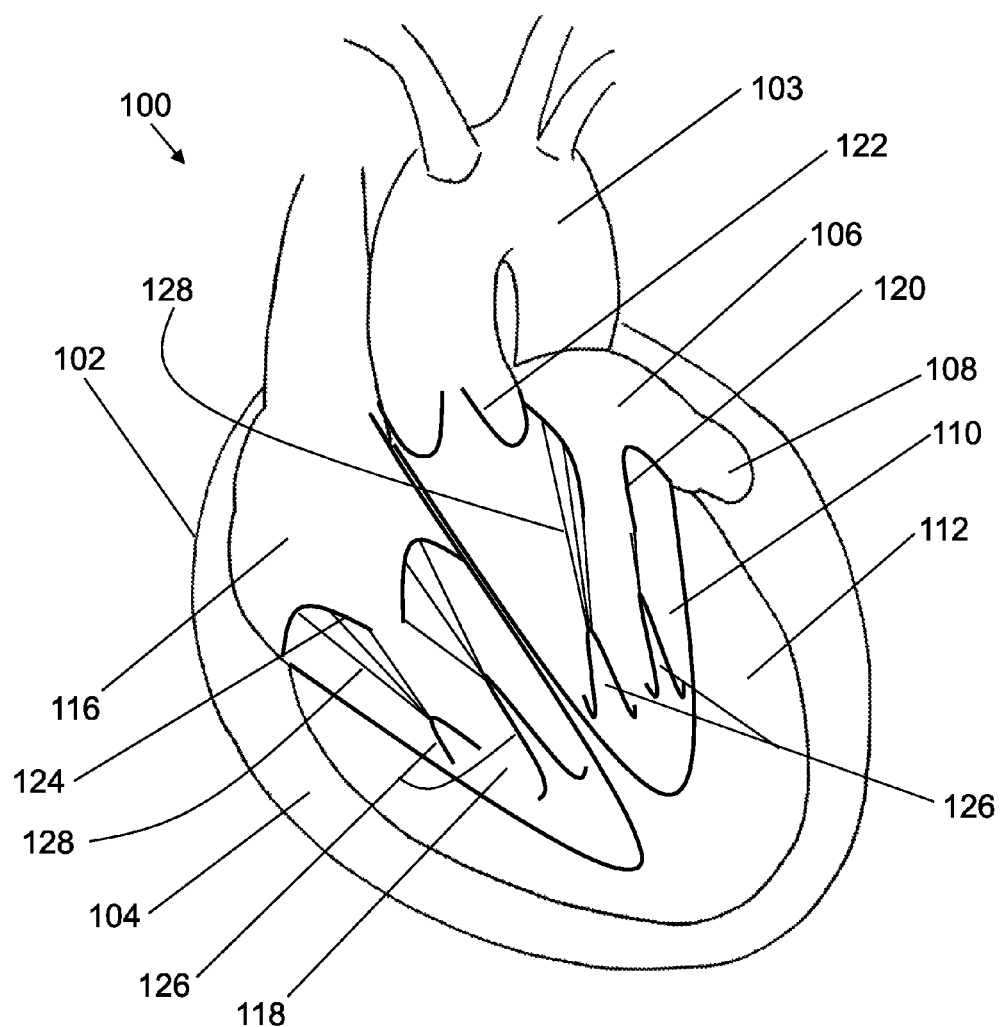
FIG. 1 depicts a cross-section of a heart.

With regard to accessing and delivering devices to the heart, it may be helpful to start by briefly identifying and describing the relevant heart anatomy. FIG. 1 depicts a cross-sectional view of a heart (100). Shown there are the left atrium (106), left atrial appendage (108), left atrioventricular (mitral) valve (120), left ventricle (110), aortic semilunar valve (122), and the aortic arch (103). Also depicted there are the right atrium (116), right atrioventricular (tricuspid) valve (124), and right ventricle (118). Papillary muscles (126) and chordae tendinae (128) are also schematically represented. From FIG. 1, it can be seen that the left atrial appendage (108) is adjacent to, and is formed from, the wall of the left atrium (106). Similarly, the right atrial appendage (not shown) is adjacent to and formed from the wall of the right atrium (116). The heart (100) is enclosed by a pericardium (102). The pericardium (102) is filled with a fluid that separates it from the heart. The space between the pericardium (102) and the heart (100) is the pericardial space (104). The left atrial appendage (108) lies within the boundaries of the pericardium (102) (i.e., inside of the pericardial space (104)), and is in close proximity to the ventricular wall (112). The left atrial appendage typically has a tubular shape that approximates a cone, with a slight narrowing or neck in the plane of the orifice where it joins the left atrium (106).

Generally, one or more treatment devices may access one or more of these heart structures or the surrounding vasculature during the course of a treatment, where the devices may be withdrawn after treatment. In some variations, one or more treatment devices may implant or otherwise deliver one or more implantable devices or substances. The devices, systems, and methods described here may also be used to provide access to various structures of the heart (e.g., the left atrium, left ventricle, the left atrioventricular (mitral) valve, right atrium, right ventricle, the right atrioventricular (tricuspid) valve, the semilunar valves, chordae tendinae, papillary muscles, and/or any other heart structure) or the vasculature via the left atrial appendage (i.e., using the left atrial appendage as an access port or access site) in order to deliver one or more of these treatment devices thereto and to perform one or more procedures thereat. For example, in some variations, an access site or port via the left atrial appendage may be used to access a heart valve for the treatment of valve regurgitation. Additionally or alternatively, an access site through the left atrial appendage may be used to place one or more pacing devices (e.g., pacemaker leads) where needed, and may also be used to help position various components of a ventricular assist device (e.g., the inflow and/or outflow tubes). As appropriate, the left atrial appendage may be used as an access port for the installation of various heart monitors and/or defibrillators that may be positioned, for example, at the inferior region of the left ventricle, near a sinoatrial node, or on an epicardial surface of the heart (i.e., in the pericardial space). The left atrial appendage may also be useful in delivering one or more treatment devices to the vasculature. For example, in some variations, one or more ablation devices may be delivered to the right or left pulmonary veins through the LAA. Illustrative examples of treatment device delivery through the left atrial appendage will be described in more detail below.

Also described here are devices and methods for accessing and delivering one or more devices to the heart using an atrial or ventricular wall as a port or access site to the interior of the heart. In some instances, the devices and methods may be used to place a device through the wall of an atrium or ventricle (e.g., via a transapical access) which may help regulate hemostasis through the atrial or ventricular access site. In some variations, these devices and methods may be used in combination with one or more of the devices and methods for access and delivering devices to the heart using the left atrial appendage as a port or access site, as will be described in more detail below.

Additionally, in some variations it may be desirable to close off the left atrial appendage. In patients with atrial fibrillation, the left atrial appendage (108) is the most common location for thrombus formation, which, in time, may dislodge and cause a devastating stroke. Because stroke is the primary complication of atrial fibrillation, the left atrial appendage is frequently closed and/or excluded from the left atrium in those patients undergoing procedures to treat atrial fibrillation, and is often removed or excluded at the time of other surgical procedures, such as mitral valve surgery, to reduce the risk of a future stroke. The devices and systems described here may help ensure proper closure of the left atrial appendage, at the neck or base of the left atrial appendage, along the anatomic ostial plane. In this way, exclusion of the entire left atrial appendage from systemic circulation may be facilitated. Additionally, in variations where the left atrial appendage is used as an access port, as will be described below, closing the left atrial appendage may help to prevent blood loss from the heart through the left atrial appendage.

I. Devices and Methods for Accessing and Delivering Devices to a Heart

Described below are devices and methods that may be used to access the heart to deliver one or more devices and/or therapies to an internal structure of the heart (e.g., left atrium, left ventricle, the left atrioventricular (mitral) valve, right atrium, right ventricle, the right atrioventricular (tricuspid) valve, the semilunar valves, chordae tendinae, papillary muscles, etc.) or the vasculature (e.g., right pulmonary vein, left pulmonary vein, or the like) using the left atrial appendage as an access and/or delivery port. Additionally or alternatively, as will be described in more detail, one or more devices may be positioned on or around the outside of the left atrial appendage, which may also assist in the advancement, positioning, and/or operation of devices within the heart. While the devices and methods are described herein as being used to form an access port through the left atrial appendage, it should be appreciated that in some instances the devices or methods may also be used to form an access port at any suitable location on the heart (e.g., right atrial appendage, atrial or ventricular wall, etc.), where the location may be determined in part by the pathology of the heart and the approach most conducive to treating that pathology. For illustrative purposes, devices and methods for accessing and delivering devices to the heart via the left atrial appendage will be described below.

Generally, the devices and methods described here may be utilized to obtain access to the left atrial appendage. Once access to the left atrial appendage has been obtained, a guide element or other device (e.g., a treatment device) may be advanced through tissue of the left atrial appendage. In some variations, the access devices and methods may be utilized to advance a guide element (e.g., a guide wire) through the tissue of the left atrial appendage. In these variations, one or more treatment devices may be advanced over the guide element such that they enter the heart. In other variations, one or more dilators may be advanced over the guide wire to enlarge the access site through the left atrial appendage. In some of these variations, the dilators may be used to place one or more catheters across the tissue of the left atrial appendage, through which one or more treatment devices may be advanced. Once a treatment device has been introduced into the heart, it may be further advanced, actuated or otherwise utilized to perform one or more procedures in the heart or vasculature. It should also be appreciated that in some variations, the access devices and methods may place a treatment device across tissue of the left atrial appendage without needing to first place a guide element through tissue of the left atrial appendage.

Access to the left atrial appendage may be achieved in any suitable manner. In some variations, the left atrial appendage may be accessed using a pericardial approach, in which one or more access devices may be advanced externally from the heart, through the pericardium, and toward the left atrial appendage. These devices may be used to place one or more guide elements or other devices into the heart through the tissue of the left atrial appendage. In other variations, the left atrial appendage may be accessed using a combination of a pericardial approach and an intravascular approach (e.g., where one or more devices may be advanced to the interior of the left atrial appendage through the vasculature). For example, in some variations a first guide may be advanced intravascularly to place the a distal portion of a first guide inside the left atrial appendage, and a second guide may be advanced through the pericardium and toward an external surface of the left atrial appendage. In these variations, the first and second guides may be used to advance a guide element (e.g., a guide wire) or another device through the pericardium and into the left atrial appendage, as will be described in more detail below.

In some variations, a closure/stabilization device may be temporarily closed around the left atrial appendage to close the left atrial appendage around a guide element or treatment device. The closure device may be placed around the left atrial appendage prior to or during placement of a guide element or other device into the left atrial appendage, or after removal of the guide elements and/or other devices from the left atrial appendage. Closure of the closure device around the left atrial appendage may help to manage hemostasis and/or prevent blood loss through the left atrial appendage. For example, in variations where a guide wire is placed through the left atrial appendage, the closure device may close the device around the guide wire, which may help prevent blood from exiting the heart through the access site created in the left atrial appendage. When one or more devices are advanced over the guide wire (e.g., one or more dilators, a treatment device or the like) and into the heart via the left atrial appendage access site, the closure device may be temporarily opened to accommodate the new device, and re-closed around the new device to maintain a hemostatic seal.

In some instances, it may also be desirable to occlude, block, or otherwise close the left atrial appendage. In some variations, the guide element may be used to place one or more occlusive devices inside of the left atrial appendage or at the ostium of the left atrial appendage to block off the left atrial appendage from the rest of the heart. In other variations, the guide element may be removed from the left atrial appendage, and the closure device may be used to close off the left atrial appendage. In some of these variations, a portion of the closure device (e.g., a suture loop) may be left behind to hold the left atrial appendage in a closed configuration. Illustrative examples of the devices and methods that may be utilized to perform the above-mentioned steps are described in more detail below.

A. Devices and Methods for Intravascular and Pericardial Access

As mentioned above in some variations, access to the left atrial appendage may be achieved via a combined intravascular and pericardial approach. FIGS. 2A-2J illustrate variations of devices that may be used to provide an access pathway from one side of the left atrial appendage to the other (e.g., providing access to the interior of a heart from outside of a heart via a left atrial appendage). It should be appreciated that these devices may be used to provide an access pathway through any suitable tissue, as will be described in more detail below. In some variations, these devices may be utilized to place a portion of a guide element, one or more treatment devices, and/or one therapeutic agents into the interior of the heart from outside of the heart.

Figure 2A:
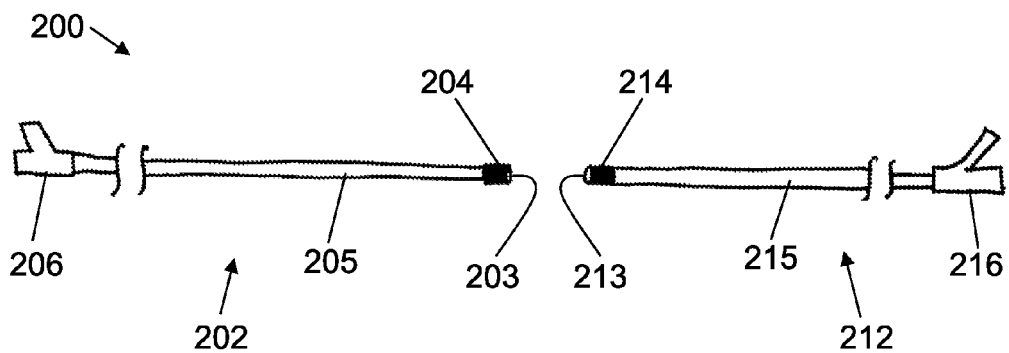
FIGS. 2A-2J depict several variations of a device that may be used to create an access port through a tissue, e.g. the wall of a left atrial appendage, such that devices may be passed from one side of the tissue to the other side.

FIGS. 2A and 2H-2J show one variation of an access device (200) comprising a first guide (202), a second guide (212), a piercing element (220), and a guide element (222). As depicted in FIG. 2A, the first and second guides (202, 212) may each comprise an elongate body (205, 215), magnetic alignment elements (204, 214), and actuating handles (206, 216). The elongate bodies (205, 215) may each have a lumen (203, 213) therethrough. Lumens (203, 213) may be sized and shaped for the passage of piercing element (220) and/or guide element (222) therethrough. The actuating handles (206, 216) may be located at the proximal ends of the first and second guides (202, 212), and may be used to navigate the first and second guides (202, 212). Additionally, the actuating handles (206, 216) may also be utilized to advance or navigate piercing element (220) and guide element (222) through one or more of lumens (203, 213). The actuating handles (206, 216) may also be used to control any tools that may be introduced through the elongate bodies (205, 215). Generally, the first guide (202) may be advanced intravascularly into the heart, the second guide (212) may be advanced from outside the heart into the pericardial space, and the access device (200) may be used to place a guide element (222) into the interior of the heart from the exterior of the heart, as will be described in more detail below.

The first and second guides (202, 212) may have any suitable lengths and/or dimensions, where the lengths and dimensions may be determined in part by the desired access path to the heart (e.g., intravascularly from a femoral vein, or intercostal access via a thoracostomy, a sternotomy, a thoracotomy, etc.), as well as the length and size of the vascular structures that the guides may be inserted through. The dimensions may also be determined in part by the location and anatomy of the targeted portion of the heart. For example, the guides may have a diameter of about 0.010 inch (in) to about 0.050 in, about 0.020 in to about 0.030 in, or may have a diameter that is smaller than the diameter of a vessel or artery through which the guide will be advanced. In some variations, the first guide (202) may have a diameter of about 0.025 in and the second guide (212) may have a diameter (212) of about 0.035 in. Similarly, the first and second guides may have any suitable length, for example, from about 50 cm to about 300 cm or more, from about 100 cm to about 200 cm, from about 200 cm to about 250 cm, and the like. The first and second guides (202, 212) may have the same length, but need not. For example, in some variations, the first guide may have a length of about 250 cm and the second guide may have a length of about 90 cm. The outer diameter of the alignment elements may also be selected as desirable. For example, it may be from about 0.05 in to about 0.2 in or more. Similarly, the first and second guides (202, 212) may have the same diameter, but need not. In some variations, the outer diameter of the alignment member of the first guide is about 0.106 in and the outer diameter of the alignment member of the second guide is about 0.170 in.

While the elongate bodies (205, 215) of both first and second guides (202, 212) are shown as having lumens (203, 213) extending therethrough, it should be appreciated that in some variations, one or more of the guides may not comprise a lumen extending through the elongate body thereof. In variations where one or more of the elongate bodies (205, 215) of the first and second guides (202, 212) comprises a lumen, the lumen may have any suitable configurations. In some variations, the elongate body lumen may have a partially-open geometry, e.g., have a C-shaped cross-section, or may have a longitudinal side aperture that extends along at least a length of the lumen. In other variations, the elongate body lumen may have a closed-shaped geometry. The elongate body lumens associated with a guide may be formed by any suitable method. For example, the elongate body may be made from a tube with one or more longitudinal lumens therethrough, e.g., a hypotube, or any suitable tubular structure, where the one or more longitudinal lumens are formed in the course of manufacturing the tube. Any number or configuration of longitudinal lumens may be associated with a needle or piercing element as needed for accessing the pericardial space. Some variations of elongate body lumens may have one or more side slots or apertures.

The first and second guides may also comprise one or more alignment members. Alignment members may be any suitable alignment members (e.g., interconnecting elements, one or more vacuum members, radio-opaque or echogenic markers, members that are configured to produce an audible response, magnets, etc.) that may attach, attract or communicate with each other through tissue. For example, in the variation of access device (200) shown in FIG. 2A, the first and second guides (202, 212) may comprise magnetic alignment elements (204, 214). While shown in FIG. 2A as being located at the distal ends of the first and second guides (202, 212), the magnetic alignment elements (204, 214) may be located at one or more portions along the lengths of the respective guides. The magnetic alignment elements (204) and (214) may exert an attractive force on each other to help align the first and second guides (202, 212). For example, in instances where first guide (202) is placed inside of the atrial appendage, and the second guide (212) is placed in the pericardial space near the left atrial appendage, the magnetic alignment elements (204) and (214) may attract the first and second guides (202, 212) toward each other through the tissue of the left atrial appendage to help align the guides (202, 212) relative to each other. When the guides (202, 212) are aligned, they may be aligned in any suitable configuration. In some variations, the guides may be configured to be aligned in a non-linear configuration (e.g., such that the elongate body of one guide is positioned at an angle with respect to the elongate body of the other guide), or in a linear configuration (e.g., end-to-end). The alignment members may be configured to align the first and second elongate body lumens (203, 213) at any point along the elongate bodies, and/or generally at or along their ends.

In variations in which the alignment members comprise one or more magnetic components, the magnetic components may be made from or comprise any suitable magnetic material, e.g., a rare earth magnet, such as neodymium-iron-boron, cobalt-samarium, or other powerful fixed magnet elements. In some variations, the magnets may be electromagnets that may be selectively actuated (e.g., by one of actuating handles (206, 216)). In some variations, one or more of the magnetic components may comprise an aperture. For example, in the variation of access device (200) described above in respect to FIG. 2A, the magnetic alignment elements (204, 214) may comprise apertures that are continuous with the elongate body lumens (203, 213), which may permit devices (e.g., a piercing element, a guide element, or the like) that pass through the elongate bodies to be passed through the magnets. It should be understood that while the elongate body lumens (203, 213) and the magnetic components (204, 214) are illustrated as being generally circular, they may also be of any other geometry suitable for passing access devices therethrough or therein or therealong, e.g., rectangular, triangular, hexagonal, semi-circular, slotted, etc.

Figure 2B:
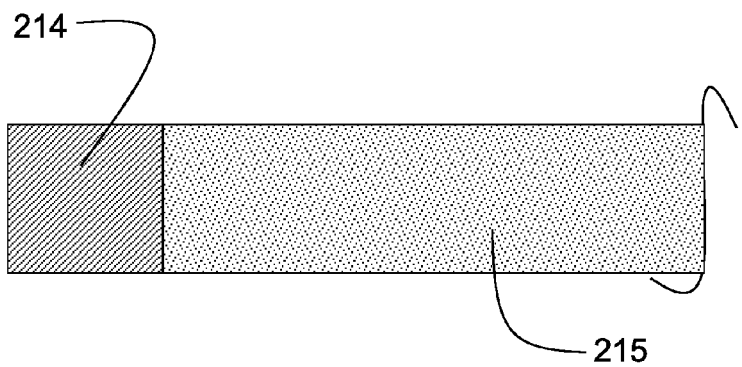
Figure 2C:
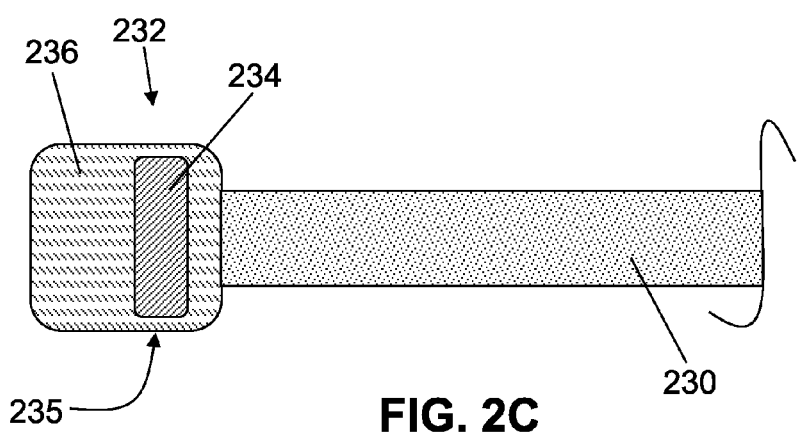

The magnet components (204, 214) may be affixed (e.g., by form-fit, friction-fit, snap-fit, screw-fit, soldering, welding, bonding by adhesives, etc.) to the distal portion of the guides in any suitable manner. For example, in some variations, the magnetic alignment elements (204, 214) may be attached directly to the distal end of the elongate bodies (205, 215), as depicted in side views in FIGS. 2A and 2B. In other variations, the magnetic components may be encapsulated at the distal ends of the guides. FIGS. 2C-2G depict cross-sectional views of some examples of alignment members comprising encapsulated magnetic components. FIG. 2C depicts an alignment member (232) located at a distal end of an elongate body (230), where the alignment member (232) comprises a cup (235) and magnetic component (234) embedded in an encapsulation layer (236). The cup (235) may be any hollow or partially-hollow structure, and although depicted in FIG. 2C as a rectangle, but may have any suitable geometry, as will be described later. In some variations, the cup (235) may be flush with the elongate body (230), e.g., they may have equal widths, similar to what is shown in FIG. 2B.

Figure 2D:
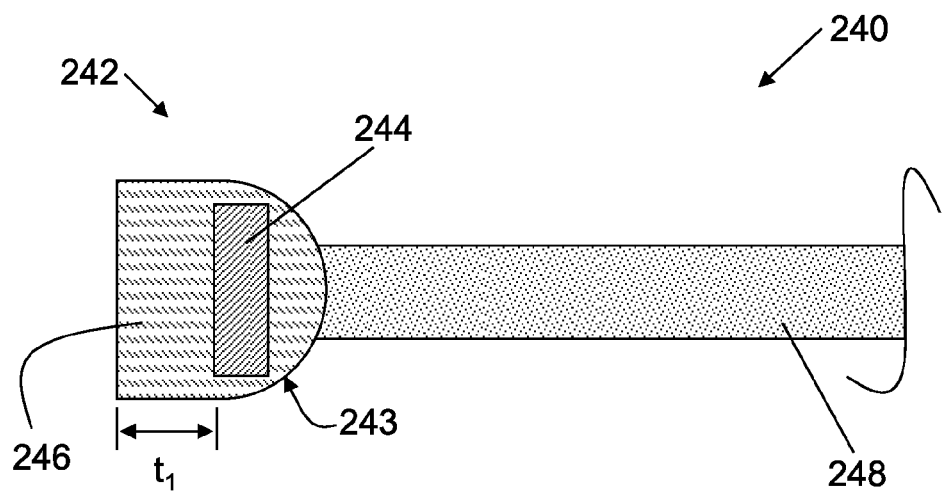
Figure 2E:
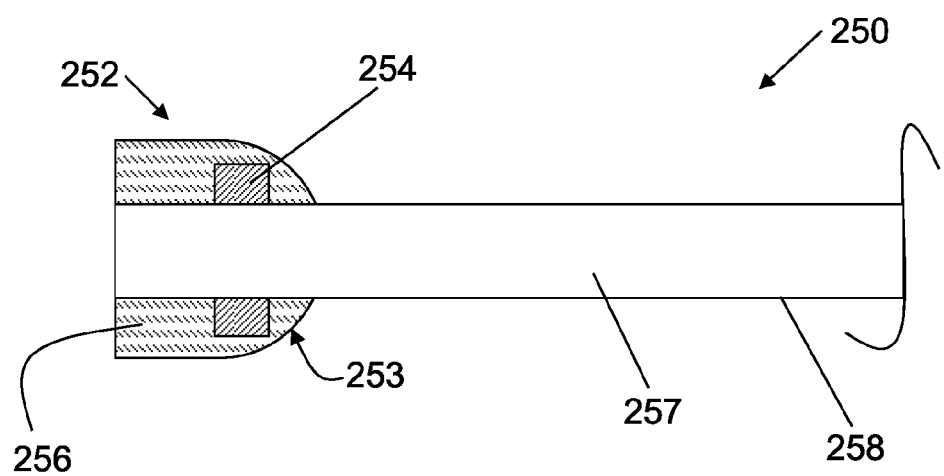

Another variation of a guide (240) with an elongate body (248) and alignment member (242) is shown in FIG. 2D, where a cup (243) of the guide (240) has a rounded shape, and the encapsulation layer (246) may have a thickness ($t_1$), measured from a distal edge of magnetic component (244) to the distal boundary of the alignment member (242), as indicated in FIG. 2D. The thickness ($t_1$) may be varied according to the desired force of attraction between two magnetic alignment members, i.e., a thinner encapsulation layer may permit magnetic components to attach to each other more strongly, while a thicker encapsulation layer may result in a weaker attachment. For example, the thickness ($t_1$) may be from about 0.001 millimeter (mm) to about 20 mm, and may be adjusted according to the thickness of the tissue and the desired attachment strength between alignment members through that tissue. For example, the attractive force needed for two alignment members to attach through a thin tissue wall may not be as strong as the attractive force needed for the alignment members to attach through a thick tissue wall. The thickness ($t_1$) may be a physical barrier that may be adjusted to limit or increase the attachment strength between alignment members. FIG. 2E depicts another variation, where the guide (250) has an elongate body (258) that has a longitudinal lumen (257) therethrough. The longitudinal lumen (257) may extend through an alignment member (252), comprising a cup (253) and a magnetic component (254). The cup (253) and the magnetic component (254) may both have lumens that are in communication with lumen (257). As with the alignment member (242), the magnetic component (254) may be embedded in encapsulation layer (256). The lumen (257) may be sized and shaped for advancing various devices therethrough, as will be described below.

Figure 2F:
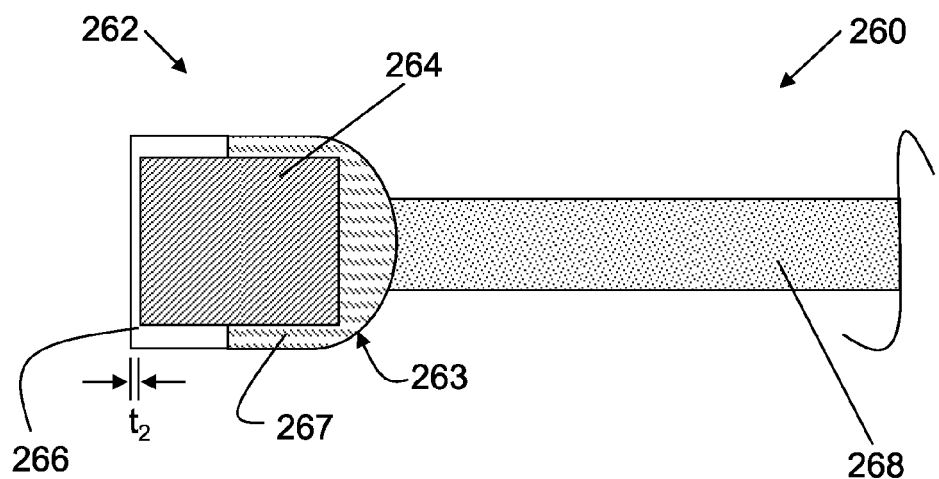
Figure 2G:
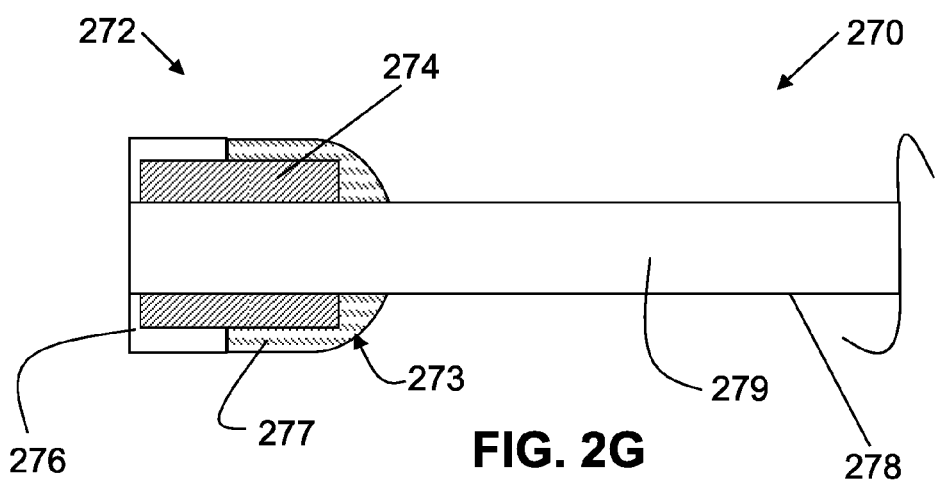

In some variations, it may be desirable for the encapsulation layer to be as thin as possible, which may greatly reduce the physical barrier between magnetic alignment members, in some cases, to obtain greater attachment strength. For example, FIG. 2F depicts a guide (260) with an elongate body (268) and an alignment member (262), where the alignment member comprises a cup (263) with a magnetic component (264) embedded in an encapsulation layer (267). The magnetic component (264) is sized such that it extends distally past the cup (263) and the encapsulation layer (267). The portion of the magnetic component (264) that extends beyond the cup may be encased with a coating layer (266). The coating layer (266) may have a thickness ($t_2$), where the thickness ($t_2$) is measured from a distal edge of the magnetic component (264) to the distal boundary of the alignment member (262), as shown in FIG. 2F. In some variations, the thickness ($t_2$) of the coating layer (266) may be significantly thinner than thickness ($t_1$) of encapsulation layer shown in FIG. 2D. The thickness ($t_2$) may be from about 0.0001 mm to about 10 mm, and may be adjusted according to the thickness of the tissue and the desired attachment strength between alignment members through that tissue. The thickness ($t_2$) is a physical barrier that may be adjusted to limit or increase the attachment strength between alignment members. Another variation of a guide (270) comprising an elongate body (278) with a longitudinal lumen (279) therethrough is shown in FIG. 2G. An alignment member (272) comprising a cup (273), and a magnetic component (274) embedded in the encapsulation layer (277) may be attached to the distal portion of the elongate body (278). The cup (273) and the magnetic component (274) may both have lumens that may be in communication with the lumen (279). As with the guide (260), the magnetic component (274) may be sized to extend distally past the cup (273). The portion that extends past the cup may be encased in a coating layer (276), as described above in FIG. 2F.

The encapsulated magnetic alignment members shown in FIGS. 2C-2G are merely illustrative examples. Various features of the alignment members, such as the size, shape, material of magnetic components, the thickness of an optional encapsulation layer and/or coating layer, the geometry and size of the distal portion of the alignment members, the presence or absence of a lumen therethrough, may be adjusted according to the size and location of the targeted region of the heart, as well as the desired attachment strength through the heart tissue. These features may also be adjusted in accordance with the size and shape of the devices to be advanced over or through the guides. In some variations, the encapsulation layer and/or coating layer may not surround the entire surface of the magnetic component. The encapsulation layer and coating layer may be applied by any methods appropriate to the material used. For example, the encapsulation layer may be made from epoxy, Terylene™, polyester, etc., which may be applied by filling the cup. When present, the coating layer may be provided over the magnetic component by thin-film deposition of a biocompatible material, such as gold, platinum, Terylene™, polyester, or any other biocompatible, inert, materials that may be applied by thin-film deposition methods. The coating layer may be applied such that the thickness around the exposed surface area of the magnetic component is uniform throughout, or the thickness may vary across different regions of the magnetic component. The encapsulation layer may be configured to retain the magnetic component within the cup, but the magnetic component may additionally or alternatively be bonded (e.g., using adhesives), welded, soldered, or otherwise securely attached to the cup. The cup (235) may be made from any biocompatible material, for example, stainless steel and the like, that provides sufficient strength and structural support to retain the magnetic component (234) therein. Any of the above described guides and/or alignment members may be used with the access device (200) described above and the other devices described below.

Figure 2H:

As mentioned above, the access device (200) may comprise a piercing element. A piercing element may be any suitable structure or device that is capable of puncturing tissue. For example, FIG. 2H shows one variation of piercing element (220) that may be used with access device (200), comprising a microneedle wire that is flexible with a piercing tip (221) located at the distal end. In some variations, the piercing element (220) may be formed from a hypotube, and/or may be made of stainless steel or nickel titanium alloy. The piercing element may be any suitable size or length, for example, the piercing element (220) may have a diameter of about 0.014 in, about 0.018 in, or about 0.025 in, and may have a length from about 50 cm to about 300 cm or more, from about 100 cm to about 200 cm, from about 200 cm to about 250 cm, and the like. The lengths and dimensions of a piercing element may be determined in part by the desired access path to the heart (e.g., intravascularly from a femoral vein, or intercostal access via a thoracostomy, a sternotomy, a thoracotomy, etc.), the location and anatomy of the targeted portion of the heart, as well as the size of the vascular structures that the piercing element may pass through and the lumen size of the guide. Examples of other devices that may pierce or puncture tissue (e.g., heart tissue, pericardial tissue, etc.) are described in U.S. Provisional Patent Application Ser. No. 61/323,801, filed on Apr. 13, 2010, and titled "METHODS AND DEVICES FOR PERICARDIAL ACCESS", which was previously incorporated by reference, and U.S. patent application Ser. No. 13/086,328 entitled "Methods and Devices for Pericardial Access," filed Apr. 13, 2011, which is hereby incorporated by reference in its entirety. The piercing device may also be configured pierce or puncture tissue using chemicals such as enzymes, current or voltage pulses, RF pulses, electrocautery, chemical cautery, laser cautery, and the like.

Figure 2I:
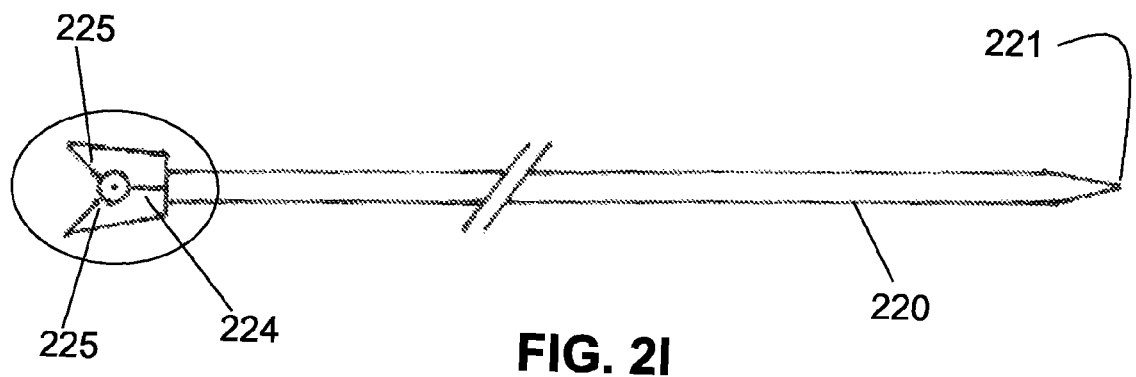
Figure 2J:
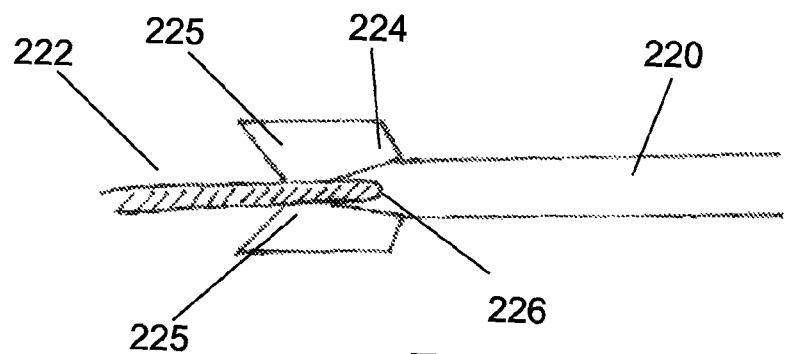

Generally, one end of a piercing element may be attached or connected, temporarily or permanently, to a guide element, and may be used to help advance the guide element to and/or through the site of tissue puncture. Piercing elements and guide elements may be coupled in any suitable manner. In some variations, one or more clamps, clips, or other grasping members may be used to couple the guide element to piercing element. For example, in some variations, such as that depicted in FIGS. 2I and 2J, a clamp (224) may connect piercing element (220) to guide element (222). As shown there, one or more portions of the clamp (224) may be attached to the proximal portion of the piercing element (220), while the jaws (225) may be connected in a hinged manner and spring-loaded such that the clamp is biased towards the closed position. In some variations, a spring clamp may be used to couple a piercing element and a guide element, as shown in FIG. 2I, where the clamp pressure may be adjusted as appropriate. The profile of a clamp may be any size that may be accommodated through the elongate body lumen (203, 213), for example, about 0.025 in. Other mechanisms may be used to couple the piercing element and guide element, for example, they may be temporarily coupled by snap-fit, hooks, adhesion, etc., or permanently coupled by welding, soldering, bonding, adhesion, etc. In some variations of an access device, the piercing element and guide element may be formed together (e.g., molded, welded, soldered, and/or braided together), or may have a unibody structure. In some variations, a single device may act as both a penetration member and a guide element. For example, in some variations the guide element itself may have a distal piercing tip, which may be advanced to pierce through tissue.

As mentioned immediately above, the access devices and systems described here may be used to place a guide element across tissue. The guide element may comprise any suitable structure. For example, the variation of guide element (222) depicted in FIG. 2J may comprise a standard guide wire. In some of these variations, the guide element (222) may be a 018" standard guide wire. In other variations, the guide element may be a suture, tube, cannula, or other structure that is sized and shaped to be accommodated by one or more elongate body lumens (e.g., lumens (203, 213) of first and second guides (202, 212). A guide element may be made of any biocompatible material, and may possess any variety of mechanical properties as appropriate for accessing the target tissue. In some variations, the guide element (222) may be made of stainless steel, polymeric alloys, or metallic alloys, such as nickel titanium alloys. A guide element may be inelastic or elastic, and may have shape memory as desired. The distal tip (226) of the guide element (222) may be sharpened to pierce tissue, or alternatively may be relatively blunt and atraumatic.

Figure 3A:
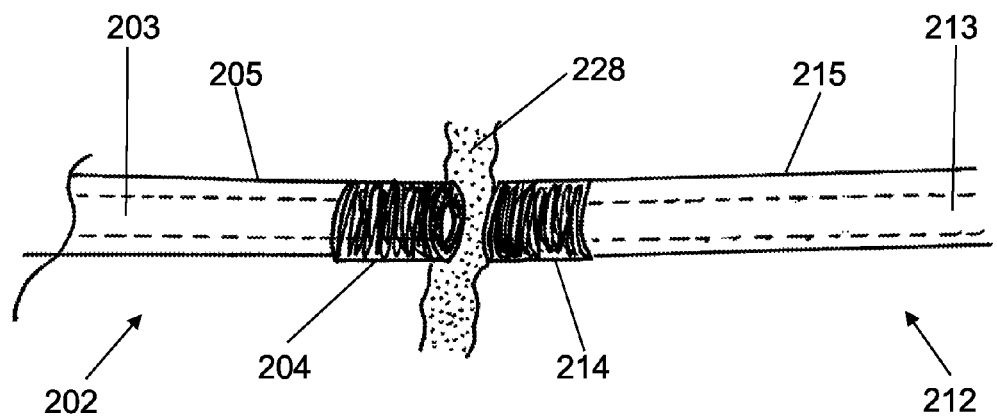
FIGS. 3A and 3B depict the use of the devices shown in FIGS. 2A-2J to create an access port through tissue.
Figure 3B:
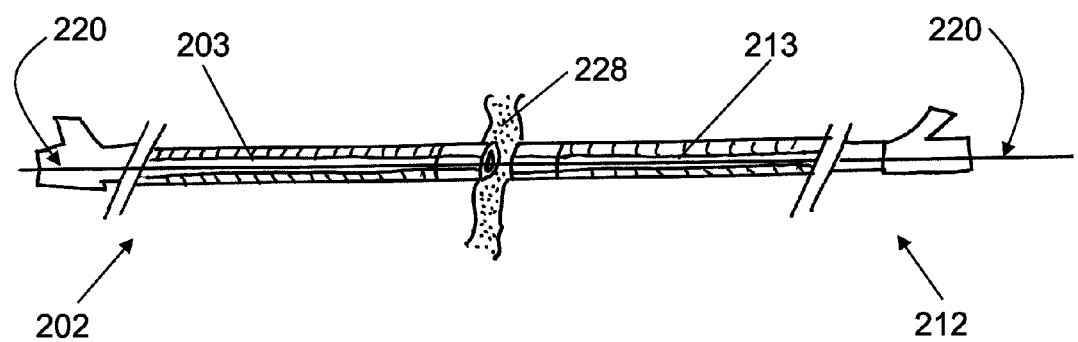

One or more variations of the access devices described above with respect to FIGS. 2A-2J may be used to provide access from a first side of a tissue to a second side of the tissue. FIGS. 3A and 3B depict one way in which access device (200) may be used to provide an access site through a tissue wall (228). The methods described below may be used in a surgical procedure or a minimally invasive procedure. When used for cardiac procedures, the methods may be used in a beating heart or a stopped heart.

As shown in FIG. 3A, the first guide (202) may be advanced such that it is positioned on a first side of a tissue (228), while the second guide (212) may be advanced such that it is positioned on a second side of the tissue (228). Advancement and/or positioning may be done under one or more direct or indirect visualization techniques (e.g., fluoroscopic visualization, ultrasound visualization, a combination thereof, or the like). The guides (202, 212) may be positioned simultaneously (e.g., the first guide (202) and the second guide (212) are advanced and/or positioned at or roughly at the same time) or sequentially (e.g., the first guide (202) may be placed before the second guide (212) is placed, and vice versa). The alignment members may be configured to help align the first and second guides (202, 212). For example, magnetic alignment elements (204, 214) may be configured such that they attract each other (e.g., the magnets (204, 214) may be of opposite polarity). The attraction of the magnets may generally attract each other through the tissue (228) such that the guides (202, 212) are aligned (in this variation, generally at or along their ends). This attraction may create close contact between guides (202, 212) and tissue (228). In some variations, the magnets may be arranged or have a sufficient attractive force such that they may have a hemostatic interaction, which may help reduce the loss of blood when providing an access pathway through a vascular structure, such as an artery or the heart. While shown in FIG. 3A as being aligned in a generally linear arrangement, the guides (202, 212) may alternatively be aligned in a non-linear arrangement (e.g., at an angle, or perpendicularly). As mentioned above, the magnetic components (204, 214) may couple the guides together at any point along the guides, and/or generally at or along their ends.

Once the desired alignment has been achieved, the piercing element (220) may be advanced from the first guide (202), through the first elongate body lumen (203), through the tissue (228), into the second elongate body lumen (213), and through the second guide (212), as shown in FIG. 3B. As the piercing element (220) passes through the tissue, it may create an access site or port through the tissue. The piercing element may continue to be advanced through the first guide (202), the tissue (228), and the second guide (212), and the engagement between the piercing element and the guide element (222) may cause the guide element to be similarly advanced through the tissue (228). Once the guide element (222) has passed through the tissue and is positioned so that one end of the guide element (222) is on one side of the tissue, and the other end of the guide element (222) is on the opposite side, the piercing element (220) may be disengaged, and the piercing member and the first and second guides may be withdrawn to leave the guide element (222) in place. In variations where the guide element acts as a piercing member, the guide element may be advanced directly from the first guide (202) through the tissue. In other variations, a piercing member may be advanced from the first guide (202) to puncture through tissue (228), the piercing member may be withdrawn from the tissue (228) and the first guide (202), and a separate guide element may be advanced through the first guide (202) and the puncture (not shown) created in tissue (228).

In some variations, the guide element (222) may be fully advanced through first and second guides (202, 212) such that each end of the guide element (222) extends outside of the body. In other variations, the guide element (222) may be advanced such that a first end of the guide element (222) is positioned outside of the body, and a second end of the guide element (222) is positioned inside of the heart or vasculature.

While each of guides (202, 212) are shown in FIGS. 3A and 3B as having lumens (203, 215) extending therethrough, it should be appreciated that in some variations one of the guides need not have a longitudinal lumen extending therethrough. For example, in some variations, a first guide having a lumen may be advanced to and positioned at a first side of the tissue (228), and a second guide without a lumen may be placed on a second side of the tissue. Alignment elements of the first and second guide may be used to align the guides as described above. A piercing element (or a guide element with a piercing member) may be advanced through the lumen of the first guide and through the tissue to place an end of the piercing member or guide member through the tissue.

In some variations, an optional stabilizing member may be used to help secure and position the guide element to prevent any unintentional loss of communication between the two sides of the tissue via the guide element, e.g., where the guide element may be "pulled back" into one guide and no longer spans between the two sides of the tissue. Stabilizing members may include brackets, braces, rings, bands, washers, etc. which may secure the engagement between the guide element and the tissue wall.

As mentioned above, the first and second guides may be withdrawn after the piercing element and/or guide element is placed through and/or secured through the tissue. In some variations, one or more treatment devices (e.g., therapeutic, diagnostic, visualization, etc.) may be advanced directly over the guide element and through the tissue, and the treatment devices may be used to perform one or more procedures through the tissue, such as those devices described in more detail below. In other variations, a series of dilators may be advanced over the guide element to enlarge the access site created by the piercing element so as to facilitate device advancement across the tissue. In some of these variations, the dilators may be used to place a catheter across tissue, and one or more devices may be introduced across the tissue through the catheter. Additionally or alternatively, in some variations, a one-way valve, such as check or non-return valve, may be inserted and installed at the access site to preserve hemostasis. Other hemostatic devices and methods may be employed as appropriate for the location of the access site. For example, in variations where the access device is used to provide access across tissue of the left atrial appendage, one or more devices having a closure element may be positioned such that the closure element is positioned around the left atrial. In these variations, the closure element may be selectively tightened around the left atrial appendage to help stabilize the left atrial appendage and/or control hemostasis, as described in more detail below.

The access device (200) described above may be used to place a guide element across any suitable tissue (228) (e.g., tissue of a heart wall, the right atrial appendage, or the like). In some variations, access device (200) may be used to place a guide element across an external ventricle or atrial wall, as will be described in more detail below. In other variations, the tissue (228) may be the wall of a left atrial appendage.

Figure 4:
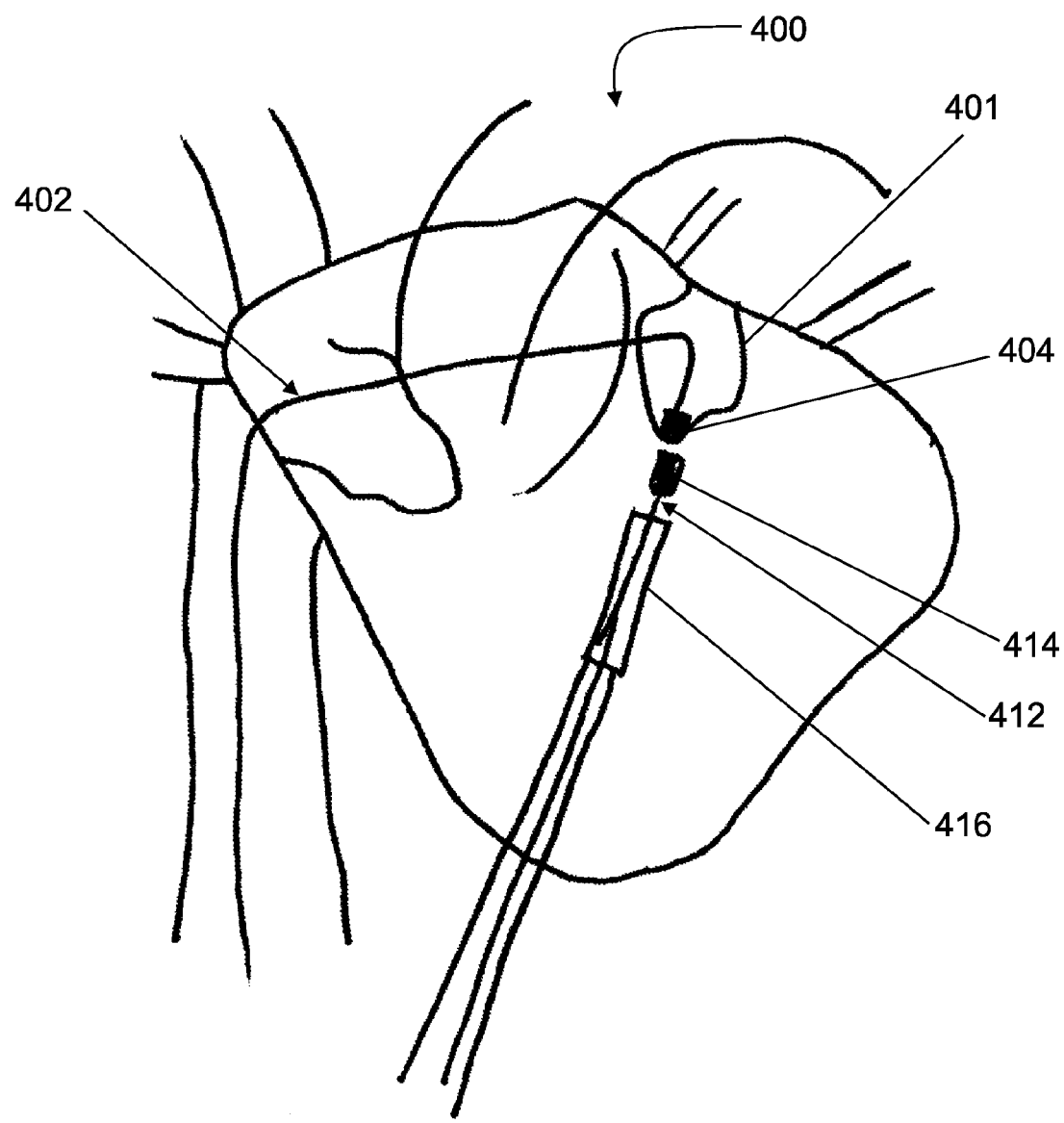
FIG. 4 illustrates the use of a device similar to that depicted in FIGS. 2A-2J to access and deliver a tissue-affecting element to the heart via the left atrial appendage.

FIG. 4 depicts one example of how an access device may be used to create an access pathway for a device to the heart using the left atrial appendage as an access port. As shown there, a first guide (412) may advanced into the pericardial space to a left atrial appendage (401) of a heart (400), where the distal portion of the first guide (412) comprises a first alignment member (414). Optionally, a second guide (402) may be advanced intravascularly (e.g., via a transeptal approach) to the interior of the left atrial appendage (401). The distal portion of the second guide (402) may comprise a second alignment member (404). The first and second alignment members (414, 404) may be magnetic, and may be configured to attract to each other to help align first and second guides (412, 402), as described in more detail above. The magnetic components of the first and second alignment members may be encapsulated or coated as described previously. The first guide (412) may be advanced toward the exterior side of the heart (400), and the optional second guide (404) may be advanced approximately towards the first guide (412), and positioned so that the first and second alignment members (414, 404) also may attach or interact through the wall of the left atrial appendage. As shown in FIG. 4, the first and second guides may be aligned generally at or along their ends, but in other variations, may have alternate arrangements, as described previously. Magnetic alignment members may rely on magnetic forces to position the first and second guides. Once positioned and aligned, a piercing element and/or guide element may be advanced through the tissue of the left atrial appendage, such as in one of the manners described immediately above, to create an access site through the wall of the left atrial appendage.

In some variations, as shown in FIG. 4, a catheter comprising a tissue-affecting element (416) may be advanced over the first guide (412) towards the left atrial appendage (401). The tissue-affecting element (416) may be any device that applies a force or energy to tissue, for example, an ablation element for ablating fibrillating tissue (e.g., laser, cryogenic, high frequency ultrasound, chemical, etc) or a mechanism for tissue-manipulation for cardiac repair and/or remodeling (e.g., for applying pressure, extraction, incision, suturing, etc.). In some variations, the tissue-affecting element (416) may be advanced over the second guide (402). Guides with alignment members as shown in FIG. 4 may be used to deliver devices to cardiac and vascular tissues, as well as to other non-vascular tissues. While shown in FIG. 4 as being advanced over first guide (412), in variations where the first and second guides (412, 404) are used to place a guide element, access catheter or the like across tissue of the left atrial appendage, the catheter may be advanced over of the guide element, through the access catheter, or the like.

Figure 5A:
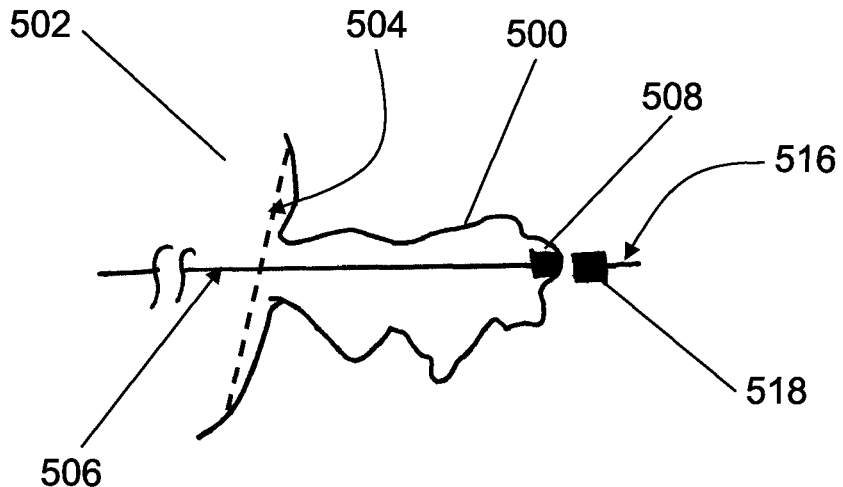
FIGS. 5A-5C depict one way in which the position of a device that is delivered to a left atrial appendage, e.g. an expandable member, may be adjusted.
Figure 5B:
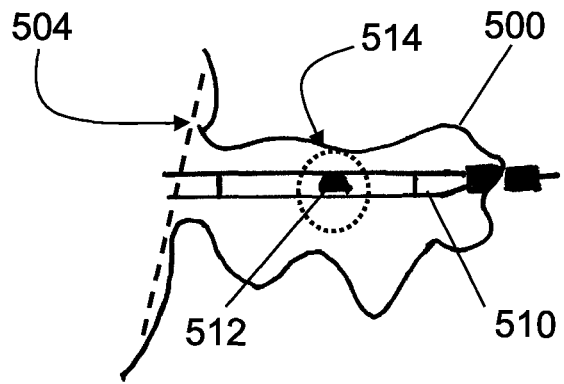
Figure 5C:
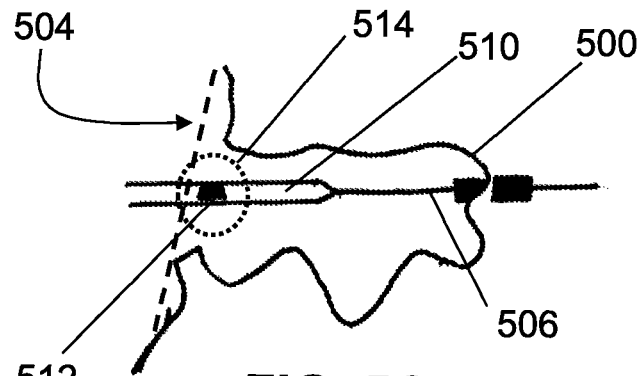

While the devices of FIGS. 2A-2J may be used as described and depicted in FIG. 4 to provide an access site or port to the heart via the left atrial appendage, the access devices may be used to assist in the positioning and operation of devices within the heart. An example of such a method is shown in FIGS. 5A-5C. As shown there, the precise location and position of a device may be adjusted according to anatomical landmarks in the target region of the heart without re-positioning the guides. For example, an expandable device (514) delivered to the left atrial appendage (500) may be adjusted so that it is positioned along the border of the anatomical ostium (504) (the opening that separates the left atrium from the left atrial appendage). While the re-positioning of a device delivered intravascularly is shown here, it should be understood that this method may also be used to re-position devices delivered from a pericardial approach. As shown in FIG. 5A, a first guide (506) comprising a distal alignment member (508) is advanced into a left atrial appendage (500) of a heart (502), while a second guide (516) comprising a distal alignment member (518) may be advanced into the pericardial space adjacent to the left atrial appendage (500). Either of these guides may be advanced under any of a variety of visualization techniques, e.g., fluoroscopic visualization, ultrasound visualization, some combination thereof, etc. The first and second guides (506, 516) are positioned such that the alignment members (508, 518) may be aligned generally at or along their ends by any mechanism, e.g., by mechanical interfit, or magnetic forces, etc., as previously described. FIG. 5B depicts the delivery of a device, for example, an expandable device (514), e.g., a balloon, which may be used for closing and/or excluding the left atrial appendage (500) when in the expanded configuration. The expandable device (514) may be coupled to a catheter (510) that may be advanced over, or in conjunction with, a guide element. The location of the expandable device (514) and/or catheter (510) may be determined by any suitable method, e.g., ultrasound, X-ray, fluoroscopy, and the like. For instance, the catheter (510) may comprise a radio-opaque marker (512) so that the location of the expandable device (514) in the left atrial appendage (500) may be determined. Different markers may be used depending on the imaging modality used. The location of the expandable device shown in FIG. 5B may be adjusted, for example, to the position shown in FIG. 5C by sliding the catheter (510) over the guide (506). As shown there, the expandable device (514) is positioned close to the anatomical ostium (504), which may be a desirable location for the deployment of a closure device to close and/or occlude the left atrial appendage (500). Advancing a catheter over a first guide that is secured in position by a second guide may allow for a greater range of adjustability and stability without the additional steps of repositioning the guides. Optionally, a piercing member and guide wire may be advanced thereto and create an access site in the left atrial appendage as previously described. This may provide access of the interior and exterior of the heart, as well as the delivery of devices from the exterior to the interior of the heart, and vice versa.

B. Devices and Methods for Pericardial Access

Figure 6A:
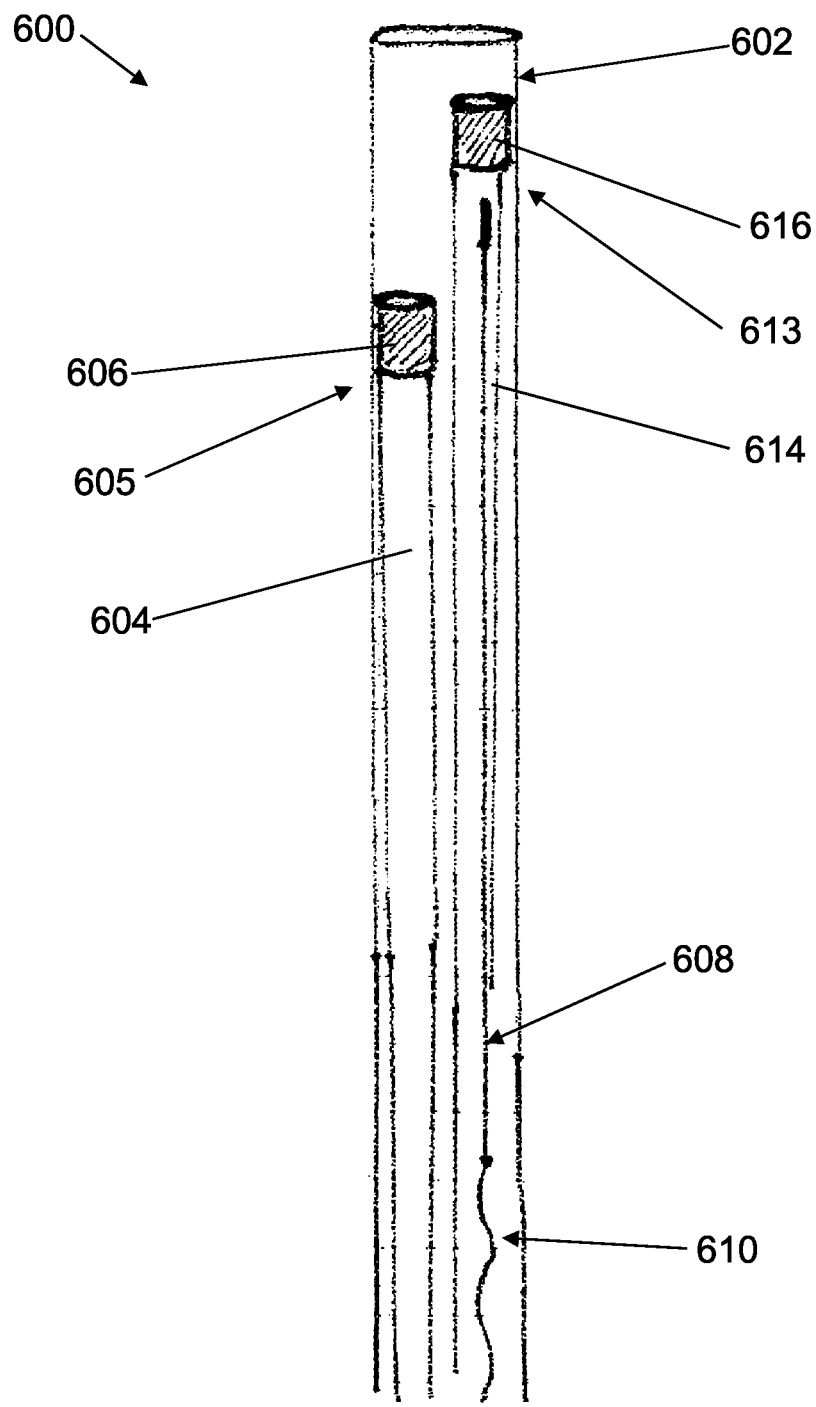
FIG. 6A depicts a variation of a device for accessing and delivering devices to the heart via an access port through a left atrial appendage.

Some devices and methods may provide access to internal and external portions of the heart from a pericardial approach to the left atrial appendage. An example of a device that may be used to access and/or deliver devices to a heart from a pericardial approach using the left atrial appendage as a port is shown in FIG. 6A. The access device (600) comprises a cannula (602), a first catheter (604) and a second catheter (614) enclosed within the cannula (602), a guide element (608) within the second catheter (614), and a suture element (610) attached at one end of the guide element (608). The first catheter (604) may comprise a first alignment member (606) located at a distal portion (605) of the first catheter, and the second catheter (614) may comprise a second alignment member (616) located at a distal portion (613) of the second catheter. In some variations, the first and second catheters may be enclosed within a sheath or other similar tubular structure. The suture element (610) is coupled to the proximal portion of the guide element (608), both of which are enclosed within the second catheter (614). The guide element (608) may be a flexible wire made of any suitable materials (e.g., nickel titanium alloy or any polymeric materials), and may have a size of about 0.014 in to about 0.025 in. The first and second catheters (604, 614) may be made of a flexible material that allows it to conform to the anatomical structures through which it is navigating. In some variations, the first and second catheters (604, 614) may have one or more pre-shaped curves as needed, or may be flexed via a living and/or mechanical hinge. The first and second catheters may be independently advanced and/or withdrawn into the cannula (602), or may be advanced and/or withdrawn in concert. The first and second alignment member (606, 616) may be any suitable alignment device, such as those described above, e.g., they may be magnets that rely on magnetic attraction for alignment. For example, the first alignment element (606) may help align the first catheter (604) to an external alignment element, e.g., an alignment element that is positioned in the interior of a left atrial appendage. Alternatively or additionally, the first alignment element (606) may help align the first catheter (604) to the second catheter (614) by attaching to the second alignment element (616).

Figure 6B:
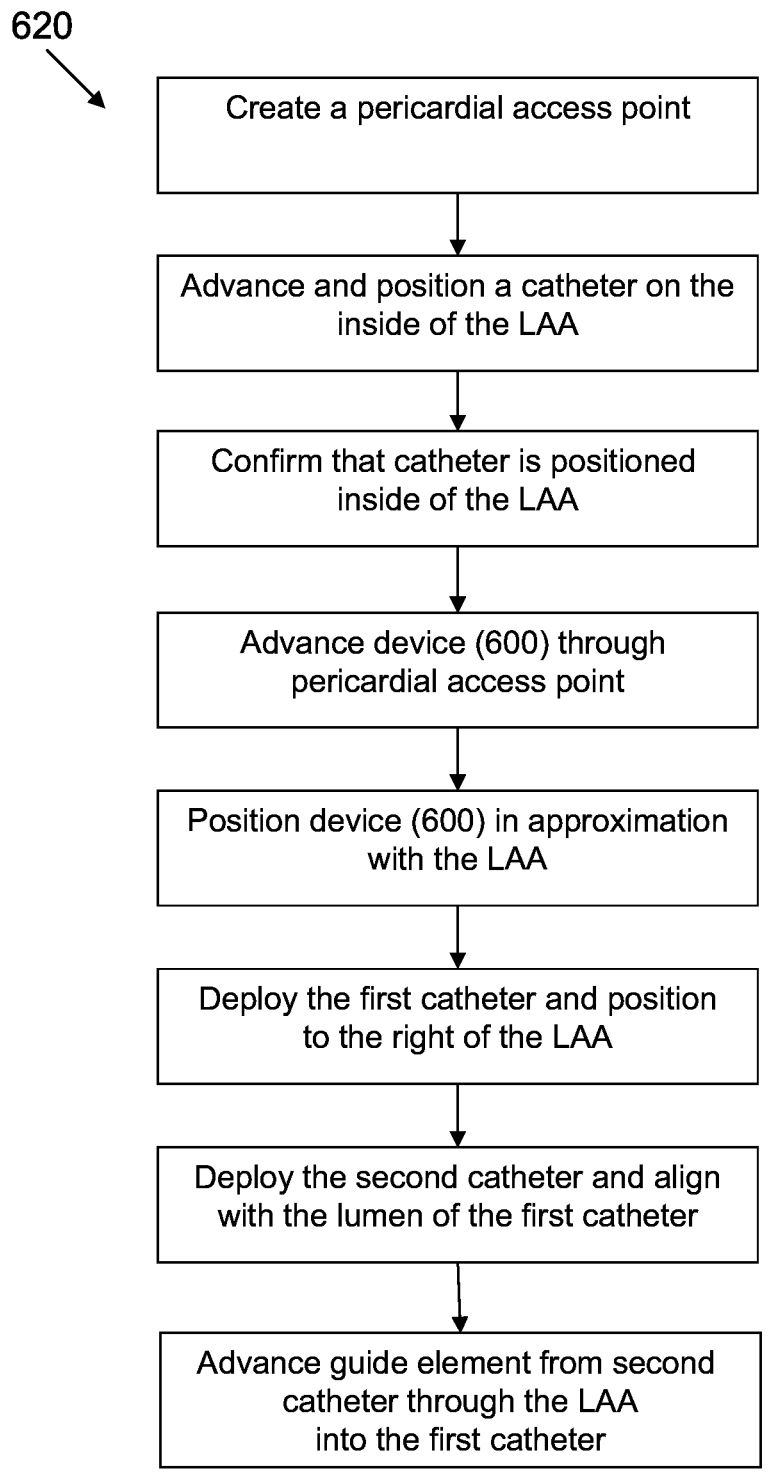
FIG. 6B depicts one method for accessing and delivering devices to a heart using the device from FIG. 6A.

One variation of a method (620) that may be used to access and deliver devices to the heart via the left atrial appendage is shown in the form of a flowchart in FIG. 6B. Access to the pericardium may be obtained, in some variations using one or more of the methods described in U.S. Provisional Patent Application Ser. No. 61/323,801, filed on Apr. 13, 2010, and titled "METHODS AND DEVICES FOR PERICARDIAL ACCESS", and U.S. patent application Ser. No. 13/086,328 entitled "Methods and Devices for Pericardial Access," filed Apr. 13, 2011, each which was previously incorporated by reference. In some variations, an intravascular catheter that comprises an alignment feature, e.g., a magnet, may be advanced to the inside of the LAA. The position of the intravascular catheter may be confirmed using fluoroscopic imaging. The access device (600) may be advanced through the access site towards the LAA, and positioned adjacent to the LAA. The first catheter (604) may be deployed by extending from cannula (602), and positioned to the right of the LAA. In some variations, the first catheter (604) may have a pre-shaped curve configured to curve to the right, while in other variations, the first catheter may have a flexible or mechanical hinge that may allow the catheter to be bent. The second catheter (614) may be deployed such that it is opposite the first catheter (604), e.g., with the LAA positioned between them, and the first and second alignment members (606, 616) may position the first and second catheters such that the catheter lumens are aligned. The guide element (608) may be advanced from the lumen of the second catheter, through the LAA, into the lumen of the first catheter, until the suture element (610) spans both the first and second catheter lumens. Once this has been confirmed, the access device (600) may be withdrawn, and devices may be advanced towards and/or into the LAA using the guide element (608) and/or the suture element (610).

In some variations, access device (600) or a similar device may be used to place a guide element or other device around a tissue structure such as a blood vessel or the left atrial appendage. FIGS. 12A-12F illustrate different variations of methods for using an access device (1200) to place a guide element (1202) or other device around a tissue structure (1204). As shown there, access device (1200) may comprise a cannula (1206), a first guide (1208), and a second guide (1210). First (1208) and second (1210) guides each may comprise a lumen (1212) extending therethrough, and may further comprise a magnetic alignment element (1214) at a distal end thereof. First (1208) and second (1210) guides may be at least partially housed inside cannula (1206), and may be advanceable out of a distal end of the cannula (1206). In some variations, first (1208) and second (1210) guides may be housed in a single lumen (not shown) of cannula (1206). In other variations, first (1208) and second (1210) guides may be housed in separate lumens (e.g., a first lumen and a second lumen, respectively). It should be appreciated that cannula (1206) may comprise any suitable number of lumens (e.g., one, two, or three or more).

Figure 12A:
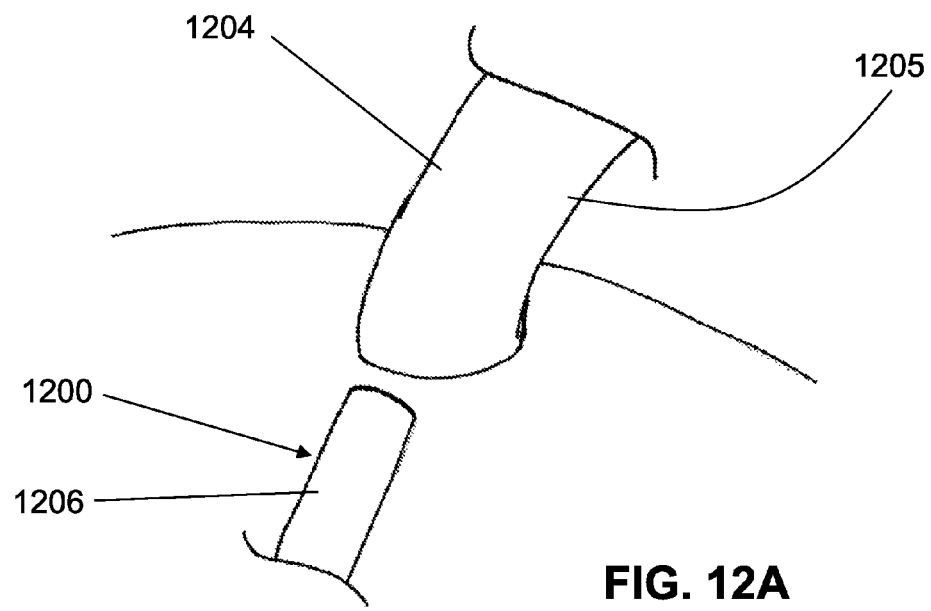
FIGS. 12A-12F illustrate variations of methods of placing a device around an anatomical structure.

Returning to the figures, cannula (1206) may be advanced to tissue structure (1204), as shown in FIG. 12A. Cannula (1206) may be advanced in any suitable manner. In some variations, cannula (1206) may be advanced over a guidewire (e.g., via one or more lumens of the cannula (1206). Additionally or alternatively, one or more portions of the cannula (1206) may be steerable. While shown in FIGS. 12A-12F as being a blood vessel (1205), tissue structure (1204) may be any suitable anatomical structure. In some variations, tissue structure (1204) may be the left atrial appendage. In other variations, the tissue structure (1204) may be the right atrial appendage.

Figure 12B:
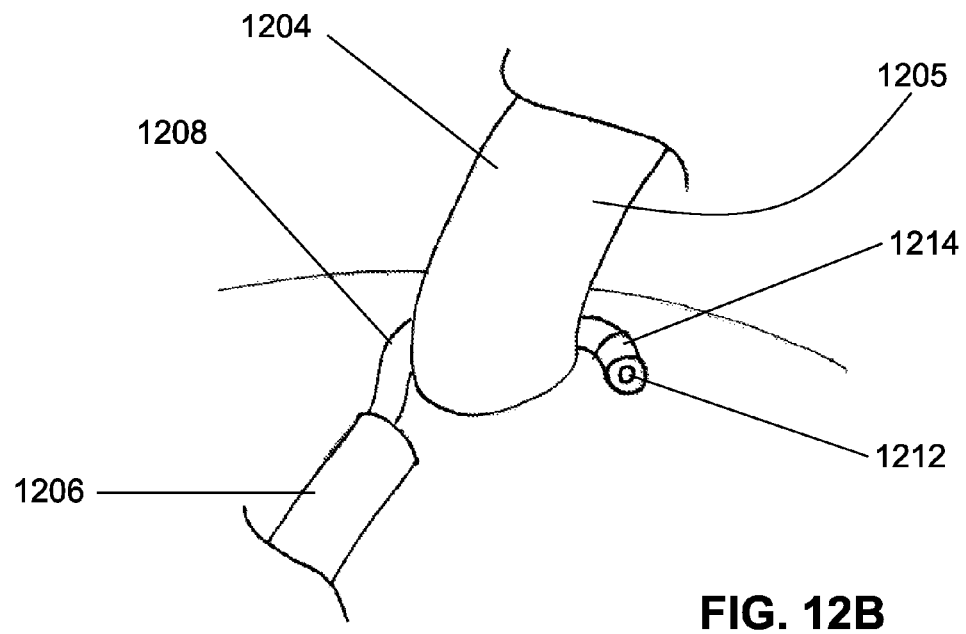

Once cannula (1206) is positioned at or near the tissue structure (1204), first guide (1208) may be advanced out of the distal end of cannula (1206), as shown in FIG. 12B. As first guide (1208) is advanced out of the distal end of cannula (1206), it may take on a curved configuration. In some variations, the first guide (1208) has a pre-shaped curved configuration, which may be constrained when it is housed within cannula (1206). In other variations, the first guide (1208) may be steered or otherwise actuated to take on the curved configuration. The first guide (1208) may be advanced such that a distal portion of the guide (1208) curves at least partially around the tissue structure (1204), as depicted in FIG. 12B.

Figure 12C:
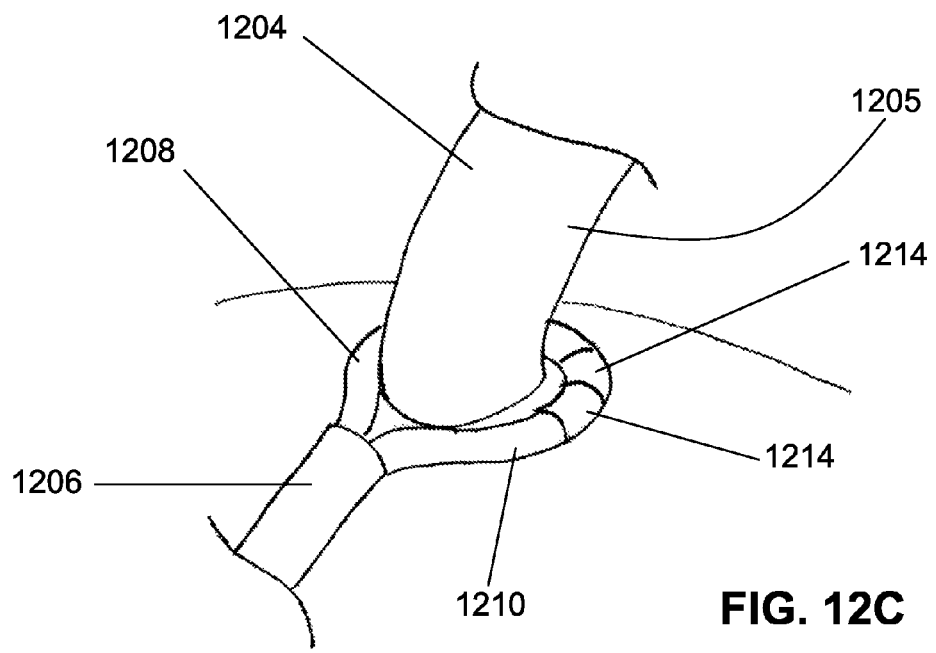

The second guide (1210) may then be advanced from the distal end of cannula (1206), as depicted in FIG. 12C. As shown there, the second guide (1210) may be advanced toward and may engage the first guide (1208). For example, in variations where the first (1208) and second (1210) guides each comprise a magnetic alignment element (1214), the magnetic alignment elements (1214) of the first (1208) and second (1210) guides may attract each other and hold the distal ends of the two guides in place relative to each other. In some variations, the distal ends of first (1208) and second (1210) guides may be positioned such that the lumens (1212) of the two guides are aligned. In some of these variations, the magnetic alignment elements (1214) of each of the first (1208) and second (1210) guides may hold the lumens (1212) of the two guides in alignment.

Figure 12D:
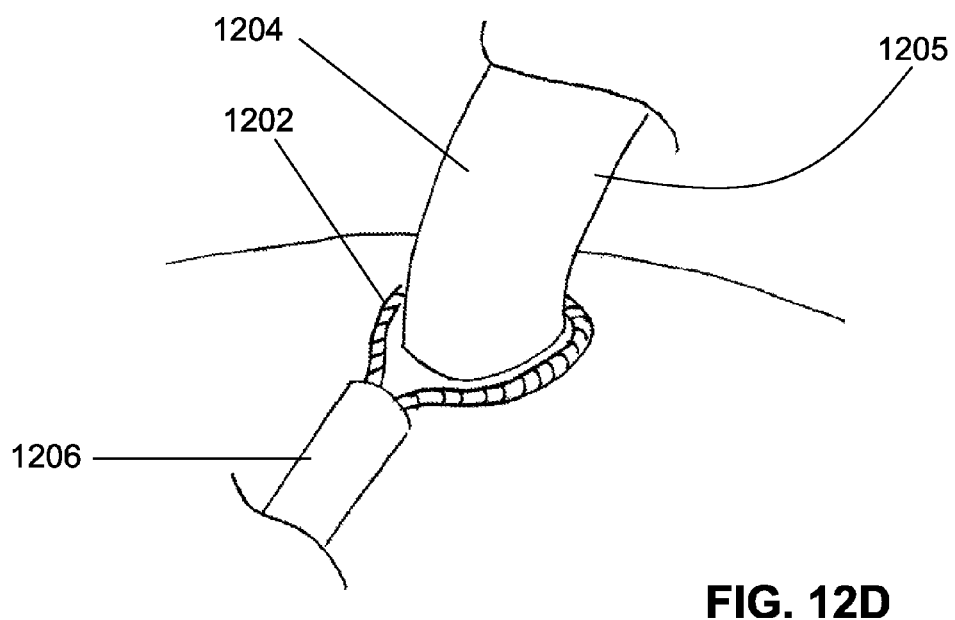

Once the lumens (1212) of the first (1208) and second (1210) guides are aligned, a guide element (1202) may be advanced through the lumen (1210) of first guide (1208) such that it exits the distal end of first guide (1208) and enters the lumen of the second guide (1210) (or vice versa). The guide element (1202) may then be advanced through the second guide (1210) (or the first guide (1208)) and the first (1208) and second (1210) guides may be withdrawn through the catheter, as shown in FIG. 12D. In some instances, this may position both ends (not shown) of the guide element (1202) may extend out from a proximal end of the cannula and/or may extend outside of the body. In these variations, guide element (1202) may be a wire, a suture, yarn, strand, or the like. While FIGS. 12A-12D depict advancing a guide element (1202) through lumens (1212) of the first (1208) and second (1210) guides, it should be appreciated that in some variations a tube or catheter may be advanced over the first (1208) and second (1210) guides to place the tube or catheter around the tissue structure (1204).

Figure 12E:
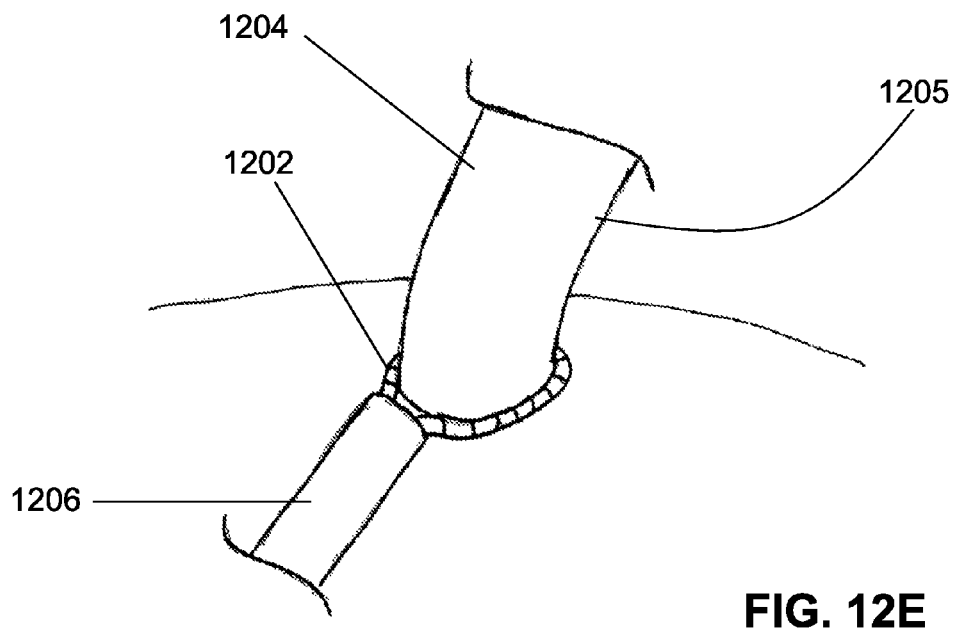
Figure 12F:
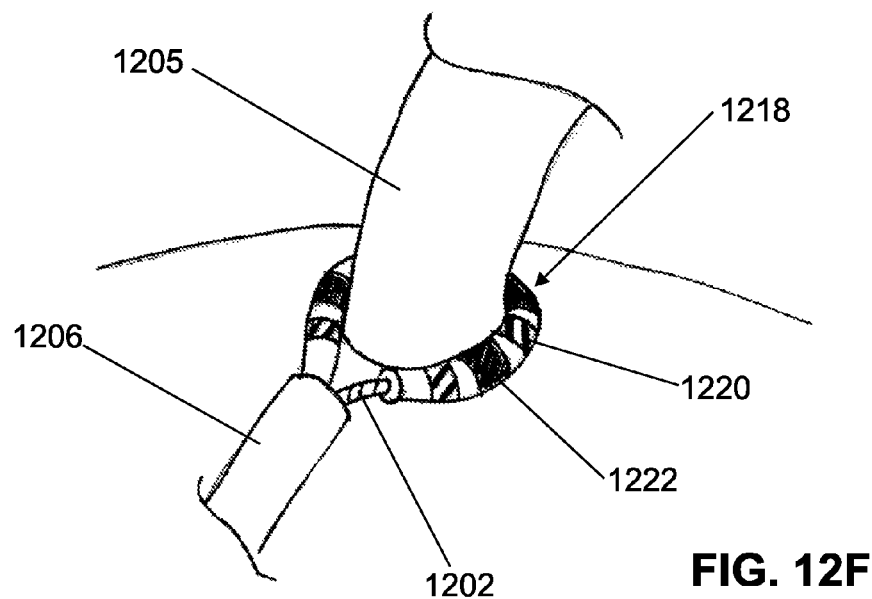

In some variations, the ends of the guide element (1202) may be pulled proximally to cinch the distal exposed portion of guide element (1202) (e.g., the portion of guide element extending from the distal end of cannula (1206)) around the tissue structure (1204), as shown in FIG. 12E. In variations where tissue structure (1204) is the left atrial appendage (not shown), cinching guide element (1202) around the left atrial appendage may act to close (temporarily or permanently). In variations where the left atrial appendage is used as an access port into the interior of the heart, as described hereinthroughout, guide element (1202) may be used to help provide hemostasis by temporarily closing the left atrial appendage around one or more devices placed through tissue of the left atrial appendage. For example, in some variations, a knot, clip, or clamping structure (not shown) may be advanced over a portion of the guide element (1202) to hold the guide element in place around the tissue structure (1204). In variations where the guide element (1202) is placed around the left atrial appendage, the guide element (1202) may be used to close the left atrial appendage (as described immediately above) and a knot, clip, or clamping structure may be advanced to hold the guide element (1202) in place such that the left atrial appendage is held in a closed configuration. In some variations, the guide element may comprise a releasable suture loop, where cinching the guide element around the tissue structure (1204) likewise cinches the suture loop around the tissue structure (1205). Once the desired level of tightening is achieved, the suture loop may be released from the guide element, and the guide element may be retracted proximally. To secure the tension in the suture loop, a knot, clip or other clamping structure may be advanced through the cannula to lock the suture loop. In these variations, a suture-cutter or the like may be advanced over a portion the guide element (1202) to sever at least a portion of the guide element (1202) (e.g., the portions of guide element located proximal to the knot, clip, or clamping structure.

Additionally or alternatively, one or more devices may be advanced over the guide element (1202) to place the device at least partially around the tissue structure (1204). For example, in some variations one or more ablation catheters may be advanced over the guide element, such as ablation catheter (1218) shown in FIG. 12F. As shown there ablation catheter (1218) may comprise one or more ablation elements (1220) (which may be used to deliver ablation energy to nearby tissue) and one or more magnetic elements (1222) (which may help align ablation catheter (1218) with one or more additional components). Indeed, access device (1200) may be used to place any of the devices described in U.S. Provisional Patent Application No. 61/323,796, filed on Apr. 13, 2010 and titled "METHODS AND DEVICES FOR TREATING ATRIAL FIBRILLATION", which was previously incorporated by reference, and U.S. patent application Ser. No. 13/086,389, filed on Apr. 13, 2011, titled "Methods and Devices for Treating Atrial Fibrillation" which is hereby incorporated by reference in its entirety. Additionally or alternatively, access device (1200) may be used to place any suitable device or devices around a tissue structure (e.g., one or more measurement catheters or the like)

C. Devices and Method for Pericardial Device Delivery to a Heart Via the Left Atrial Appendage Once access to the heart via the left atrial appendage has been obtained (e.g., by one of the devices or methods described hereinthroughout) one or more treatment devices may be delivered to the heart via the left atrial appendage access site. In some variations, additional devices may be used, for example, to help stabilize the left atrial appendage, which may be useful in a beating heart procedure. Stabilizing the left atrial appendage may help improve the precision and reliability of device delivery, which may help improve the consistency of heart procedures. Stabilizing the left atrial appendage may also help to reduce the duration of the procedures. Examples of devices that may be used to stabilize and/or secure the left atrial appendage are described in U.S. patent application Ser. No. 12/055,213, filed on Mar. 25, 2008, U.S. Provisional Patent Application No. 61/323, 796, filed on Apr. 13, 2010 and titled "METHODS AND DEVICES FOR TREATING ATRIAL FIBRILLATION, as well as U.S. patent application Ser. No. 13/086,389, filed on Apr. 13, 2011, titled "Methods and Devices for Treating Atrial Fibrillation", each of which have been previously incorporated by reference in their entirety. Also, some methods described below approach and access the heart via the pericardial space, e.g., from the chest cavity. Devices and methods for accessing the pericardial space have been described in U.S. Provisional Patent Application Ser. No. 61/323,801, filed on Apr. 13, 2010, and titled "METHODS AND DEVICES FOR PERICARDIAL ACCESS", and U.S. patent application Ser. No. 13/086,328 entitled "Methods and Devices for Pericardial Access," filed Apr. 13, 2011, each of which was previously incorporated by reference. In some procedures, using the left atrial appendage as an access and/or delivery port may be desirable, since closing and/or occluding and/or excluding the left atrial appendage may involve fewer steps and take less time than closing an access site by conventional methods, e.g., suture stitches. Additionally, using the left atrial access as a port may allow for the introduction of devices into the heart that may be difficult to advance intravascularly (e.g., may be too large and/or too inflexible for intravascular delivery). Some procedures may include closing the left atrial appendage access site at the conclusion of a procedure by occluding or closing the left atrial appendage (e.g., at the anatomical ostium).

Figure 7A:
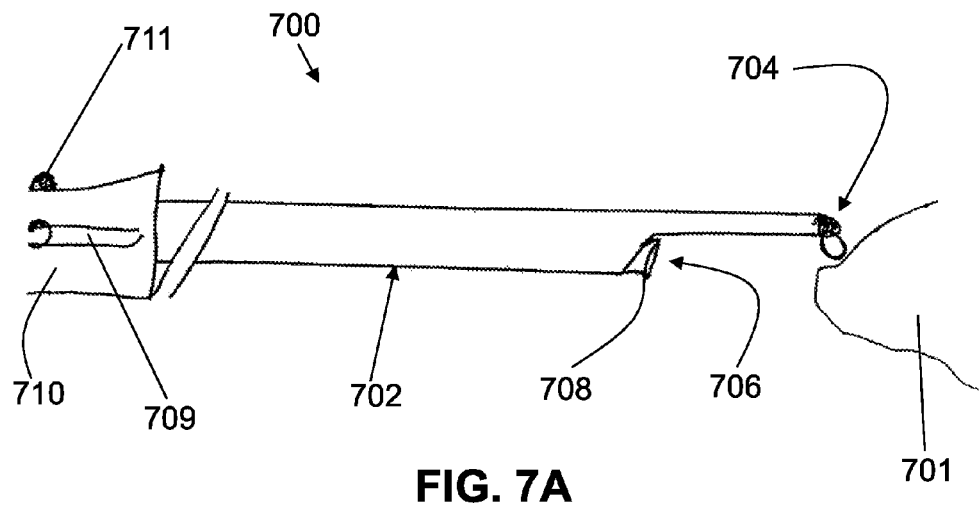
FIGS. 7A-7I depict one variation of a device and method for accessing and delivering devices to a heart using an access port through a left atrial appendage.
Figure 7B:
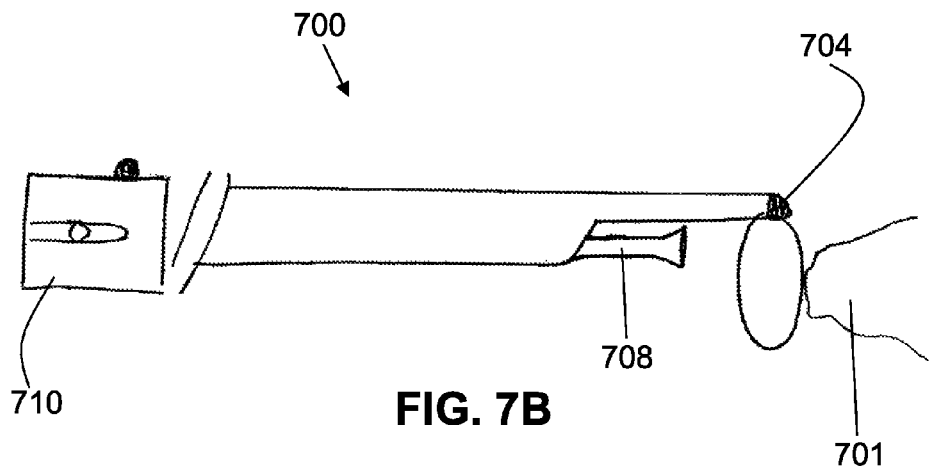
Figure 7C:
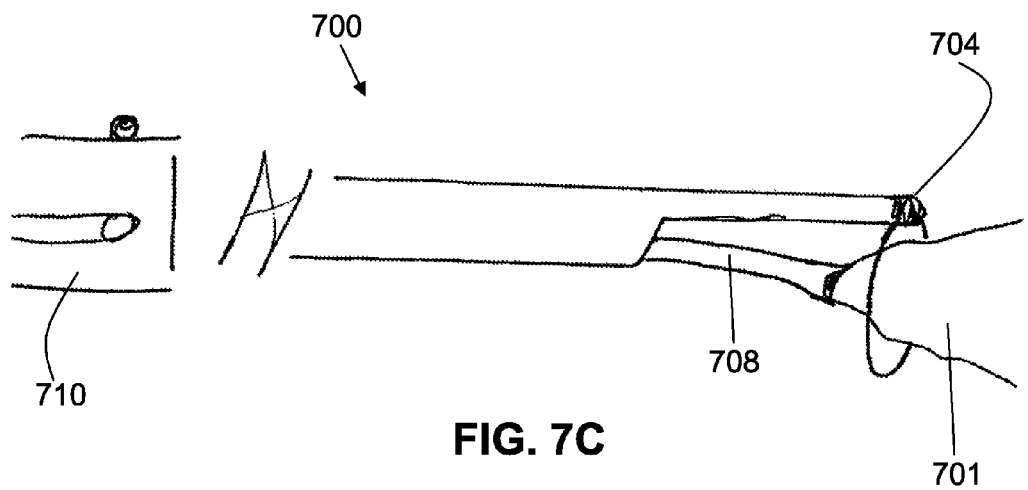

One variation of a method that may be used for pericardial access and device delivery to a heart via the left atrial appendage is shown in FIGS. 7A-7I. The method depicted there may be used with or without an intravascular access and/or alignment element. As depicted in FIGS. 7A-7C, a stabilization device may be advanced to the left atrial appendage, and may be used to help position and stabilize the left atrial appendage. Specifically, FIGS. 7A-7C illustrate a variation of the device (700), which may comprise an elongate body (702) having a proximal end and a distal end, and a lumen (706) therethrough. The device (700) may also comprise a closure element (704). In this variation, the closure element comprises a loop that defines a continuous aperture therethrough suitable for stabilizing and/or encircling the left atrial appendage therein. The closure element may temporarily or permanently close the left atrial appendage, as will be described in more detail below. The closure element may be at least partially housed within the elongate body (702) and may be expanded therefrom, or retracted therein. The lumen (706) may be configured for the passage of tools or fluids therethrough. For example, the lumen (706) may provide for the passage of a guide element (with or without an alignment member), a guidewire, a tissue-access device, a suture cutter, fluids and/or drugs, and the like. In the variation of device (700) shown in FIG. 7A, a vacuum device (708) may be enclosed in the lumen (706), where the vacuum device may be used to help stabilize and/or restrict the movement of the left atrial appendage, especially during a beating heart procedure. Any number of lumens may be provided for any suitable purpose. Examples and variations of lumens will be described below. The device (700) may also comprise a handle (710) having a slide actuator (709) and a knob (711). Any number and type of actuation mechanisms may be included in the handle (710) as needed for controlling the use of the device (700). Other variations of devices comprising closure elements that may be used to access and stabilize the left atrial appendage are described in U.S. patent application Ser. No. 12/055,213, filed on Mar. 25, 2008, which was previously incorporated by reference in its entirety.

In the variation shown in FIG. 7A, the elongate body (702) is relatively straight, but in other variations, may comprise one or more curves along the length thereof. The one or more curves may be pre-shaped, or may be formed by a flexing or bending mechanism. The elongate body may be flexible or rigid, or may be made of several portions, where some portions are flexible and others are rigid. In some variations, the elongate body may be steerable or articulatable, for instance, by including actuating mandrel(s), hinges, joints, and the like, which may aid in device delivery and stabilizing the left atrial appendage. In certain variations, the elongate body may be straight and flexible, and have a pull-wire attached thereto, so that when the pull-wire is pulled proximally, the elongate body flexes and bends. In variations where the elongate body of the device comprises one or more pre-shaped curves, a straightening tube, or other straightening mandrel or mechanism may be used to temporarily straighten the elongate body while it is being advanced towards the heart. The straightening tube or mandrel may then be withdrawn to allow the elongate body to assume its curved shape. The straightening tube may be made of any suitable material (e.g., a rigid plastic, stainless, combination thereof, etc.). It should be understood that any of the devices described herein may be configured to improve steerability, or may be configured for robotic use (e.g., configured for use with one or more robotic or other automated type device).

The lumen (706) of the elongate body (702) may extend through at least a length therethrough. In some variations, the elongate body lumen may extend through the entire length of the elongate body. The lumen (706) may be used for any suitable purpose. For example, it may be used to enable passage of one or more guides or guidewires therethrough (or for stabilization device (700) to be advanced along one or more guides or guidewires via lumen (706), one or more tools therethrough, or the like. The lumen may also be used as a flush lumen, a vacuum lumen, a drug or chemical agent delivery lumen, gas delivery lumen, contrast agent delivery lumen, or the like. The elongate body may comprise any number of lumens, and it should be understood that the lumens need not traverse the entire length of the elongate body, nor form a completely bounded aperture (i.e., the use of lumens herein is intended to capture instances where a slit or groove may be used with one or more guides, guidewires, or additional tools). Certain variations of elongate body lumens may have one or more side slots or apertures. In some variations, the elongate body lumen may have a partially-open geometry, e.g., have a C-shaped cross-section, or may have a longitudinal side aperture that extends at least a longitudinal portion of the lumen. The elongate body lumens associated with the device (700) may be formed by any suitable method. For example, the elongate body may be made from a tube with one or more longitudinal lumens therethrough, e.g., a hypotube, or any suitable tubular structure, where the one or more longitudinal lumens are formed in the course of manufacturing the tube. Any number or configuration of longitudinal lumens may be associated with the device (700) as needed for accessing and delivering devices to the heart.

The closure element (704) of the device (700) may also comprise a suture loop (705) (see FIG. 7H) that may be releasably connected to the closure element (704) (e.g., by a dual-lumen connecting member, or the like). The closure (704) and suture loop (705) which may have any appropriate length perimeter. For example, the suture loop (705) and/or closure element (704) may have a perimeter of 4.5 inches in a fully expanded state, a perimeter of about 4.3 in, about, 3.3 in, about 4.0 in, about 3.5 in, about 3.3 in, 3.0 in, about 2.7 in, about 2.5 in, about 1.5 in, about 1.25 in, or the like. Of course, these perimeters will vary as the closure element and suture loop are actuated and retracted.

The above described components may be made of any suitable material(s). For example, the closure element may be made from a shape-memory material, such as a shape-memory alloy (e.g., nickel titanium alloy, etc.), may be made from stainless steel, polyester, nylon, polyethylene, polypropylene, some combination thereof, etc. Similarly, the suture loop may be made of any suitable material useful in exclusion or closure. For example, it may be made of a biodegradable material (e.g., polylactic acid, polyglycolic acid, polylactic-co-glycolic acid, etc.), or may be made of a non-biodegradable material (e.g., metal, steel, polyester, nylon, propylene, silk, and combinations thereof). In some variations, as will be described in more detail below, the suture loop may be made from a biodegradable material such that the suture loop degrades after a period of time has elapsed (e.g., for sufficient scarring to be achieved). It should be understood, the any part of the device may comprise, include, or be made from a radio-opaque or echogenic material to help facilitate visualization. For example, the closure element, the suture loop, the elongate body, or any combination of these components may comprise a radio-opaque or echogenic material. Additional details and descriptions of device (700) are provided in U.S. Provisional Patent Application No. 61/323,796, filed on Apr. 13, 2010 and titled "METHODS AND DEVICES FOR TREATING ATRIAL FIBRILLATION and U.S. patent application Ser. No. 13/086,389, filed on Apr. 13, 2011, titled "Methods and Devices for Treating Atrial Fibrillation" each which has been previously incorporated by reference in its entirety.

Figure 7D:
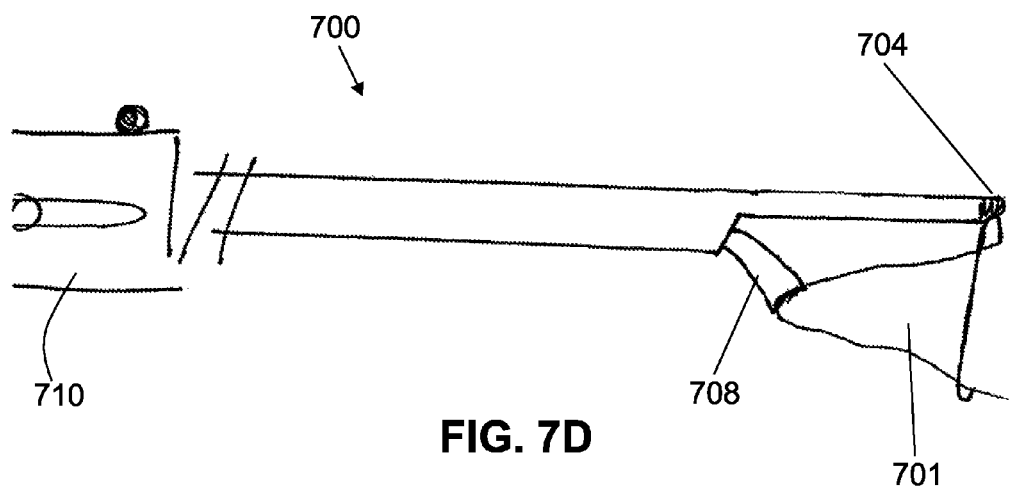

Making reference now to the figures, FIGS. 7B-7H show the device (700) being advanced adjacent to the left atrial appendage (701) from outside of the heart. The device (700) may be advanced in any suitable fashion. For example, it may be advanced via a subthoracic approach, or via intercostal or intracostal access, via open surgical access, or the like. In some variations, device (700) may be advanced over one or more guidewires or through one or more sheaths. The closure element (704) may be advanced towards the left atrial appendage (701) and expanded, as depicted in FIG. 7B. The closure element (704) may then be advanced over the left atrial appendage (701) to encircle the left atrial appendage. In variations where the device (700) comprises a vacuum tissue-access device (708), the vacuum tissue-access device (708) may also be advanced and activated to secure the left atrial appendage. FIGS. 7C and 7D depict the passage of the closure element (704) over the left atrial appendage (701) with the aid of negative pressure applied to the left atrial appendage via the vacuum device (708).

Figure 7E:
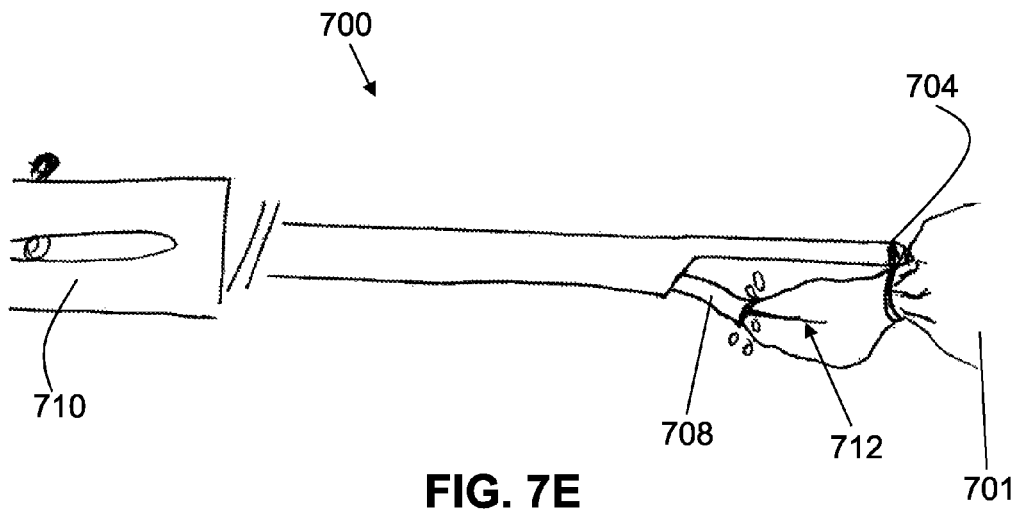

When in place around the left atrial appendage (701), the closure element (704) may be tightened around the left atrial appendage (701). In some variations, this may act to further stabilize the left atrial appendage. The closure element (704) may additionally help to maintain hemostasis after puncture of the left atrial appendage, by restricting the blood flow from the heart into the left atrial appendage. The device (700) may be further configured to puncture or otherwise pierce the left atrial appendage to obtain access to the interior of the left atrial appendage. In some variations, the device (700) may comprise a blade or piercing member, which may be advanced through the lumen (706). For example, as shown in FIG. 7E, a guide element (712) with a piercing distal end that may be used to puncture the left atrial appendage, and may be advanced through the lumen (706) of the device (700). The guide element (712) may act as a guide for other devices to access the left atrial appendage, as will be described in more detail below. In some variations, an access site or port through the wall of the left atrial appendage may be formed by using chemicals such as enzymes, current or voltage pulses, RF pulses, electrocautery, chemical cautery, laser cautery, and the like. The access site or port may also be enlarged, for example, using a series of dilators. In some variations, hemostasis devices may be installed at the access site or port to reduce bleeding. Hemostasis devices that may be used include one-way valves, such as check or non-return valves, fibrin seals and the like. In some variations, a piercing element and guide element may be separate devices that are deployed sequentially.

Figure 7F:
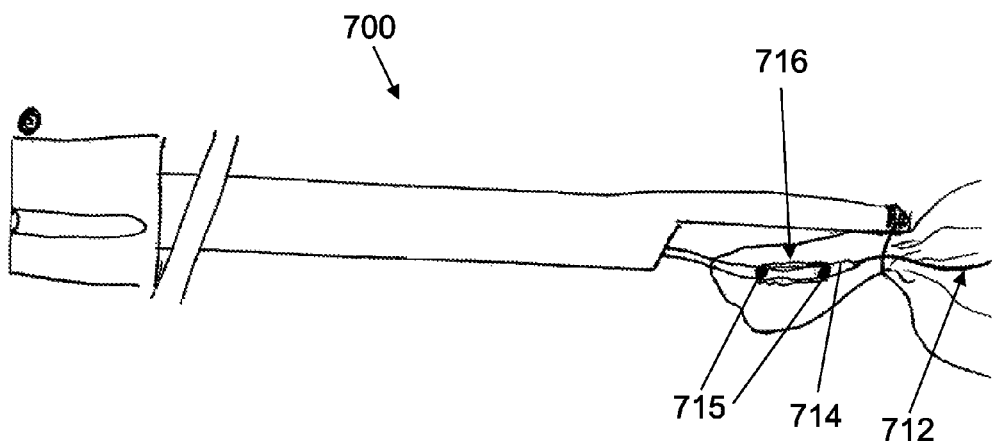
Figure 7G:
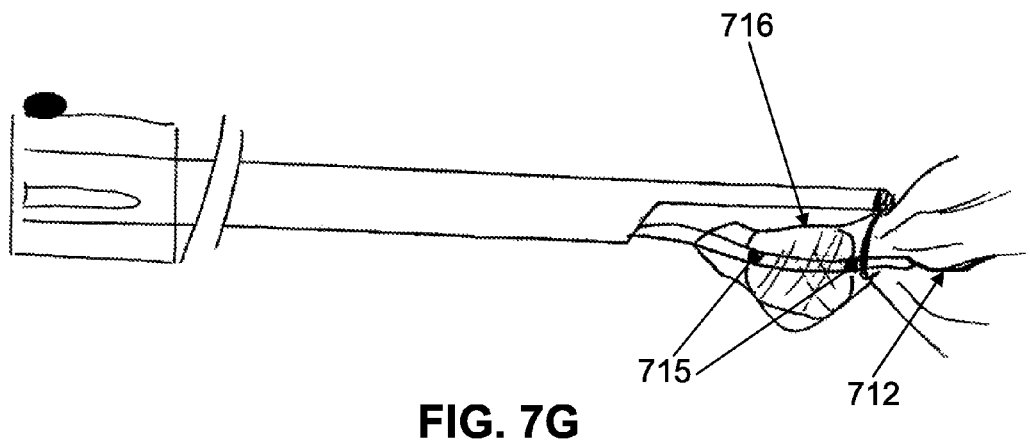

Once access to the inside of the appendage has been established, other tissue-affecting devices may be introduced to the left atrial appendage, as well as other internal structures of the heart. Advancing the guide element (712) further past the left atrial appendage may allow the delivery of a treatment device to one or more areas of the heart (e.g., the left atrium, left ventricle, and/or the mitral valve). The guide element may be navigated to contact nearby vascular structures (e.g., atrioventricular valves, semilunar valves, chordae tendinae, papillary muscles, etc.). Additionally or alternatively, the guide element may be introduced to the right side of the heart, e.g., the right atrium, right ventricle, etc., by using, for example, a transseptal technique. Once the guide element is positioned at a desired anatomical location, devices may be advanced over the guide element to that location. Similar devices and methods may be used to access various structures and regions of the heart by entering through the right atrial appendage, or any other desired region of the heart. Examples of tissue-affecting devices that may be introduced to the left atrial appendage include various tissue ablation devices and/or devices that chemically and/or physically manipulate the tissue (e.g., excise, grasp, pinch, extract, etc). For instance, tissue-affecting devices may comprise an expandable member (e.g., a balloon) may stretch the tissue, and/or may occlude a portion of the tissue, while other tissue-affecting devices may comprise graspers and/or cutters may secure and/or create an incision in the tissue. In some variations, a tissue-affecting device may manipulate and position the tissue in preparation for other tissue-affecting devices, such as closure devices, or other devices as described previously. Tissue-affecting devices may vary depending on the nature of the heart disease to be treated, for example, devices for the treatment of valve disease, atrial fibrillation, patent foramen ovale, as well as pacemakers and/or electrodes. The tissue-affecting device may be introduced into the left atrial appendage (701) by advancing a catheter (714) over the guide element (712). FIG. 7F shows a tissue-affecting device (716) in a collapsed configuration that is advanced into the left atrial appendage (701) using a catheter. The tissue-affecting device (716) may be implantable, and/or may be withdrawn once the desired effect on the tissue is achieved. One or more imaging markers (715), such as radio-opaque, echogenic markers, may be included on catheter (714) and/or tissue-affecting device (716), so that their position may be monitored and determined by any suitable imaging modality. The tissue-affecting device (716) may be expanded within the left atrial appendage as illustrated in FIG. 7G by using a liquid or gas, or may stretch the tissue of the left atrial appendage by enlarging a structural scaffold (e.g., by the use of hinged joints). The tissue-affecting device may help to prepare for the deployment and operation of additional devices.

In variations when one or more devices are advanced through the left atrial appendage and into the interior of the heart, closure element (704) of device (700) may be used to help maintain hemostasis. As mentioned above, closure element (704) may be used to close or otherwise cinch the left atrial appendage to help prevent blood flow from the left atrium into the left atrial appendage. When a guide element, treatment device, or the like, is advanced into the left atrial appendage, the closure element (704) may be temporarily opened to allow the device to pass from the left atrial appendage into the left atrium, at which point the closure element (704) may be re-closed to close the left atrial appendage around the device. This procedure may be repeated to maintain hemostasis as devices are advanced into or withdrawn from the left atrial appendage access site.

Figure 7H:
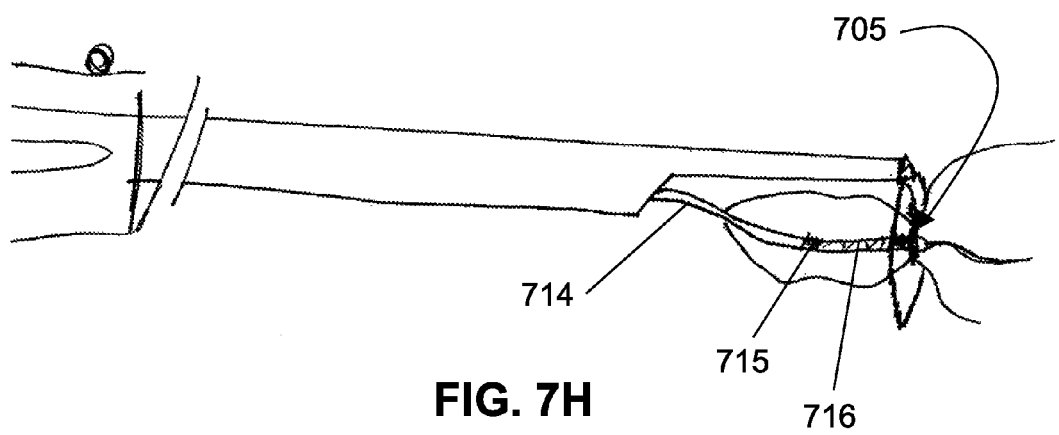
Figure 7I:
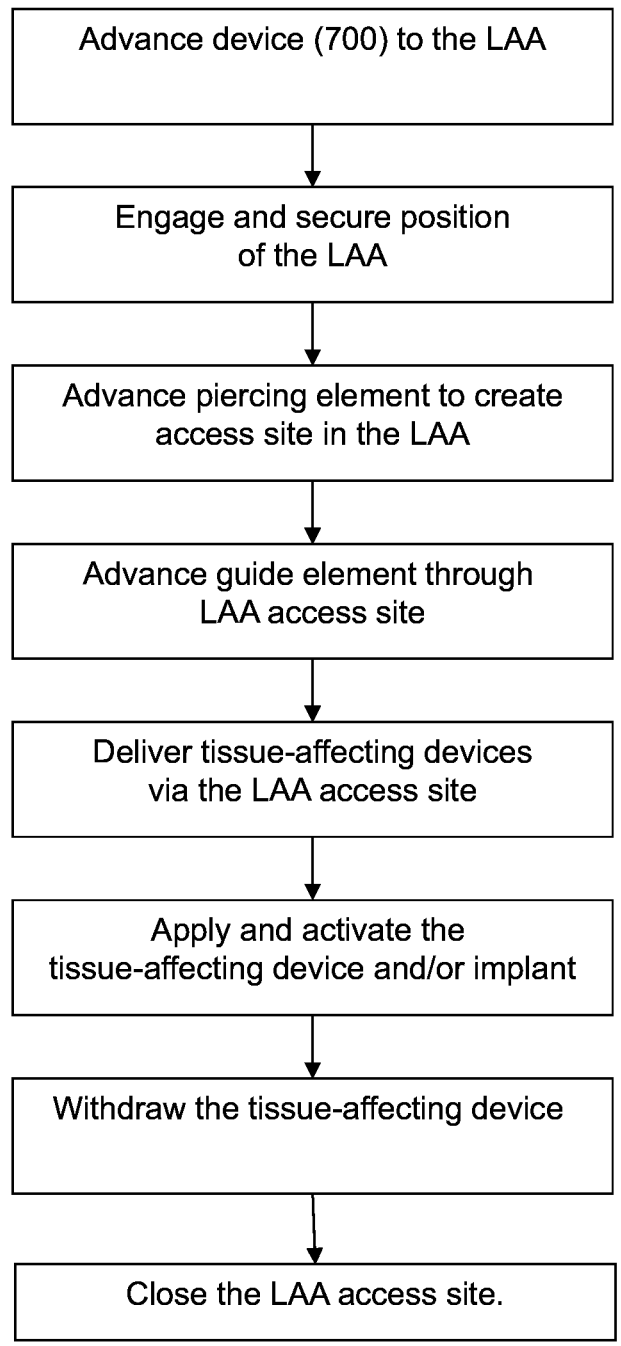

Once the desired tissue effect has been attained, the access site or port through the left atrial appendage may be closed. Prior to closing the left atrial appendage access site, the tissue-affecting device may be withdrawn. One example of how the left atrial appendage access site may be closed is depicted in FIG. 7H. As shown there, the tissue-affecting device (716) may be reverted to its collapsed state, and the device (700) may be withdrawn proximally. In other variations, the tissue-affecting device (716) may be implantable, and may remain in the left atrial appendage (701). The closure element (704) may be tightened so that the left atrial appendage may be closed off, which may be confirmed with the visualization techniques described previously. The suture loop (705) may be deployed or otherwise release from closure element (704) to fix the left atrial appendage in a closed position. The suture loop (705) may be de-coupled from the device (700) using any of the techniques described in detail in U.S. patent application Ser. No. 12/055,213, filed on Mar. 25, 2008, which was previously incorporated by reference in its entirety. These steps are summarized in a flowchart depicted in FIG. 7I. Each step of the method shown in FIG. 7I may be followed with a confirmation and/or verification step, as appropriate (e.g., verification by tactile feedback, imaging data, physiological data, and the like). Some steps may be performed sequentially or simultaneously. It should be understood that the access site of the left atrial appendage may be closed without closing the left atrial appendage at the anatomical ostium. While the method depicted in FIGS. 7A-7I comprises closing the access site by closing the left atrial appendage at the anatomical ostium, a similar method may be used where the access site is closed by suturing, fibrin glue, or any other suitable method, at a location other than the anatomical ostium of the left atrial appendage.

Figure 8A:
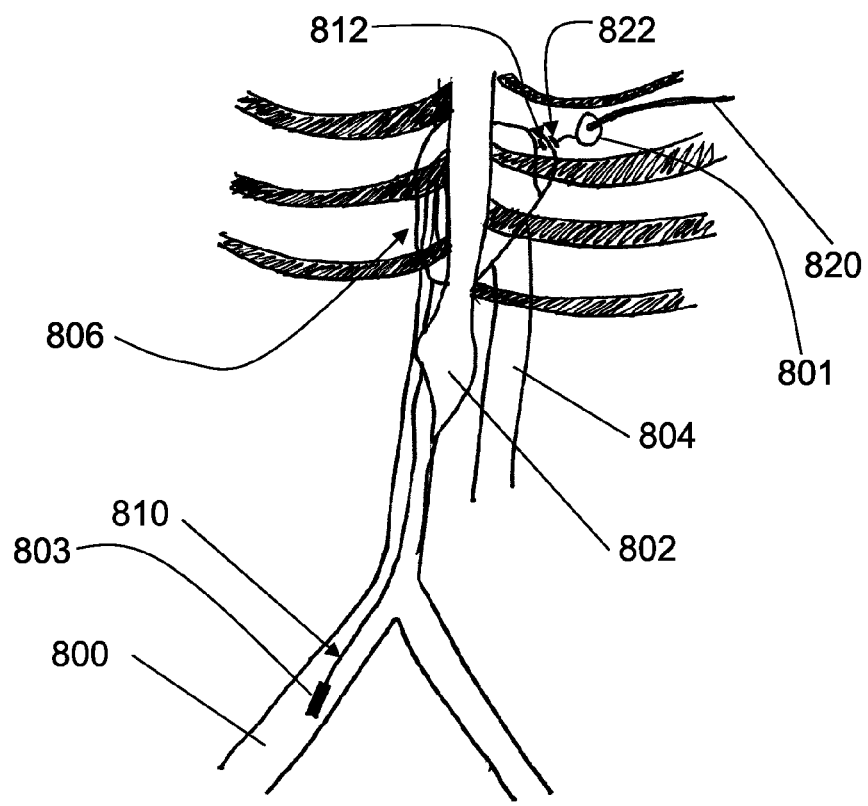
FIGS. 8A-8K depict another variation of a device and method for accessing and delivering devices to the heart via an access port through a left atrial appendage.

D. Devices and Methods for Intravascular Delivery and Pericardial Access Via the Left Atrial Appendage In addition to providing a port or access site at the left atrial appendage, the devices described herein may also be used to assist in the positioning and operation of devices within the heart. One variation of a method where an access site at a left atrial appendage may assist in the intravascular delivery and positioning of a device in the left atrial appendage is depicted in FIGS. 8A-8K. A first access element (810) may be positioned in the heart via an intravascular approach, as shown in FIG. 8A. For example, access may be obtained via one or several of the various veins or arteries (e.g., jugular, femoral, carotid, etc.). In some variations, internal structures of the heart may be intravascularly accessed on the inside via the common femoral vein, such as access site (803) on the right common femoral vein (800) shown in FIG. 8A using a standard Seldinger technique with a needle. Alternatively, the heart may be accessed retrograde direction through the aorta (804). An introducer wire may then be advanced through the needle, followed by a first access element (810). The introducer wire may then be removed. The first access element (810) may be a guide catheter sheath, an introducer sheath, or any device that is flexible and atraumatic which may be navigated through the femoral vein (800), into the heart (806). The first access element (810) may be positioned at a desired location in the heart, which may be monitored by imaging. For example, using fluoroscopy, an angiogram may be performed through the first access element (810) to observe anatomical characteristics, as well as to evaluate the suitability of the access route for the purpose of transseptal access into the left atrium (e.g., tortuosity, clots, devices, such as vena cava filters, etc.). Alternatively or additionally, an angiogram may be performed through a catheter placed through a sheath, or a guide catheter sheath, or any combination thereof. Fluoroscopy, ultrasound, intracardiac echocardiography, extracardiac echocardiography, transesophageal echocardiography, or combinations thereof, may be used to help visualize transseptal access to the left atrium, and access to the left atrium may be obtained using standard transseptal access techniques. The distal portion of the first access element (810) may comprise a first alignment member (812), which may be, for example, magnetic.

A second access element (820) may be positioned from an epicardial approach, for example, using a subthoracic access point (801). The access point (801) is typically identified based on patient anatomic characteristics. In some variations, the access point (801) is left of a xiphoid process (802) and pointed towards the patient's left shoulder, but may be at any suitable location. FIG. 8A depicts intercostal access via a thoracostomy, but such access may also be acquired via a sternotomy, a thoracotomy, or through costal cartilage itself. Once the access point (801) has been determined, a needle (e.g., a 17G Tuohy needle) may be advanced using standard pericardiocentsesis techniques under fluoroscopic guidance. After access to the pericardium has been obtained, the second access element (820) comprising a second alignment member (822) at the distal portion may be advanced through the needle under fluoroscopic visualization within the pericardial space. The needle may then be removed once it has been confirmed that access to the pericardial space has thus been obtained. Other devices and methods for accessing the pericardial space may also be used, and are described in U.S. Provisional Patent Application Ser. No. 61/323,801, filed on Apr. 13, 2010, and titled "METHODS AND DEVICES FOR PERICARDIAL ACCESS", and U.S. patent application Ser. No. 13/086,328, filed on Apr. 13, 2011, titled "Methods and Devices for Pericardial Access" each which has been previously incorporated by reference in its entirety.

Figure 8B:
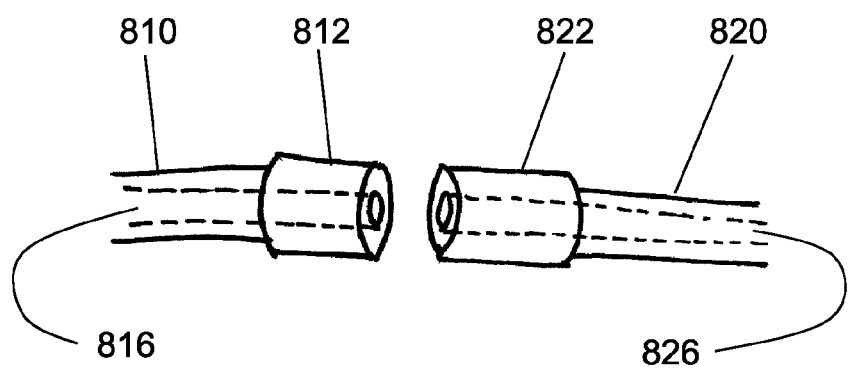

FIG. 8B depicts a closer view of the first and second access elements from FIG. 8A. The first and second access elements (810, 820) may each comprise a longitudinal lumen (816, 826) therethrough, where the lumens (816, 826) extend through the alignment members (812, 822). When the alignment members (812, 822) are matched, the lumen (816) may also be matched with the lumen (826) and attached through the tissue generally at or along their ends, or any other suitable configuration as previously described. This configuration may allow a device to be transferred from the lumen of the first access element (810) to the lumen of the second access element (820). For example, when the lumens (816, 826) are appropriately aligned, fluids, imaging contrast agents, guide elements, sutures, and the like may be directly passed from the first access device to the second access device. Any suitable alignment members that facilitate attachment and/or communication through the tissue may be used here. In other variations, the alignment members may position the access elements in a non-linear configuration, for example, the alignment members may position the access elements at an angle, or perpendicularly to with respect to each other. Additional variations of alignment members have been previously described. The alignment members may also be attached such that hemostasis is maintained.

Figure 8C:
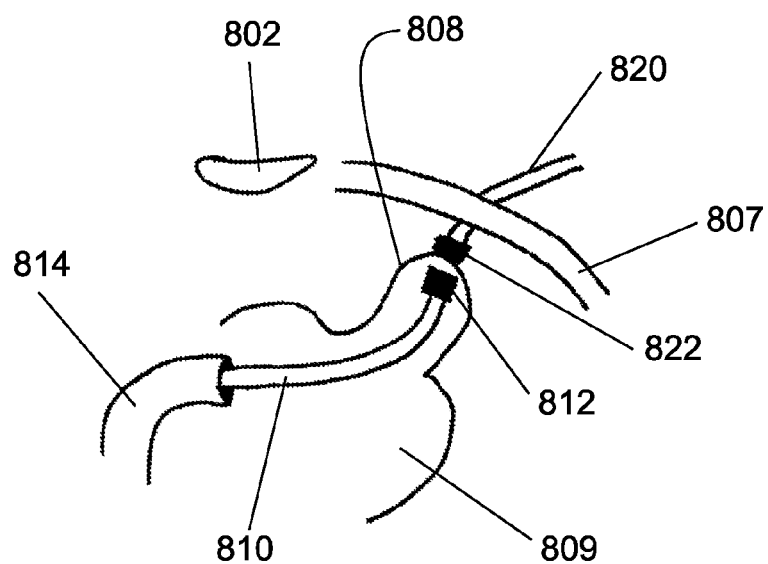
Figure 8D:
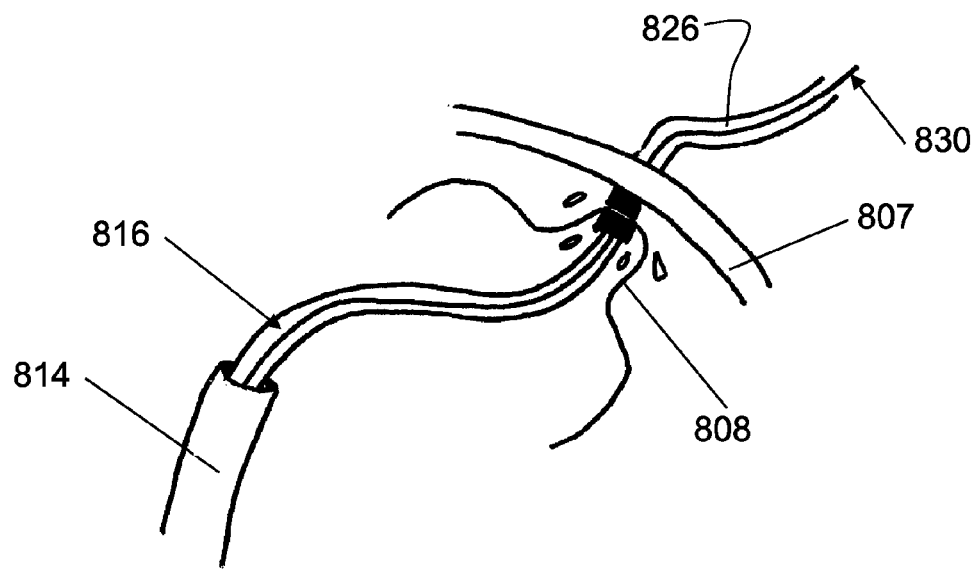
Figure 8E:
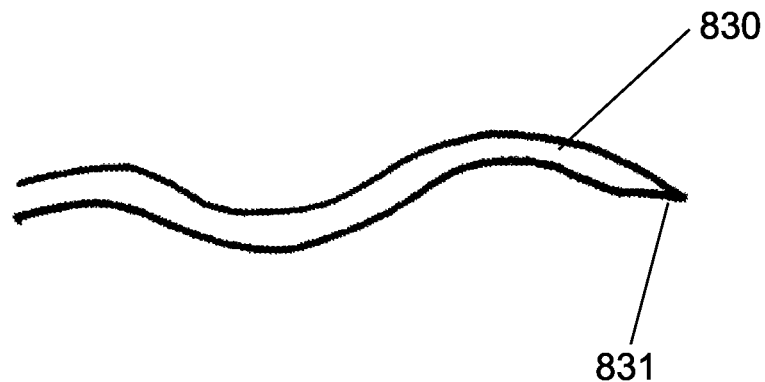

FIGS. 8C and 8D depict the approach of the first and second access elements (810, 820) towards each other. The first access element (810) and first alignment member (812) may be navigated to the left atrial appendage (808) using a transseptal approach, or may be advanced in a retrograde direction from the aorta via a guide catheter (814) into the left ventricle, then into the left atrium (809). Other guide elements, such as guidewires or rails, may be used, and in some variations, a second guide catheter or element may be included as may be appropriate. The second access element (820) and the second alignment member (822) may cross the pericardium (807), and be advanced towards the external side of the left atrial appendage (808). In some variations, the second access element (820) and the second alignment member (822) may be advanced over a guide element, as appropriate. When the first and second alignment members are matched, e.g., by magnetic attraction, the lumens (816, 826) may be aligned in any suitable configuration as previously described. For example, the lumens may be aligned generally at or along their ends, as shown in FIG. 8D. A piercing wire (830) may be advanced from one access element (either the first or second access element) to the other. The piercing wire (830) may be made from metallic materials, such as nickel titanium alloy, stainless steel, and the like, and may have a diameter of about 0.005 mm to about 5 mm and any suitable length. As the piercing wire (830) is advanced from one access element, it pierces through the wall of the left atrial appendage (808) and creates an access site as it enters the other access element. FIG. 8E depicts a closer view of the piercing wire (830), showing the tissue-piercing tip (831) at one end of the piercing wire. Other devices that may be used to create an access site or port through the wall of the left atrial appendage may include devices that use chemicals such as enzymes, current or voltage pulses, RF pulses, electrocautery, chemical cautery, laser cautery, and the like.

Figure 8F:
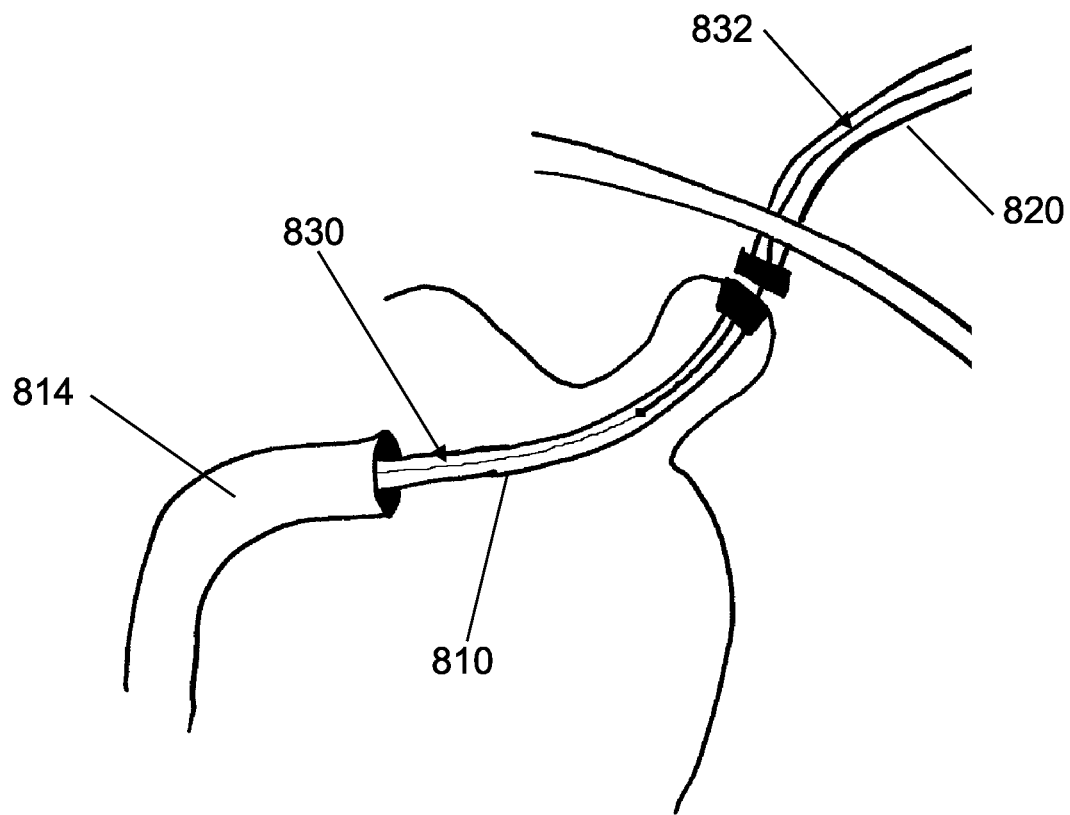

In the variation depicted here, the other end (i.e., opposite the tissue-piercing tip (831)) of the piercing wire (830) is attached to an exchange wire (832). The exchange wire (832) may be, for example, a standard guide wire. As the piercing wire (830) is advanced further, the exchange wire (832) may be pulled through one access element to the other access element, as shown in FIG. 8F. Once the exchange wire (832) is in place, the piercing wire (830) may be removed. Optionally, the access elements may be withdrawn after the exchange wire (832) is in place. The exchange wire (832) may further stabilize the interaction between first and second alignment members so that they may remain in matched alignment. Such additional stabilization may be desired for the delivery of devices to a beating heart. The exchange wire (832) may also guide the delivery of any tissue-affecting devices to the heart, either from an intravascular approach or from an epicardial approach. Alternatively or additionally, the exchange wire may help position and operate intravascular devices. In other variations, the piercing element may not be coupled with an exchange element, where the piercing element may be withdrawn after it pierces the left atrial appendage, and then the exchange element is subsequently advanced.

Figure 8G:
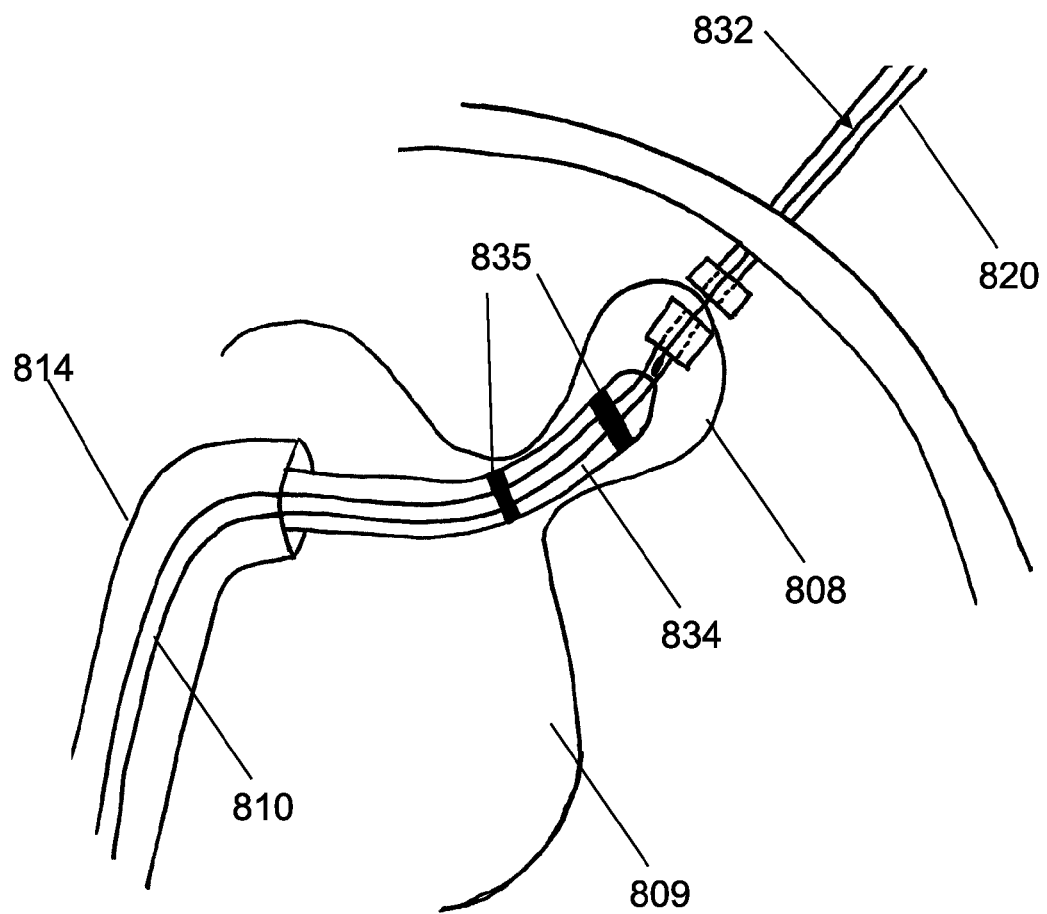
Figure 8H:
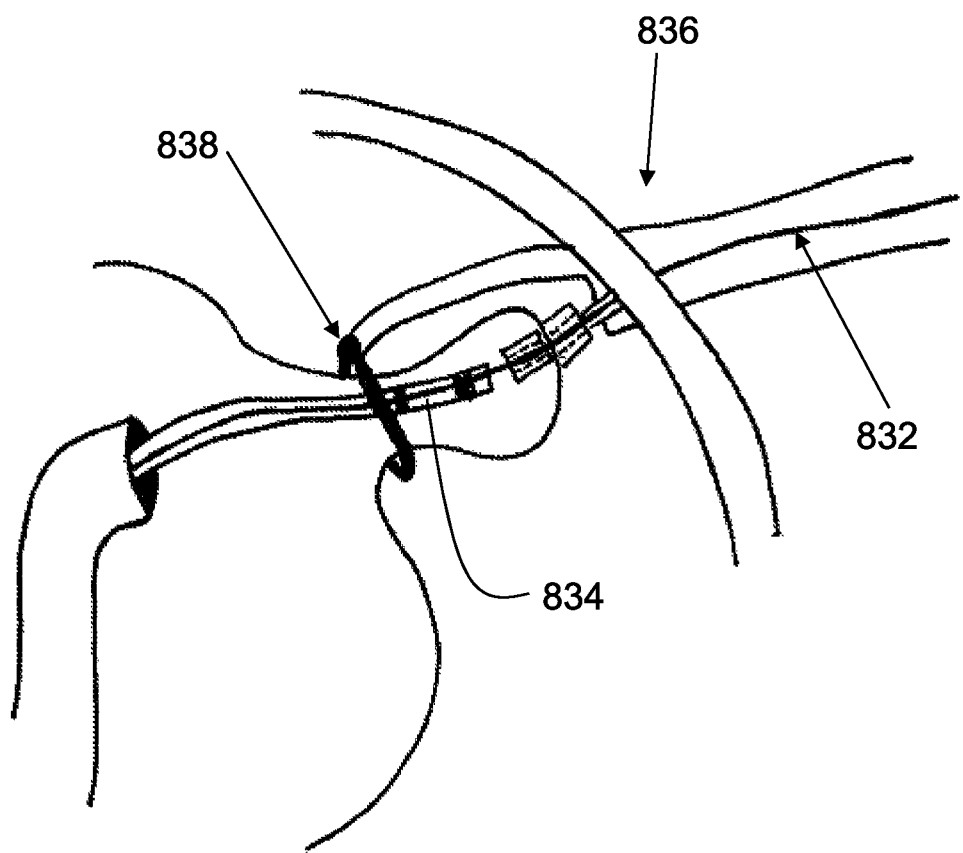
Figure 8I:
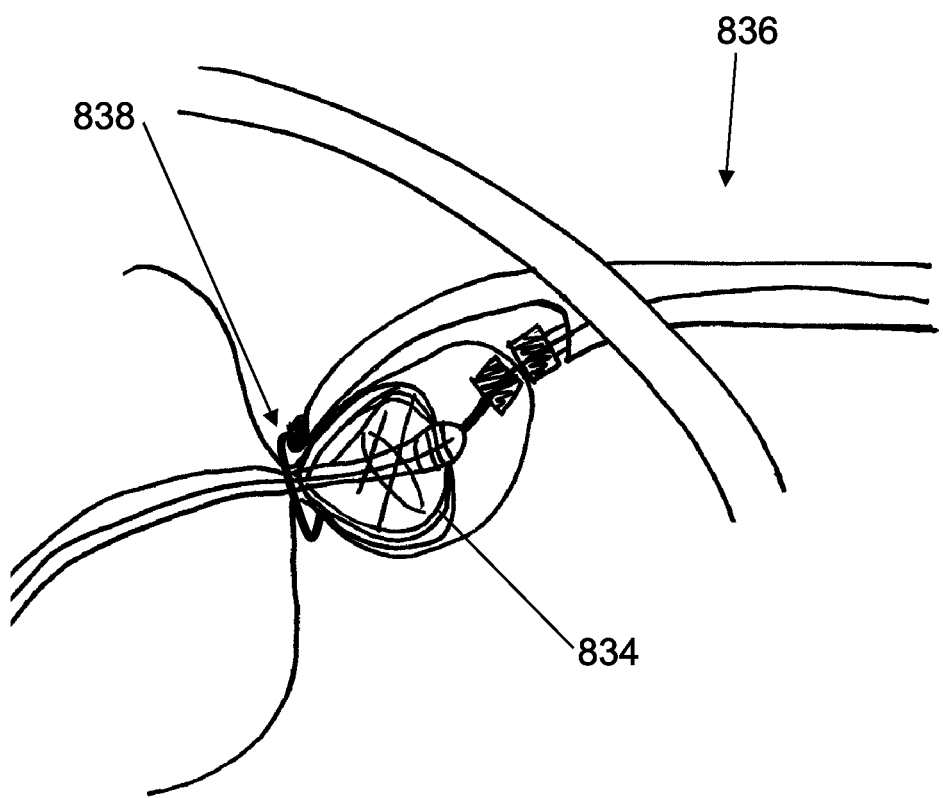

FIGS. 8G-8J depict the advancement, delivery, deployment, and withdrawal of an exemplary tissue-affecting device. Examples of tissue-affecting devices that may be introduced to the left atrial appendage include various ablation devices and/or devices that manipulate the tissue in some way (e.g., excise, grasp, pinch, extract, occlude, etc). For instance, tissue-affecting devices may be expandable (e.g., a balloon), and/or may comprise graspers or cutters. Ablation devices that may be used in the heart are described in U.S. Provisional Patent Application No. 61/323,796, filed on Apr. 13, 2010 and titled "METHODS AND DEVICES FOR TREATING ATRIAL FIBRILLATION, and U.S. patent application Ser. No. 13/086,389, filed on Apr. 13, 2011, titled "Methods and Devices for Treating Atrial Fibrillation" each of which has been previously incorporated by reference in its entirety, and a copy of which is included in the Appendix. Some tissue-affecting devices may be implantable, such as devices that occlude a region of tissue, and some tissue-affecting devices may be removable. In some variations, the tissue-affecting devices may be configured to be advanced over the exchange wire (832) from one side of the left atrial appendage to the other, e.g., from the exterior to the interior of the left atrial appendage. Depending on the size of the tissue-affecting device and whether or not it may cross a heart wall (e.g., left atrial appendage wall or ventricle wall), dilators, one-way valves, or other hemostasis devices may be used to provide an access port (e.g., an access port through the left atrial appendage) for delivery of the tissue-affecting device while minimizing the loss of blood. Other tissue-affecting devices, such as ablation devices, may be withdrawn after the procedure is completed. Tissue-affecting devices that may be used here include devices that may stretch the tissue, block or occlude a portion of the tissue, secure portions of the tissue, and/or create an incision in the tissue. In some variations, a tissue-affecting device may manipulate and position the tissue in preparation for other tissue-affecting devices, such as closure devices, or other devices as described above. For illustrative purposes, the tissue-affecting device (834) shown in FIGS. 8G-8I is an expandable device. FIG. 8G shows the tissue-affecting device (834) in its compressed configuration as it is delivered to the left atrial appendage (808), while FIG. 8I shows the tissue-affecting device (834) in its expanded configuration. The tissue-affecting device (834) may comprise one or more radio-opaque (or echogenic) markers (835) so that the location of the tissue-affecting device (834) may be monitored.

As shown in FIG. 8H, a left atrial appendage stabilization device (836) may be introduced over the exchange wire (832), where the stabilization device may optionally be configured to close the left atrial appendage. Examples of suitable left atrial appendage stabilization devices have been previously described and incorporated by reference. Once the tissue-affecting device (834) is delivered to the left atrial appendage, the stabilization device (836) may be advanced over the exchange wire (832), and/or the second access element (820). Once the stabilization device (832) has been positioned near the left atrial appendage (e.g., as guided by the exchange wire), a distal closure element (838) may be expanded to encircle the left atrial appendage. As the circumference of the closure element (838) is reduced to secure the left atrial appendage, the tissue-affecting device (834) may be deployed and/or activated. For example, as depicted in FIG. 8I, it may be deployed to its expanded configuration. Expanding the tissue-affecting device (834) may further help position the closure element (838) close to the anatomical ostium of the left atrial appendage (808). The exchange wire (832) that extends through the access port in the left atrial appendage, and/or second access element (820) may help to position the tissue-affecting device (834) within the left atrial appendage.

Once the desired effect has been attained, the tissue-affecting devices and delivery devices may be withdrawn, and the left atrial appendage access site closed. In the example of the access site closure procedure shown in FIGS. 8I and 8J, the expandable tissue-affecting device (834) is used to help close the access site by closing the left atrial appendage near the anatomical ostium. The expandable tissue-affecting device (in this variation, shown as an expandable balloon) may be inflated to position and help position the closure element (838) near the anatomical ostium of the left atrial appendage. Specifically, when the expandable device is expanded, the left atrial appendage is distended and its shape is changed from roughly conical to roughly spherical, thus better defining the junction between the left atrial appendage and left atrium. In addition, the expandable device in its expanded state may be at a pressure much greater than that of the left atrium proper, resulting in a significant differential in tension between the left atrial appendage and the left atrium. The expandable device may have one or more apertures therethrough for passage of contrast to facilitate visualization, or one or more markers thereon to confirm placement. The expandable tissue-affecting device may also be used to occlude (temporarily or permanently) the left atrial appendage. In certain variations, the closure element may be made from a biodegradable material, and may be configured to biodegrade after a sufficient time has passed to ensure scarring or formation of new tissue that effectively seals off the left atrial appendage.

While the tissue-affecting device is still in its expanded state, the closure element (838) may be placed around the left atrial appendage and closed. However, in some variations, the closure element may be placed around the left atrial appendage while the balloon is in its deflated or unexpanded state. Of course, in some instances it may be desirable to confirm proper closure of the left atrial appendage prior to, and optionally after, tightening of the closure element using fluoroscopic or other visualization techniques. If closure is not adequate or otherwise not desirable, the closure element may be opened, repositioned, closed, and then evaluated again.

Figure 8J:
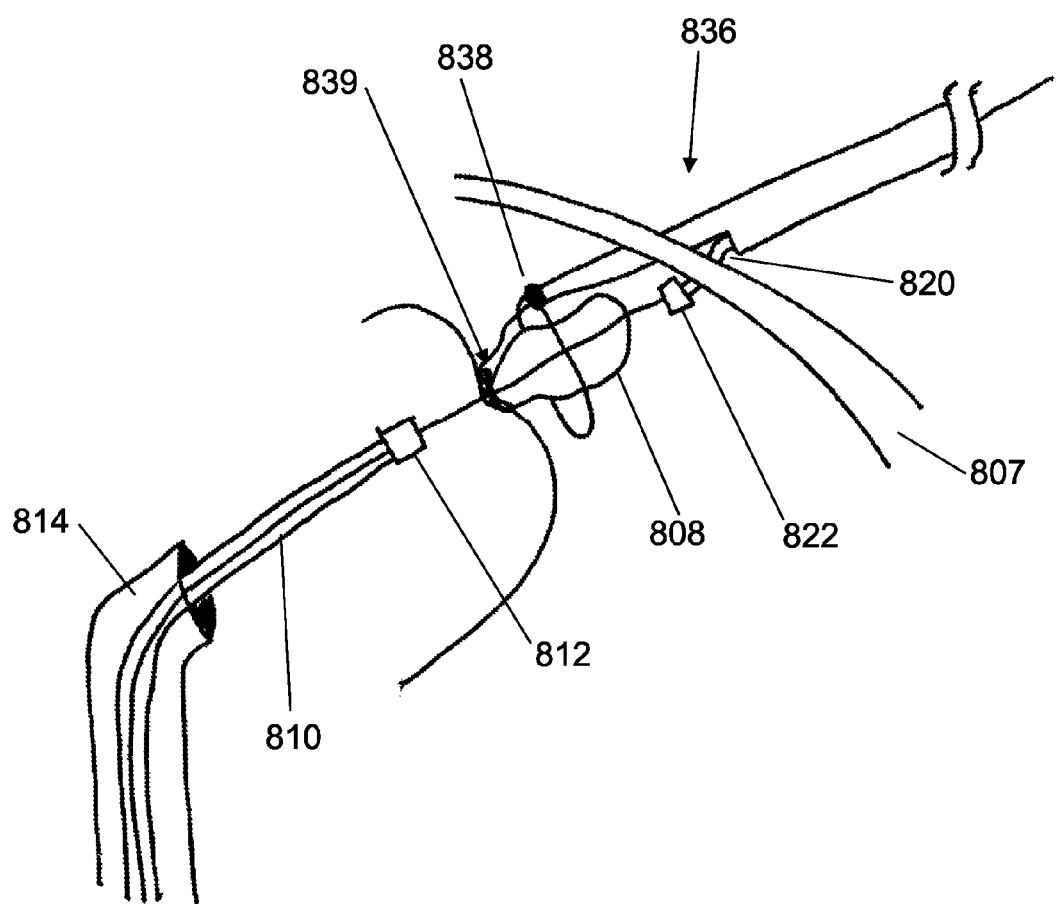

FIG. 8J also shows that once the left atrial appendage has been closed, the tissue-affecting device (834) may be withdrawn. The first and second alignment members (812, 822) may be disengaged, and the first and second access elements (810, 820) may be withdrawn. In some variations, the tissue-affecting devices may be implantable, and remain in the heart while the access devices are withdrawn. For example, the tissue-affecting device may be an occlusion device that is implanted in the left atrial appendage to isolate it from the left atrium. A suture element (839) may be used to close the access site, then decoupled from the closure element (838) by severing or cutting. Excluding the left atrial appendage as described above may be one way to close the access site without suture stitches. Alternatively or additionally, the access site may be closed with suture stitches and/or fibrin glue.

Figure 8K:
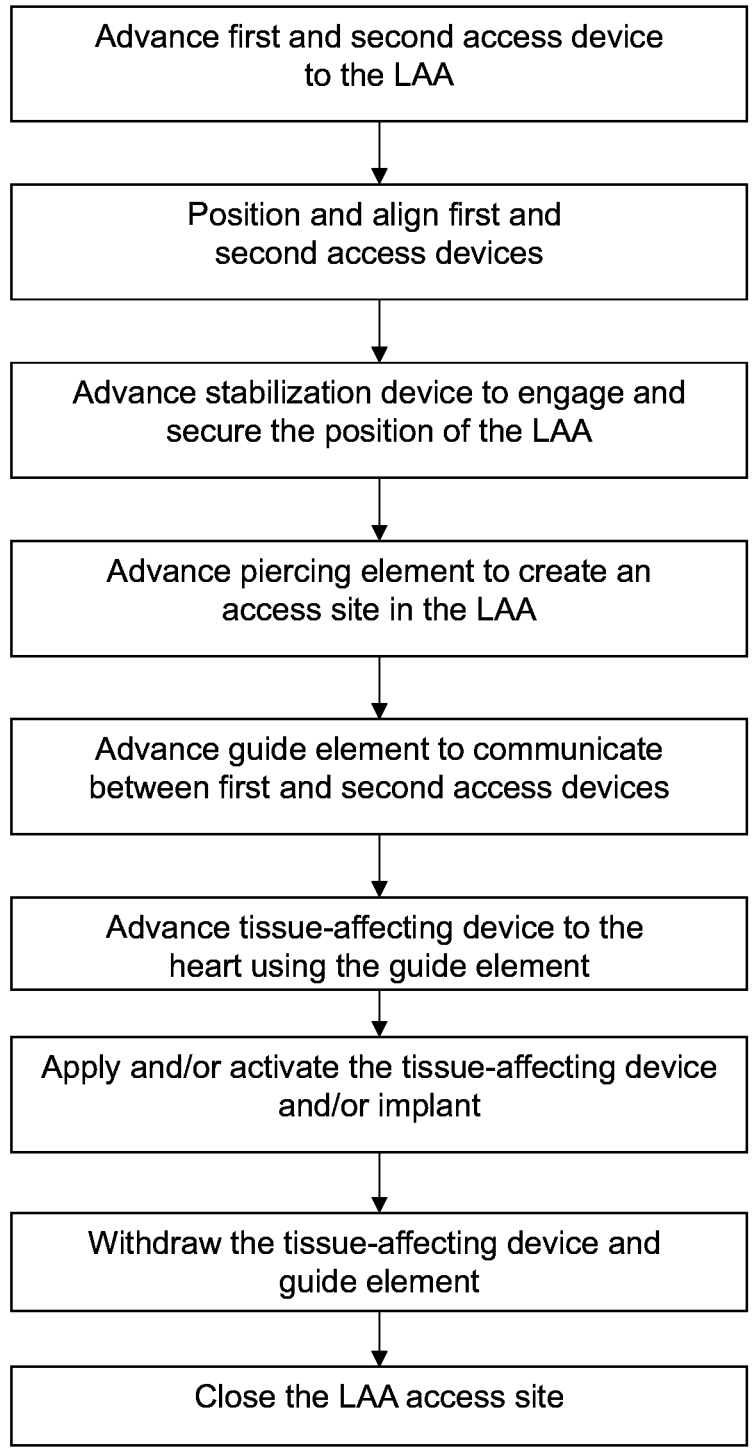

The above steps are summarized in a flowchart depicted in FIG. 8K. Of course, many variations on this method are possible. Each step of the method shown in FIG. 8K may be followed with a confirmation and/or verification step, as appropriate (e.g., verification by tactile feedback, imaging data, physiological data, and the like). The guides having the alignment members thereon may be used or removed during the method as appropriate or desirable. It should be understood that the access site of the left atrial appendage may be closed without closing the left atrial appendage at the anatomical ostium. While the method depicted in FIGS.

8A-8J comprises closing the access site by closing the left atrial appendage at the anatomical ostium, a similar method may be used where the access site is closed by suturing, fibrin glue, or any other suitable method.

E. Devices and Method for Device Delivery to a Heart Via the Left Atrial Appendage and/or the Left Ventricle As mentioned above, the devices and methods described here may be used to deliver one or more devices to the interior of the heart through one or more ports or access sites in a wall of an atrium (e.g., the left atrium or the right atrium) or a ventricle (e.g., the left ventricle or the right ventricle). Generally, to introduce a device through an atrial or ventricular wall, a first guide may be introduced into the body (via a subthoracic approach, via intercostal or intracostal access, via open surgical access, or the like) and advanced to an exterior surface of the heart wall, while a second guide may be introduced (e.g., via a femoral vein, brachial vein, or the like) into an interior chamber of the heart (e.g., the left atrium, right atrium, left ventricle, right ventricle) and advanced to an interior surface of the heart wall. The first and second guides may be aligned (e.g., via one or more magnetic alignment elements, visualization, combinations thereof, and the like), and may be used to create an access site across the tissue wall, and to place a guide element (e.g., a guide wire) therethrough. In some variations, an access catheter may be advanced over the guide element and through the heart wall. In some variations, the access catheter may comprise one or more expandable elements that may help to keep access catheter in place relative to the heart wall and/or help provide hemostasis. One or more treatment devices may then be advanced over or through the access catheter, and may be used to perform or assist in the performance of one or more procedures in the heart or surrounding vasculature.

Figure 13A:
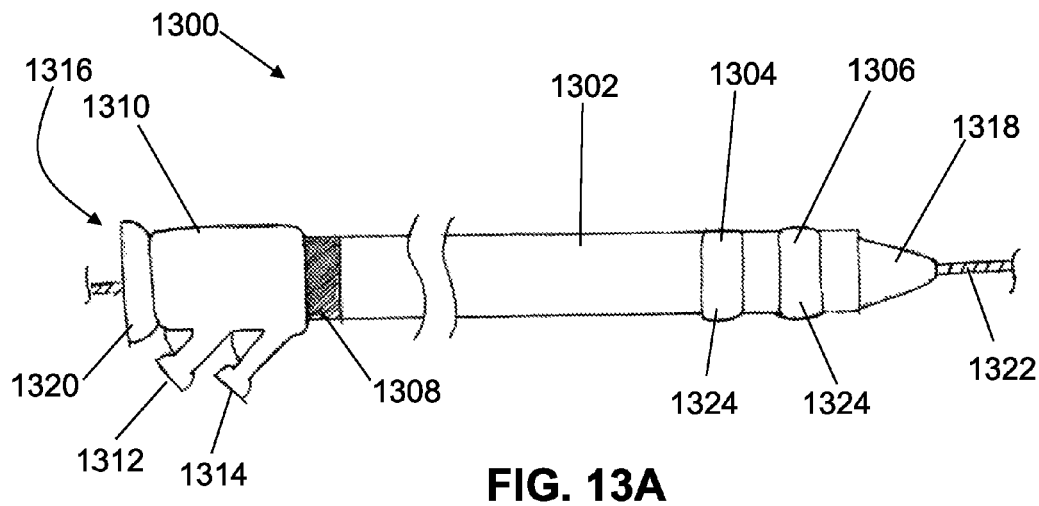
FIGS. 13A-13C and 14A-14C depict two variations of devices for placement across tissue.
Figure 13B:
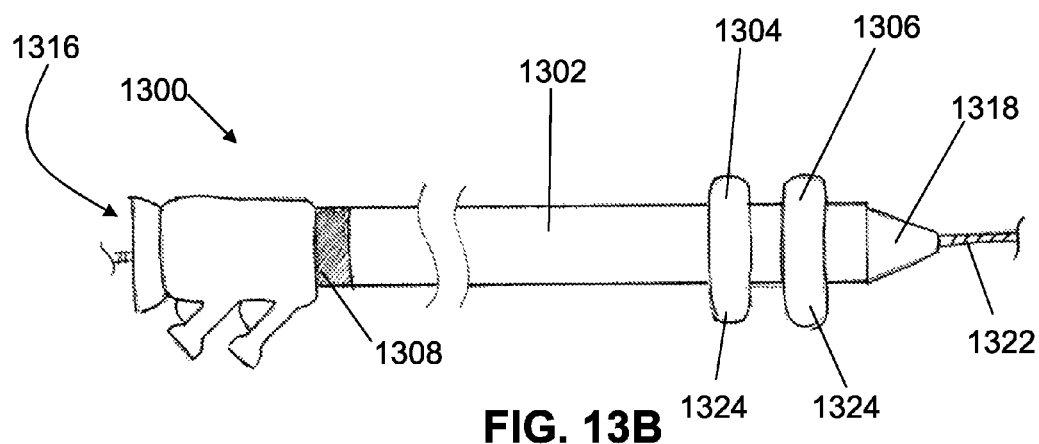
Figure 13C:
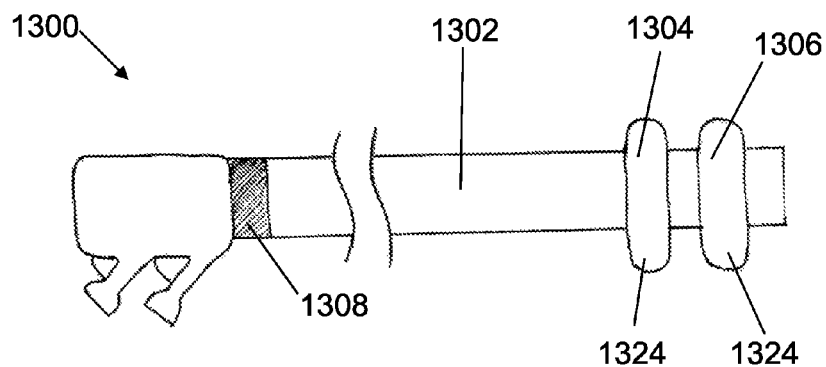

FIGS. 13A-13C depicts one variation of an access catheter (1300) that may be used with the devices and methods described here. As shown in FIG. 13A, access catheter (1300) may comprise an elongate body (1302), proximal (1304) and distal (1306) expandable members, valve portion (1308), handle (1310) comprising first (1312) and second (1314) inlet ports, and dilator (1316) comprising a tapered distal end (1318) and dilator handle (1320). Generally, elongate body (1302) may be advanced through a tissue wall (not shown) and positioned such that distal expandable member (1306) and proximal expandable member (1304) are placed on each side of the tissue wall. In some variations, the access catheter (1300) may be advanced along a guide element (1322). Once advanced and positioned, the expandable members (1304) and (1306) may be expanded, as shown in FIG. 13B. When expanded, the expandable members (1304) and (1306) may help to hold elongate body (1302) in place relative to the tissue, and may act to help prevent blood flow through the access site formed in the tissue wall. Once the elongate body (1302) is in place, the dilator (1316) may be withdrawn from the elongate body (1302), as shown in FIG. 13C, and one or more device may be advanced through the elongate body (1302), as will be described in more detail below.

While shown in FIGS. 13A-13C as having a dilator (1316), access catheter (1300) need not comprise a separate dilator (1316). For example, in some variations, the elongate body of an access catheter may have a tapered distal end. In variations of access catheters that do comprise a separate dilator, the dilator may be placed through one or more lumens of the elongate body. For example, in the variation of access catheter (1300) shown in FIGS. 13A-13C, dilator (1316) may be placed through a first lumen (not shown) of the elongate body (1302) such that the tapered distal end (1318) extends out of the distal end of the elongate body. In variations where the access catheter (1300) comprises a valve portion (1308), dilator (1316) may also pass through the valve portion (1308). In some variations, dilator (1316) may comprise a lumen extending therethrough. In instances where access catheter (1300) is advanced over a guide element (1322), such as a guide wire, the guide element (1322) may be threaded through the lumen of the dilator (1316), such that dilator (1316) can be advanced over and guided by guide element (1322).

As mentioned above, access catheter (1300) may comprise a valve portion (1308). Valve portion may comprise any suitable hemostasis valve that is suitable for the passage for one or more devices therethrough. While shown in FIGS. 13A-13C as being located at a proximal end of the elongate body, the valve portion (1308) may be located at any point along the length of the elongate body (e.g., at a distal end, at an intermediate point, etc.), or may be attached to or otherwise contained within handle (1310).

While shown above as having two expandable members (proximal (1304) and distal (1306) expandable members), access catheter (1300) may comprise any suitable number of expandable members. In some variations, the access catheter (1300) may comprise a single expandable member. In some of these variations, the expandable member may be positioned such that the entire expandable member may be placed on one side of the tissue wall. In others of these variations, the expandable member may be sized and configured to be positioned such that a first portion of the expandable member may be positioned on a first side of the tissue wall, and a second portion of the expandable member may be positioned on a second side of the tissue wall. In other variations, the access catheter (1300) may comprise three or more expandable members, or may not comprise an expandable member. Additionally, while shown in FIGS. 13A-13C as being fixed along the length of elongate body (1302), it should be appreciated that one or more of the expandable members (1304) and (1306) may be moveable along the length of the elongate body (1302). In these variations, one or more of the expandable member (1304) and (1306) may be moved relative to each other along elongate body (1302) to alter the distance between the expandable members (1304) and (1306). This may help to allow for access catheter to be adjusted for varying wall thicknesses when placed across heart tissue The proximal (1304) and distal (1306) expandable members may be any suitable expandable structure (e.g., one or more balloons, expandable cages, meshes, baskets, combinations thereof, and the like). In variations where an access catheter comprises multiple expandable members, each of expandable members may comprise the same expandable structure, or different expandable members may comprise different expandable members. In the variation of access catheter (1300) shown in FIGS. 13A-13C, proximal (1304) and distal (1306) expandable members may comprise inflatable balloons (1324). The inflatable balloons (1324) may be compliant, semi-compliant, or non-compliant, and the inflatable balloons (1324) may be inflated by introducing a liquid or gas to the balloon (1324). In some variations, fluid may be introduced to the inflatable balloons (1324) via first (1312) and/or second (1314) inlet ports, and through one or more inflation lumens (not shown) in or attached to the elongate body. In some variations, inflatable balloons (1324) may be inflated by separate inlet ports (e.g., distal expandable member (1306) may be inflated via first inlet port (1312), and proximal expandable member (1304) may be inflated via second inlet port (1314)). In other variations, inflatable balloons (1324) may be inflated by the same inlet port.

Figure 14A:
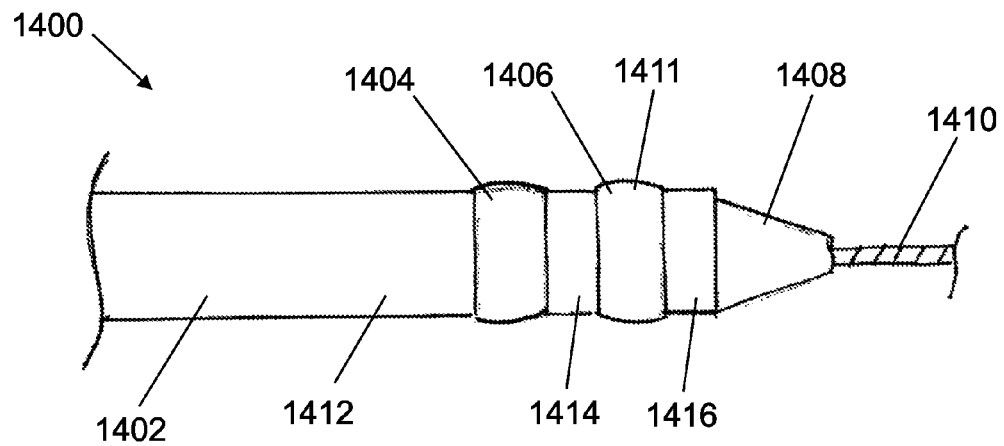
Figure 14B:
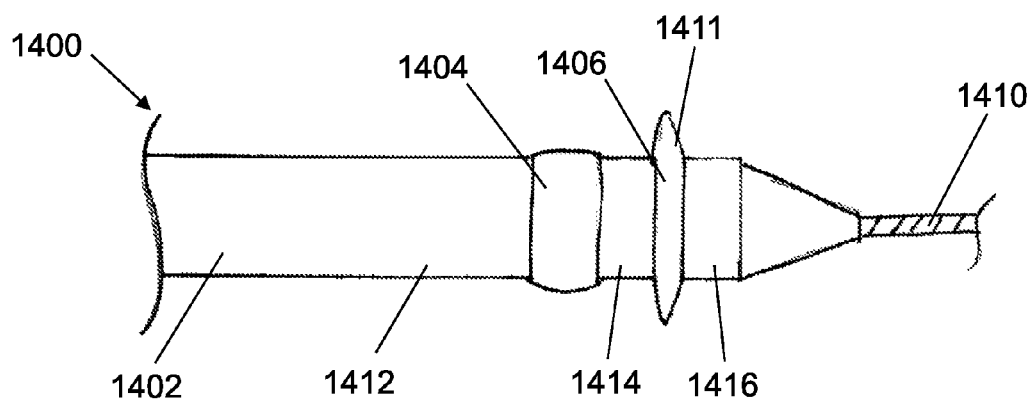
Figure 14C:
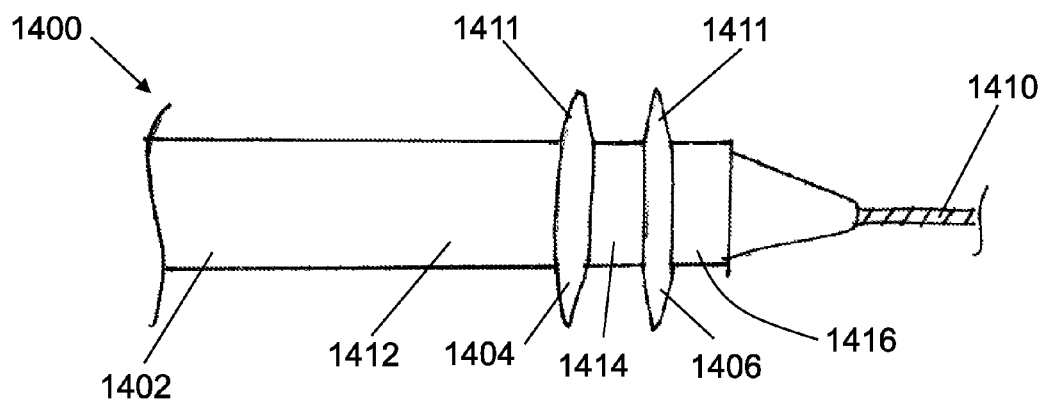

FIGS. 14A-14C illustrate the distal portion of a variation of access catheter (1400). As shown in FIG. 14A, access catheter (1400) may be advanceable along guide element (1410), and may comprise an elongate body (1402), proximal expandable member (1404), distal expandable member (1406), and dilator (1408). In this variation, proximal (1404) and distal (1406) expandable members may comprise a compressible section (1411) (e.g., a compressible mesh, weave, tubing, or the like). For example, elongate body (1402) may comprise a first portion (1412), a second portion (1414), and a third portion (1416), such that proximal expandable member (1404) may be positioned between first (1412) and second (1414) portions of elongate body (1402), and distal expandable member (1406) may be positioned between second (1414) and third (1416) portions of elongate body (1402). To expand distal expandable member (1406) access device may be configured to move third portion (1416) toward second portion (1414) of elongate body (1402) (or vice versa), which may compress distal expandable member (1406), which may cause the compressible section (1411) to expand outwardly, as shown in FIG. 14B. Similarly, to expand proximal expandable member (1404) access device may be configured to move second portion (1414) toward first portion (1412) of elongate body (1402) (or vice versa), which may compress proximal expandable member (1404), which may cause the compressible section (1411) to expand outwardly, as shown in FIG. 14C. In some variations, each of first (1412), second (1414) and/or third (1416) portions of elongate body (1402) may be a portion of first catheter, second catheter, and/or third catheter (not shown), wherein the first, second, and third catheters may be movable relative to each other in order to compress and uncompress the proximal and/or distal expandable members.

As mentioned above, the devices and methods described here may be used to deliver one or more devices to the interior of the heart through one or more ports or access sites in a wall of an atrium (e.g., the left atrium or the right atrium) or a ventricle (e.g., the left ventricle or the right ventricle). FIGS. 15A-15G illustrate one variation of a method for accessing an interior of the heart using a transapical access site (e.g., an access site in a ventricle wall at or near the apex of the heart) and using a left atrial appendage access site. Generally, this method may comprise using an access device (such as one or more of the access devices described above) to form an access site or port through tissue of the left atrial appendage, and using an access device to form an access site or port through tissue of the left ventricle. In some variations, a first guide element may be advanced to position the first guide element through the access site in tissue of the left atrial appendage, such that a distal end of the first guide element may be positioned inside of the heart (e.g., in the left atrium, left ventricle, etc.) or the surrounding vasculature. A proximal end of the first guide element may be positioned external to the body, such that one or more dilators, access catheters, and/or treatment devices may be advanced over the first guide element. A second guide element may be advanced to position the second guide element through the access site in tissue of the left ventricle, such that a distal end of the first guide element may be positioned inside of the heart (e.g., in the left ventricle, left atrium, etc.) or the surrounding vasculature. A proximal end of the first guide element may be positioned external to the body, such that one or more dilators, access catheters, and/or treatment devices may be advanced over the first guide element.

Optionally, a closure/stabilization device may be placed around the left atrial appendage to stabilize the left atrial appendage and/or control hemostasis at the left atrial appendage access site. In some variations, one or more access catheters may be introduced into the left atrial appendage access site and/or the left ventricle access site. One or more treatment devices may be advanced into the heart via the left atrial appendage and/or the left ventricle access sites to perform one or more procedures in the heart (such as one or more of the procedures described in more detail below). Following completion of the procedures, the devices (e.g., treatment devices, access catheters, guide elements, etc.) may be removed, and the left atrial appendage access site and/or left ventricle access site may be closed, occluded, or otherwise sealed. In some variations, the left atrial appendage access site may be closed, occluded, or otherwise sealed by one or more treatment devices advanced through the left ventricle access site. In other variations, the left atrial appendage access site may be closed, occluded, or otherwise sealed by one or more treatment devices advanced through the left atrial appendage access site.

Figure 15B:
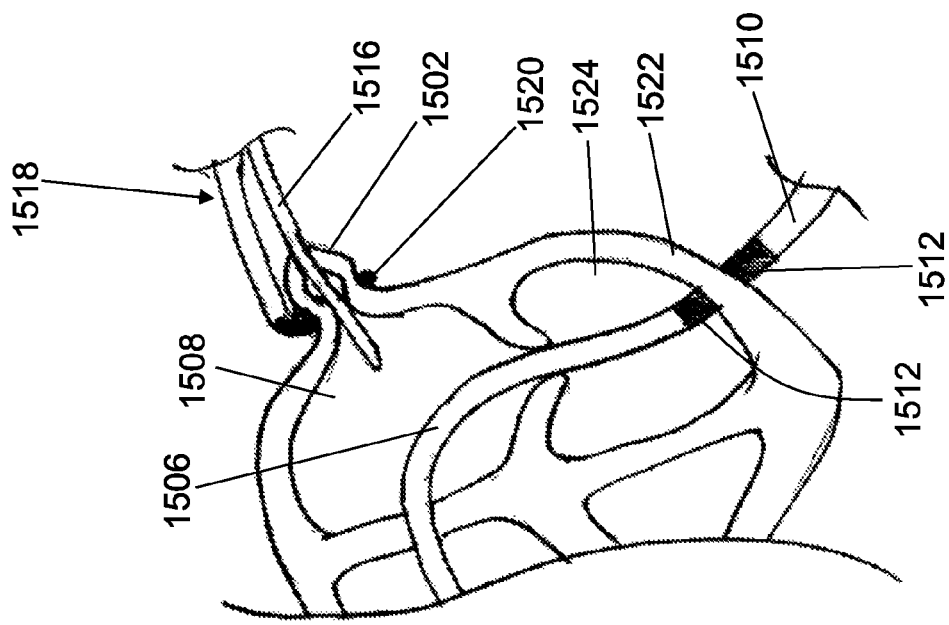
Figure 15A:
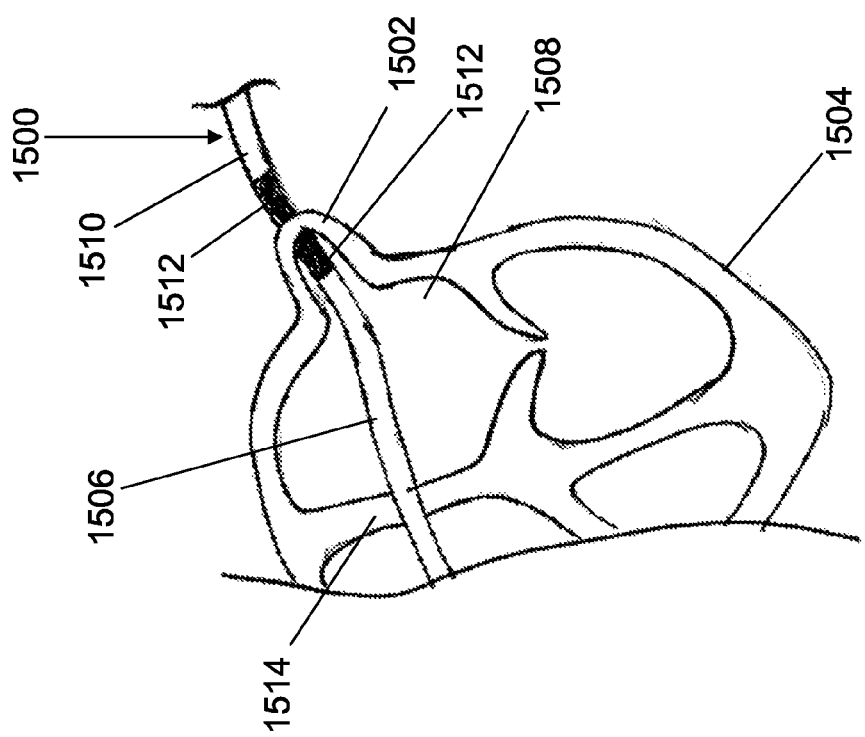

Returning to the variation of the method shown in FIGS. 15A-15G, an access device (1500) may be utilized to form an access site in the left atrial appendage (1502) of heart (1504). Specifically, a first guide (1506) may be advanced through the left atrium (1508) to position a distal portion of the first guide (1506) into the interior of the left atrial appendage (1502), while a second guide (1510) may be advanced externally to the heart (e.g., via a pericardial approach) to position a distal portion of the second guide (1510) at or near the left atrial appendage, as depicted in FIG. 15A. While shown there as being advanced intravascularly and transeptally (e.g., through a catheter (not shown) placed at least partially through the septum (1514)), it should be appreciated that the first guide (1506) may be introduced into the left atrial appendage in any suitable manner. In some variations, first guide (1506) may be introduced intravascularly via a retrograde pathway from the aorta. In variations where an access site has already been formed through a heart wall (e.g., the wall of the left ventricle), the first guide (1506) may be advanced into the heart through the heart wall access site.

Advancement of the first (1506) and/or second (1510) guides may be done under visualization (e.g., using fluoroscopic visualization, ultrasound visualization, a combination thereof, or the like). In some variations, first (1506) and second (1510) guides may be aligned using one or more alignment elements. For example, as shown in FIG. 15A, first (1506) and second (1510) guides may comprise magnetic alignment elements (1512) at the distal ends of each guide, which may attract each other through tissue of the left atrial appendage (1502). Access device (1500) may then be used to form an access site through the left atrial appendage (1502), and place a guide element (1516) (e.g., a guide wire or the like) through the access site. For example, in some variations, one or more of first (1506) and second (1510) guides may comprise one or more lumens (not shown) extending therethrough, and one or more guide elements may be passed through the lumens of the first (1506) and/or second (1510) guides. In some variations, a piercing member (not shown) may be advanced through a lumen of the second guide (1510) to create a puncture in the left atrial appendage. In some of these variations, the piercing member may be withdrawn from the lumen of the second guide (1510), and a guide element (1516) may be advanced through the lumen of the second guide (1510) and through the puncture in the left atrial appendage (1502). In others of these variations, the piercing member may be releasably attached to the guide element (1516), and advancement of the piercing member may pull or otherwise advance the guide element (1516) through the second guide (1510) and the puncture in the left atrial appendage (1502), as described in more detail above. In still other variations, a guide element may comprise a sharpened end, and may be advanced through the second guide (1510) to directly puncture or pierce tissue. As guide element (1516) is advanced from second guide (1510) through tissue of the left atrial appendage (1502), it may at least partially enter the lumen of the first guide (1506). Once the guide element (1516) has been properly positioned through the access site in the left atrial appendage (1502), the first (1506) and second (1510) guide may be at least partially withdrawn to leave guide element in place, as shown in FIG. 15B. While guide element (1516) is described immediately above as being initially advanced from the second guide (1510) through the access site, it should be appreciated that the guide element (1516) may be positioned as shown in FIG. 15B by advancing the guide element (1516) and/or a piercing element from the first guide (1506), in any of the manners described above. It should also be appreciated that one or more alternative methods, such as one or more steps from the methods described above in relation to FIGS. 7A-7I or FIGS. 8A-8K may be utilized to create an access site through the left atrial appendage (1502) and to place a guide element (1516) inside the heart (1504) via the left atrial appendage access site.

Also shown in FIG. 15B is a stabilization device (1518), which may be used to place a closure element (1520) around the left atrial appendage (1502). Closure element (1520) may be selectively closed around the left atrial appendage (1502) to help stabilize and/or maintain hemostasis through the left atrial appendage access site. Closure element (1520) may be placed around the left atrial appendage prior to or after formation of the access site through the left atrial appendage (1502). In some variations, closure element (1520) is placed around the left atrial appendage prior to puncturing the left atrial appendage (1502), and closure element (1502) may be closed or otherwise tightened to close the left atrial appendage (1502) around the first guide (1506). Closure of the left atrial appendage (1502) around the first guide (1506) may help to limit blood flow from the left atrium (1508) into the left atrial appendage (1502), which may reduce the amount of blood that may leave the left atrial appendage (1502) through the access site. When first guide (1506) is withdrawn from the left atrial appendage (1502) to leave guide element (1516) in place through the access site, closure element (1520) may be further tightened, cinched or close to close the left atrial appendage (1502) around the guide element (1516), as shown in FIG. 15B. It should be appreciated that the closure element (1520) may be any suitable closure element, such as described in more detail above, and may be selectively tightened and opened to help accommodate different devices as they are advanced into the left atrial appendage.

The methods described here may also be used to place a guide element through a heart wall. As shown in FIG. 15B, access device (1500) may be used to form an access site through the wall (1522) of left ventricle (1524). As shown there, first guide (1506) may be advanced through the left atrium (1508) to position a distal portion of the first guide (1506) into the left ventricle (1524), while second guide (1510) may be advanced externally to the heart (e.g., via a pericardial approach) to position a distal portion of the second guide (1510) at or near the wall (1522) of the left ventricle (1524). The first (1506) and second (1510) guides may be aligned across wall (1522) in any suitable manner as described above. In some variations, the magnetic alignment elements (1512) of the first (1506) and second (1510) guides may attract each other through the wall (1522) of the left ventricle (1524) to align first (1506) and second guides (1510) as shown in FIG. 15B.

Figure 15D:
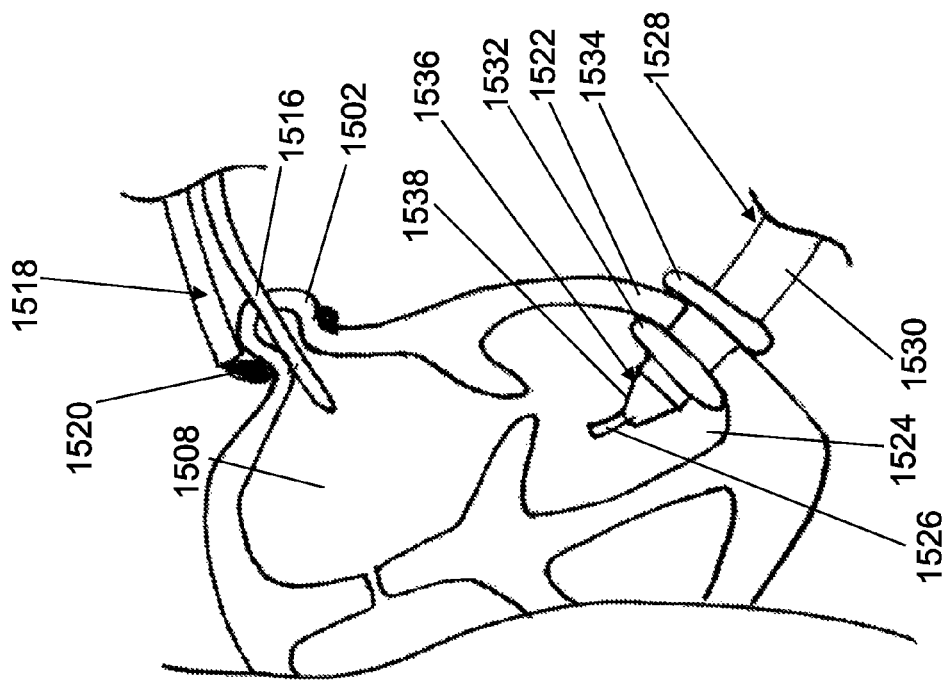
Figure 15C:
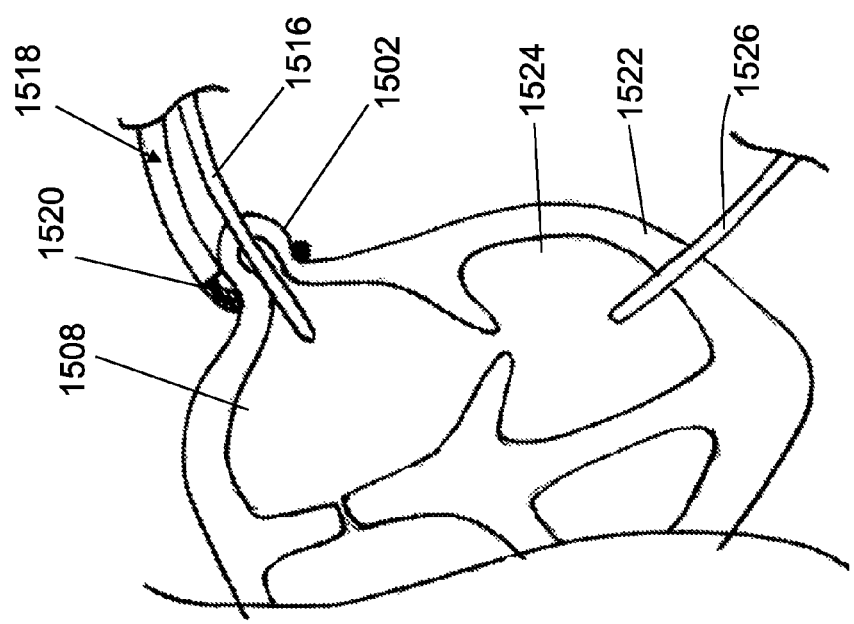

Access device (1500) may then be used to form an access site through the wall (1522) of the left ventricle (1524), and may place a guide element (1526) (e.g., a guide wire or the like) through the left ventricle access site. In some variations, a piercing member (not shown) may be advanced through the lumen of the second guide (1510) to create a puncture in the wall of the left ventricle. In some of these variations, the piercing member may be withdrawn from the lumen of the second guide (1510), and guide element (1526) may be advanced through the lumen of the second guide (1510) through the puncture in wall (1522), and into the left ventricle (1524). In others of these variations, the piercing member may be releasably attached to the guide element (1526), and advancement of the piercing member may pull or otherwise advance the guide element (1526) through the second guide (1510) and the puncture in the wall (1522) of the left ventricle (1524), as described in more detail above. In still other variations, a guide element may comprise a sharpened end, and may be advanced through the second guide (1510) to directly puncture or pierce tissue. Additionally, as noted above with respect to guide element (1516), as guide element (1526) is advanced from second guide (1510) through tissue, it may at least partially enter the lumen of the first guide (1506). Once the guide element (1526) has been properly positioned through the access site in the wall (1522) of the left ventricle (1524), the first (1506) and second (1510) guide may be at least partially withdrawn to leave guide element (1526) in place, as shown in FIG. 15C. While guide element (1526) is described immediately above as being initially advanced from the second guide (1510) through the access site, it should be appreciated that the guide element (1526) may be positioned as shown in FIG. 15C by advancing the guide element (1526) and/or a piercing element from the first guide (1506), in any of the manners described above. Additionally or alternatively, the proximal portion (not shown) of one or more of the guide elements (e.g., guide element (1516) and/or guide element (1526) may comprise one or more depth markers (not shown), which may be used to determine the length of the guide element that is contained in tissue.

In some variations, such as the variation of the method shown in FIGS. 15A-15G, the same access device may be used to form both the left atrial appendage and left ventricle access sites. In these variations, the first guide (1506) may be fully withdrawn from the heart and then re-advanced into the heart between the creation of the left atrial appendage access site and creation of the left ventricle access site, or a distal portion of the first guide (1506) may remain in the heart. Similarly, second guide (1506) may be fully withdrawn from the body and re-advanced into the pericardial space between creation of the left atrial appendage access site and creation of the left ventricle access site, or a distal portion of the second guide (1510) may remain in the heart. It should be appreciated that a different access device may be used to form the left ventricle access site. In variations where the first (1506) and/or second (1510) guides are re-advanced into the heart and/or pericardial space, the first (1506) and/or second (1510) guides may be re-advanced using the same access pathways, or using one or more different access pathways.

In other variations, different access devices may be used to form the left atrial appendage access site and the left ventricle access site. For example, in some variations, a second access device (not shown) may be used to form the left ventricle access site. In some of these variations, the second access device may comprise a third guide and/or fourth guide. The third guide may be advanced into the left ventricle to position a distal portion of the third guide at or near the wall (1522) of the left ventricle (1524). The third guide may be advanced in any suitable manner as described above (e.g., intravascularly via a transeptal approach, intravascularly via a retrograde pathway from the aorta). In variations where an access site has already been formed in the left atrial appendage (1502), as described in more detail above, the third guide may be advanced through the left atrial appendage access site, through the left atrium (1508), and into the left ventricle (1524). Similarly, fourth guide may be advanced externally to the heart (e.g., via a pericardial approach) to position a distal portion of the second guide (1510) at or near the wall (1522) of the left ventricle (1524). Third and fourth guides may be aligned and used to create an access site through the wall (1522) of the left ventricle and to place a guide element therethough, in any manner such those described above in relations to FIGS. 15B-15C and first (1506) and second (1510) guides.

While the variation of the method shown in FIGS. 15A-15G as creating a left atrial appendage access site prior to forming a left ventricle access site, it should be appreciated that the access sites may be created in any suitable order. For example, in some variations, the left ventricle access site may be created prior to creation of the left atrial appendage access site. In other variations, the left atrial appendage access site and the left ventricle access site may be created substantially simultaneously (e.g., a first access device may be introduced and used to form an access site across the left atrial appendage while a second access device is introduced and used to form an access site across the wall of the left ventricle).

Figure 15E:
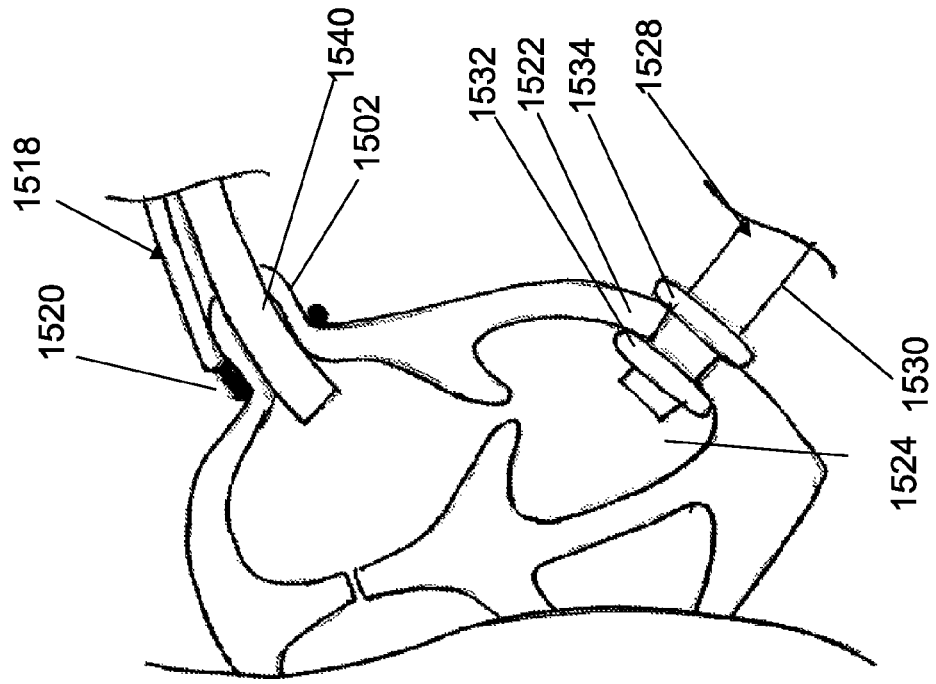

Returning to the figures, in some variations, an access catheter may be advanced over guide (1526) to place a portion of the access catheter across the access site in the wall (1522) of the left ventricle (1524). Access catheter may be any suitable access catheter, such as the variations of access catheters (1300) and (1400) described in more detail above. FIGS. 15D and 15E shows the distal portion one such variation of access catheter (1528) which may be advanced along guide (1526). As shown there access catheter (1528) may comprise an elongate body (1530) with a first lumen (not shown) extending therethrough, first (1532) and second (1534) expandable members, dilator (1536) disposed at least partially through the first lumen of the elongate body (1530), and hemostatic valve portion (not shown). Expandable members (1532) and (1534) may be any suitable expandable structure, such as those described above (e.g., a balloon, an expandable mesh, basket, cage, or the like). Dilator (1536) may comprise a tapered tip (1538) and one or more lumens extending through the body of the dilator. Dilator may be advanced along guide element (1526) to advance the tapered tip (1538) of dilator through the wall (1522) of ventricle (1524). As the tapered tip (1538) passes through the wall (1522) of left ventricle (1524), it may dilate or otherwise expand the left ventricle access site. Access catheter (1528) may be further advanced to place first (1532) and second (1534) expandable members on either side of wall (1522), and the first (1532) and second (1534) expandable members may be expanded, as shown in FIG. 15D. This may be done in any suitable manner. For example, in some variations, access catheter (1528) may be advanced over guide element (1526) such that first expandable member (1532) is positioned inside of the left ventricle (1524) (positioning may be confirmed via depth markers on a proximal portion of the access catheter (1528) or via one or more visualization techniques such as those described in more detail above), and first expandable member (1532) may be expanded. Access catheter (1528) may then be withdrawn to pull the expanded first expandable member (1532) into contact with the wall (1522) of the left ventricle (1524), and second expandable member (1534) may be expanded on the other side of wall (1522). In other variations, the first (1532) and second (1534) expandable members may be expanded simultaneously. In still other variations, second expandable member (1534) may be positioned and expanded outside of the heart near the wall (1522) of left ventricle (1524). The access catheter (1528) may be advanced to press the second expandable member (1534) against the wall (1522) of the left ventricle (1524), and the first expandable member (1532) may be expanded inside of left ventricle (1524). When first (1532) and second (1534) expandable members are expanded on opposite sides of tissue, the expandable members may help to prevent blood from exiting the left ventricle (1524) through the left ventricle access site. In some variations, the expandable members (1532) and (1534) may surround the access site and/or may apply pressure thereto to help provide a hemostatic seal.

Once access catheter (1528) has been properly positioned, dilator (1536) (and optionally guide element (1526)) may be withdrawn through the first lumen of the elongate body (1530), as shown in FIG. 15E. As dilator (1536) is withdrawn from the elongate body (1530), a hemostasic valve portion of the access catheter (1528) may prevent or otherwise limit blood flow through the first lumen of the elongate body (1530). The hemostatic valve portion, such as those described in more detail above, may be configured to accommodate the passage of one or more treatment devices therethrough, such that they may be introduced into the interior of the heart. Additionally or alternatively, a second access catheter (1540) may be advanced through the left atrial appendage. In some variations, one or more dilators (not shown) may be advanced over guide element (1516) to place access catheter (1540) across the left atrial appendage access point, and the guide element (1516) may optionally be removed, as shown in FIG. 15E. During advancement of the dilators and/or access catheter (1540), closure element (1520) may be temporarily opened to accommodate the advancement of the devices through the left atrial appendage (1502) access site, and may be re-tightened to close the left atrial appendage (1502) around the dilator and/or access catheter (1540). The second access catheter (1540) may be any suitable catheter, such as those described in more detail below. In the variation of access catheter (1540) shown in FIG. 15E, the access catheter (1540) may comprise a hemostatic valve portion (not shown) that may help prevent or limit blood flow through a lumen of the access catheter (1540).

Figure 15F:
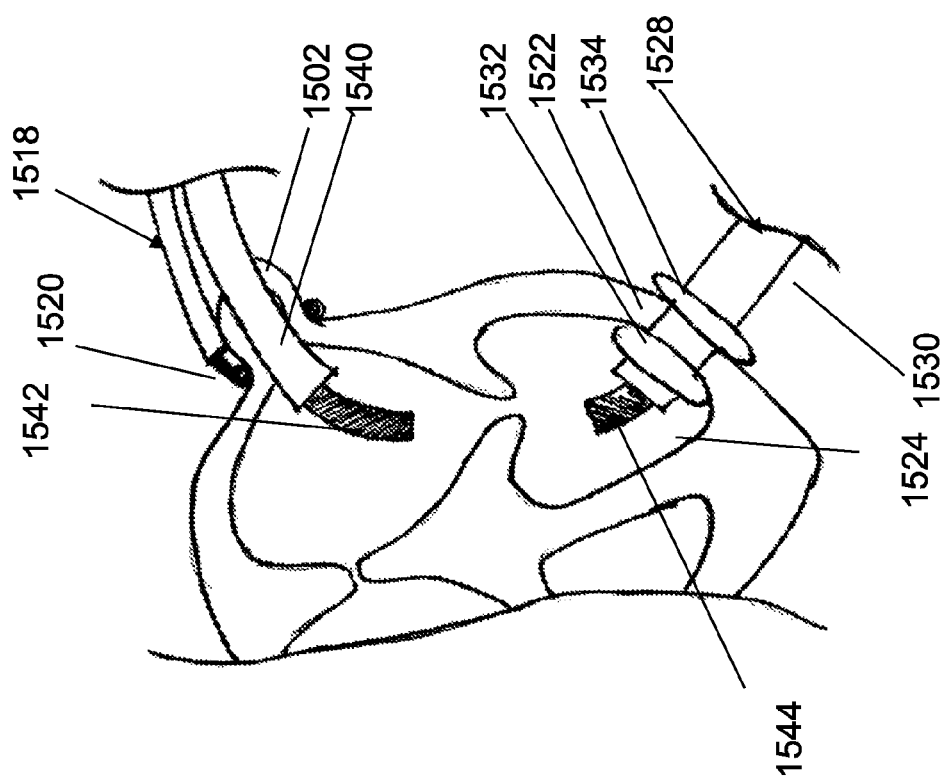

Once access catheters (1528) and (1540) are properly positioned, one or more treatment devices may be advanced therethrough. As shown in FIG. 15F, a first treatment device (1542) may be advanced into the left atrium (1508) through a lumen of the access catheter (1540) via the left atrial appendage access site, and a second treatment device (1544) may be advanced into the left ventricle (1524) through access catheter (1528) (e.g., through the first lumen of the elongate member (1530)) via the left ventricle access site. The first (1542) and/or second (1544) treatment devices may be advanced to one or more portions of the heart (e.g., left atrium, right atrium, left ventricle, right ventricle, combinations thereof, etc.), and the devices may be used to perform one or more procedures within the heart (e.g., may perform one or more steps of a valve replacement, repair or remodeling procedure, close a patent foramen ovale or other atrial septal defect, perform one or more steps of a chordae tendineae repair or replacement procedure, one or more steps of an ablation procedure, deliver one or more implants, combinations thereof, etc.), such as one or more of the procedures described in more detail below. During the course of the procedure, first (1542) and/or second (1544) treatment devicesmay be removed from the heart and re-advanced as needed, and one or more additional devices or implants may be introduced to the interior of the heart through either the left atrial appendage access site or the left ventricle access site. Any suitable treatment device (e.g., one or more visualization devices, one or more implants, one or more ablation devices, one or more suturing devices, etc.) may be advanced into the heart via these access sites. Following the completion of the one or more procedures, any treatment devices, guide elements, and access catheters, etc. may be removed from the heart. In some variations, the left atrial appendage access site and/or the left ventricle access site may be closed off and/or otherwise sealed. For example, in the variation shown in FIG. 15G, closure element (1520) may be closed around the left atrial appendage (1502) to ligate the left atrial appendage, which may prevent blood flow from the left atrium (1508) into the left atrial appendage (1502) (as shown there, a portion of closure element (1520) may be left in place), and a sealing device (1546) may be placed in the tissue wall (1522) of left ventricle (1524) to occlude the left ventricle access site. The left atrial appendage and left ventricle access sites may be closed in any suitable manner. In some variations, the left atrial appendage (1502) may be closed, occluded, or otherwise sealed by any suitable device or implant, such as described in more detail below. In some of these variations, one or more devices may be advanced through the left ventricle access site to assist in closing and/or occluding the left atrial appendage (1502). For example, in some variations an implant (e.g., an inflatable balloon or the like) may be delivered to the interior of the left atrial appendage (1502), and may optionally may be left in place. The left ventricle access site may be closed or otherwise occluded using one or more implants, adhesives, suturing procedures, or the like.

Figure 16B:
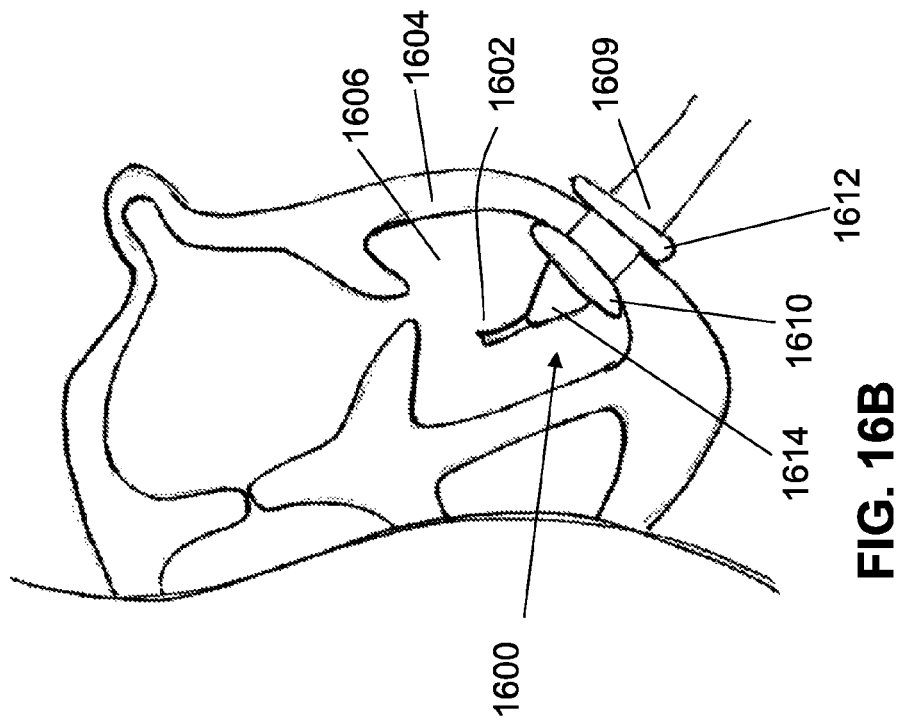
Figure 16A:
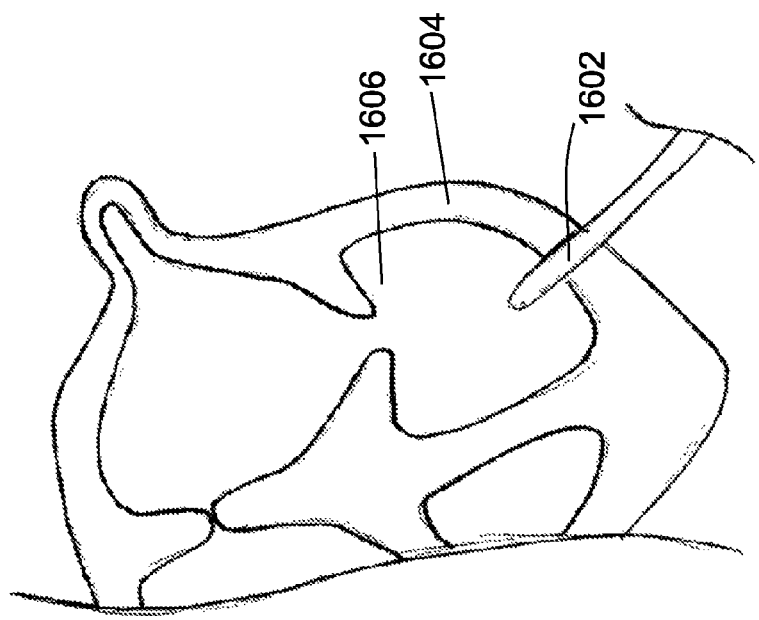
Figure 16D:
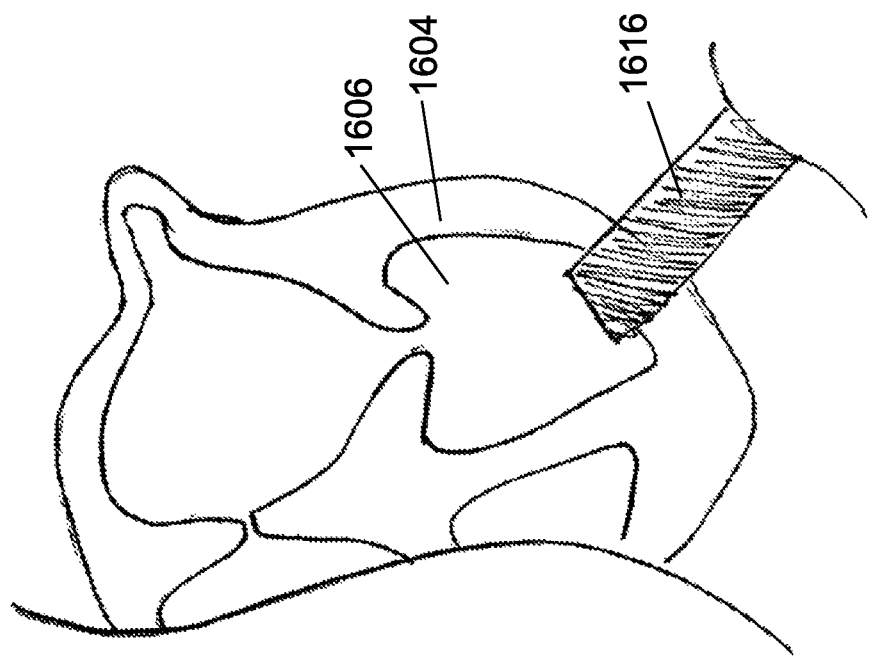

While first (1542) and second (1544) treatment are devices are shown in FIG. 15F as advanced into the heart through lumens of access catheters (1528) and (1540) respectively, it should be appreciated that a treatment device, catheter, or other structure may be advanced over an outer surface of an access catheter to place that structure through a tissue access site. For example, FIG. 16A-16D illustrate a variation of a method by an which an access catheter (1600) may be placed in a tissue access site. As shown in FIG. 16A, a left ventricle access site may be created and a guide element (1602) may be placed through the wall (1604) of the left ventricle (1606) via the left ventricle access site using one or more of the devices and methods described above. An access catheter (1600) comprising an elongate body (1609) having a dilating tip (1614), and first (1610) and a second (1612) expandable members may be advanced over guide element (1602) and positioned such that first (1610) and second (1612) expandable members are expanded on either side of the wall (1604) of the left ventricle (1606), as shown in FIG. 16B. Access catheter (1600) may be advanced, and first (1610) and second (1612) expandable members may be positioned in any manner as described immediately above. Dilating tip (1614) may act to dilate or otherwise expand the opening of left ventricle access site as it is advanced through the wall (1604) of the left ventricle (1606). When in place, access catheter (1600) may help maintain hemostasis of the left ventricle access site.

Figure 16C:
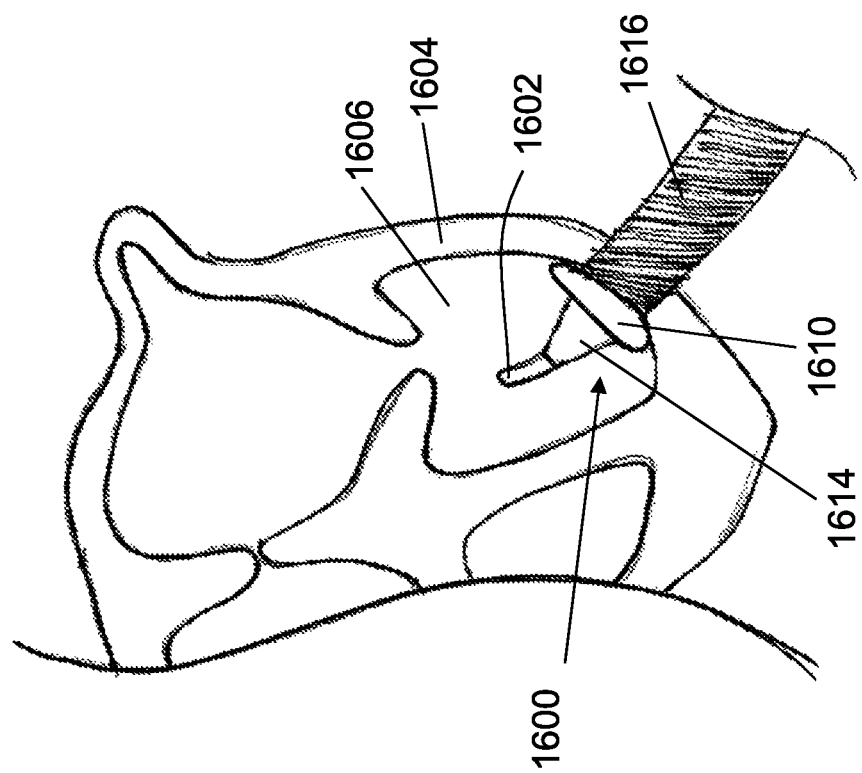

As shown in FIG. 16C, a device (1616) may be advanced over the elongate body (1609) of the access catheter (1600). Device (1616) may be any catheter or treatment device with at least one lumen (not shown) that is large enough to be passed over the outer diameter of the access catheter (1600). In order to advance device (1616) through the wall (1604) of the left ventricle (1606), second expandable member (1612) may be unexpanded to allow the device (1616) to be advanced thereover. Once through the wall, the first expandable member (1610) may be unexpanded to allow device (1616) to be advanced thereover and into the left ventricle (1606). Once the distal end device (1616) has been advanced into the left ventricle (1606), access catheter (1600) may be withdrawn through the lumen of device (1606) to leave device (1616) in place. The device (1616) may be used to perform one or more procedures in the heart, or may serve as an access device through which one or more additional devices may be passed.

While described above as creating tissue access sites in the left atrial appendage and/or the left ventricle, it should be appreciated that the devices and methods described here may be used to create access sites in any suitable tissue or combinations of tissues (e.g., the left atrial appendage, the right atrial appendage, a left ventricular wall, a right ventricular wall, a right atrial wall, a left atrial wall, the left atrial appendage and a left ventricular wall, the right atrial appendage and a right ventricular wall, a right atrial wall and a right ventricular wall, a left atrial wall and a left ventricular wall, the left atrial appendage and a right atrial wall, the left atrial appendage and a right ventricular wall, combinations thereof, and the like).

II. Systems for Accessing and Delivering Devices to a Heart

Also described here are systems for accessing and delivering devices to the heart using the left atrial appendage as an access site. In general, the systems may comprise a first access element with a first alignment member, a second access element with a second alignment member, a guide element, one or more treatment devices, and a closure device. First and second access elements may each comprise a longitudinal lumen therethrough. In some variations, some systems may also comprise a piercing element that is configured to pass through the lumen of one access element to the lumen of the other access element and creates an access port in the left atrial appendage wall. As mentioned above, the system may comprise a guide element that may be advanced through the first and/or second access elements. In some variations, the guide element may be coupled to a proximal portion of the piercing element. Catheters, cannulas, or sheaths suitable for intravascular use may also be included. Any of the stabilization and/or left atrial appendage closure devices described above may be included to close the access site, and may additionally or alternatively stabilize the left atrial appendage and/or provide hemostasis of the left atrial appendage.

Also described here are systems for accessing and delivering devices to the heart using an atrial or ventricular wall as a port or access site, in which some variations may be used in conjunction with one or more systems for accessing and delivering devices to the heart using the left atrial appendage as an access site. In general, the systems may comprise a first access element with a first alignment member, a second access element with a second alignment member, and a guide element. First and second access elements may each comprise a longitudinal lumen therethrough. In some variations, some systems may also comprise a piercing element that is configured to pass through the lumen of one access element to the lumen of the other access element and creates an access port in the left atrial appendage wall. The guide element may be advanced through one or more of the access elements to placed the guide element across the access site. In some variations, the guide element may be coupled to a proximal portion of the piercing element. The system may comprise one or more access catheters, such as those described above.

Also described here are systems for closing a left atrial appendage. In general, the systems may comprise a closure device useful for performing a left atrial appendage closure procedure as described above, together with one or more additional components. For example, the system may comprise a first access element having a size and length adapted for accessing the left atrial appendage through the vasculature and comprising an alignment member, a second access element having a size and a length adapted for accessing the pericardial space from a subthoracic region and comprising an alignment member, and a closure and/or stabilization device. The alignment member may be any suitable alignment member. For example, the alignment member may comprise radio-opaque or echogenic markers, members configured to produce an audible response, one or more interconnecting members, one or more vacuum members, or magnets. In some variations, the alignment members of the first and second guides comprise magnets as described above.

The system may further comprise a left atrial appendage occlusion member, where in some variations, the occlusion member is an expandable member or a device. The expandable member may be any suitable expandable member, such as, e.g., the expandable tissue-affecting devices described above. An occlusion member may have one or more apertures therein for allowing contrast or other fluids to pass therethrough.

The systems may also comprise one or more devices for severing the suture. Similarly, the systems may also comprise one or more devices for temporarily straightening one or more curves along the elongate body of the closure device. Of course, the device may comprise instructions for using any, all, or a portion of, the system components (e.g., first guide, second guide, closure device, straightening tube, suture cutter, or some combination thereof).

Some systems may also comprise a cannula or sheath, a first catheter with a first alignment member, a second catheter with a second alignment member, a guide element, and a suture element couple to the guide element. The first and second catheters may be sized and shaped to fit within the cannula. The guide element and suture element may be coupled in an end-to-end fashion, and be pre-loaded into one of the catheters to help expedite and reduce the number of steps needed to create an access port through the LAA.

III. Examples

Several variations of devices and methods for creating an access site or port in the left atrial appendage have been described above. Additionally, devices and methods for creating an access port in an atrial or ventricular wall have been described above. While some examples have been described in the context of accessing and delivering devices to the left atrial appendage, other internal structures of the heart may be accessed. For example, access for additional or alternative devices may be provided through the left atrial appendage by gradually increasing the size of an access site formed in the wall of the left atrial appendage, by a piercing element or wire, as described above. In some variations, the access site may be through a portion of the left atrial appendage. Guide elements may help to guide one or more dilators to the access site. Once the access site is dilated to a sufficient size, devices may be advanced over the guide element into the heart via the left atrial appendage. While some devices that may be delivered to the heart have been described, additional or alternative devices including visualization devices, suturing devices, valve repair devices, ablation devices (e.g., heat, laser, cryogenic, high frequency ultrasound, chemical, etc.), measurement devices, occlusion devices, ligation devices, suction devices, stabilization devices, drug delivery devices (e.g., pumps, permeable membranes, etc.), ventricular assist valves and/or tubes, etc., may also be delivered to the heart. The device may be an implant that remains in the heart after the procedure, or may be a tissue-affecting device that is withdrawn after the desired effect in the tissue has been achieved. Examples of implants that may be used here include replacement valves, occlusion devices, pacemakers, heart monitors, slow-release drug delivery systems, and the like. Tissue-affecting devices that may be delivered to the heart and subsequently removed include ablation elements, measurement devices, closure devices, and the like. In some variations, after a device is delivered to and/or withdrawn from the heart, the left atrial appendage may be closed and/or excluded. In some variations, closure of the left atrial appendage may be a part of the treatment for atrial fibrillation, while in other variations, left atrial appendage closure may be for hemostatic purposes. A variety of treatments for heart diseases may use one or more of the devices and methods described here. Examples of such procedures are described below.

A. Closing a Left Atrial Appendage

A variety of devices may be delivered to the heart using guides and alignment members as described above, for example, devices for the closure and exclusion of the left atrial appendage for the treatment of atrial fibrillation. In such circumstances, it may be desirable for the left atrial appendage to be closed off as close to the anatomical ostial plane as possible. If the left atrial appendage is closed off above the plane of the orifice (toward the left atrial appendage tip or away from the anatomical ostial plane), this may result in a persistent diverticulum of the left atrial appendage, which in turn may result in an additional site or nidus for thrombus formation despite complete exclusion of the left atrial appendage from the left atrium. In some individuals, the geometry of the left atrium and left atrial appendage may be such that the neck or narrowing between them is poorly defined from the epicardial, or outer aspect. In addition, the external geometry of the left atrial appendage-left atrial junction may be difficult to differentiate from an epicardial perspective. This may be compounded by the fact that the anatomy is moving vigorously when the procedures are employed while the heart is beating and the lungs remain inflated (i.e., closed chest procedures). From an inside aspect, or endocardial view, fluoroscopy and ultrasound methods provide limited information or ability to landmark the true three-dimensional characteristics of the anatomic ostial plane. Thus the use of the devices described above may help facilitate proper positioning and closure of the left atrial appendage, and may be used during beating heart procedures.

Figure 9A:
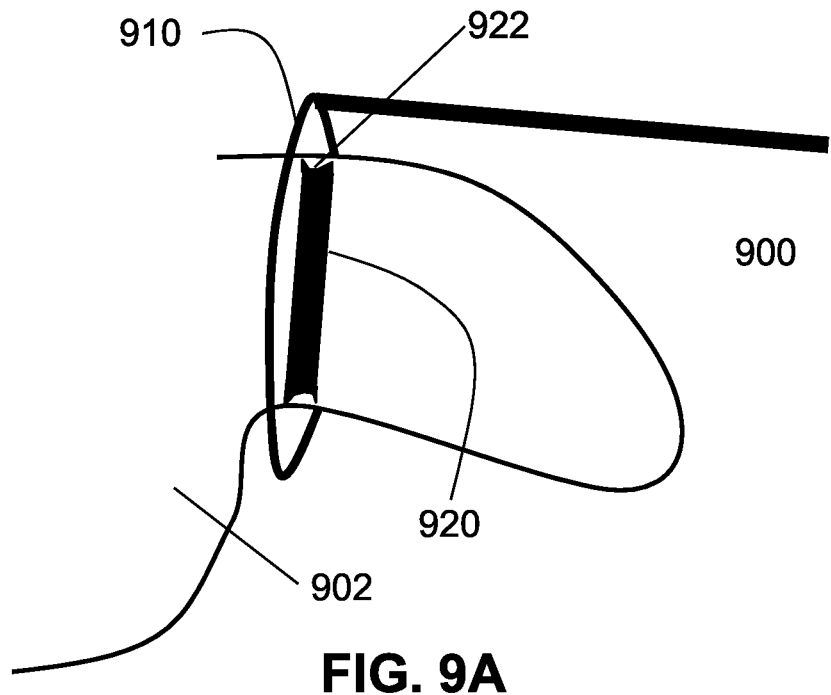
FIGS. 9A and 9B depict one variation of a tissue-affecting device that may be used to position a closure element around a left atrial appendage.
Figure 9B:
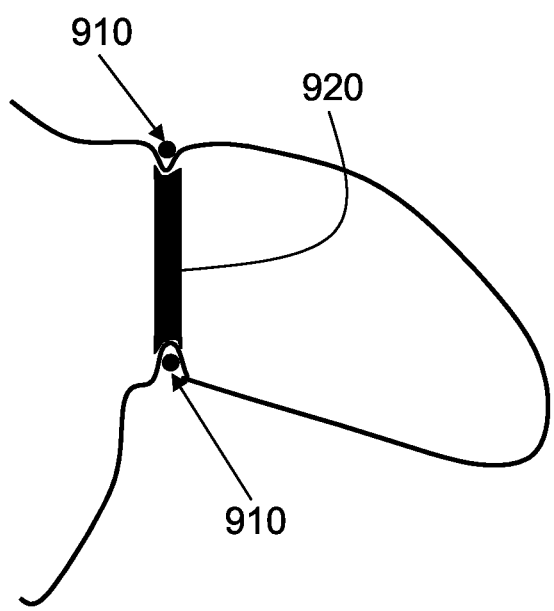

Several examples of devices for closing, occluding, and/or excluding the left atrial appendage have been described above. While FIGS. 8A-8K describe the use of an expandable tissue-affecting device to help position the closure element around the left atrial appendage, other devices may be used to help ensure effective left atrial appendage closure. One variation of a device that may be used to position a closure element is shown in FIGS. 9A and 9B. As shown there, a tissue-affecting device (920) may comprise grooves (922) in its deployed configuration, and is positioned at the anatomical ostium of a left atrial appendage (900). However, the tissue-affecting device (920) may be positioned at any desired location in the heart. In some variations, the tissue-affecting device may be a rounded plate or disc comprising one or more grooves circumscribing the outer perimeter. Grooves (922) are configured to interfit with the closure element (910) as the circumference of the closure element is reduced, as shown in FIG. 9B. The tissue-affecting device (920) may be sized according to the desired degree of closure of the left atrial appendage (900). Once the closure element (910) has been secured and decoupled from the rest of the closure device (e.g., by cutting as described above), the tissue-affecting device (920) may be reverted to its collapsed configuration and withdrawn from the ostium of the left atrial appendage (900). The devices and methods described above for closing and/or excluding the left atrial appendage may be included at the conclusion of a procedure that uses the left atrial appendage as an access site. This may be a more expedient method of closing a heart access site than other conventional methods, such as suture stitching, which may be substantially more time-consuming.

B. Occluding a Left Atrial Appendage

Figure 10A:
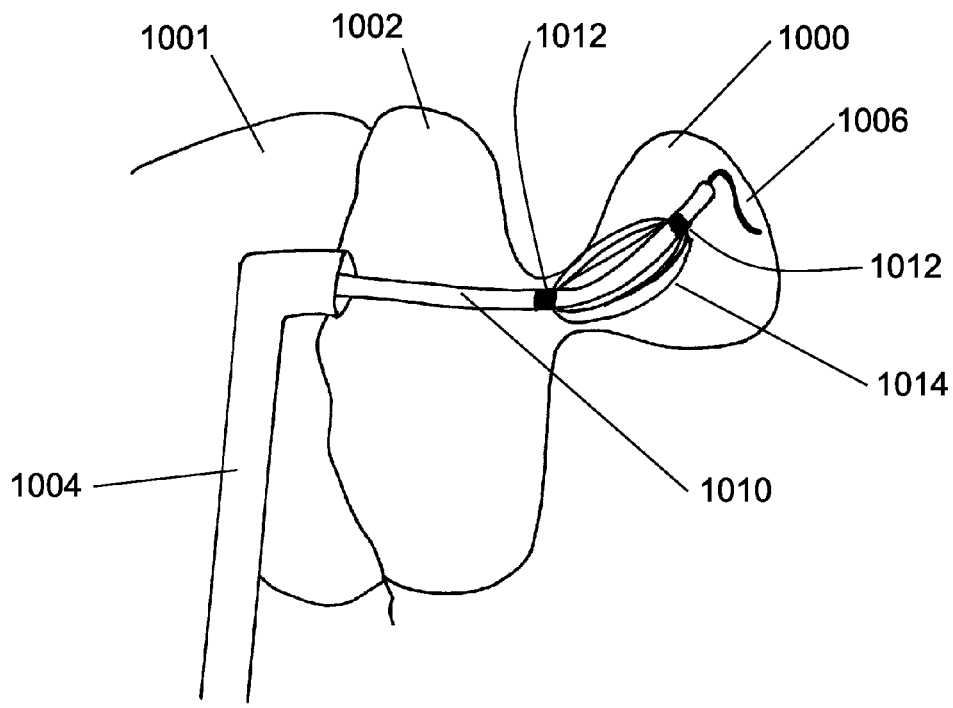
FIGS. 10A-10C depict one example of an implant that may be delivered to an atrial appendage to close, exclude, and/or occlude the atrial appendage.
Figure 10B:
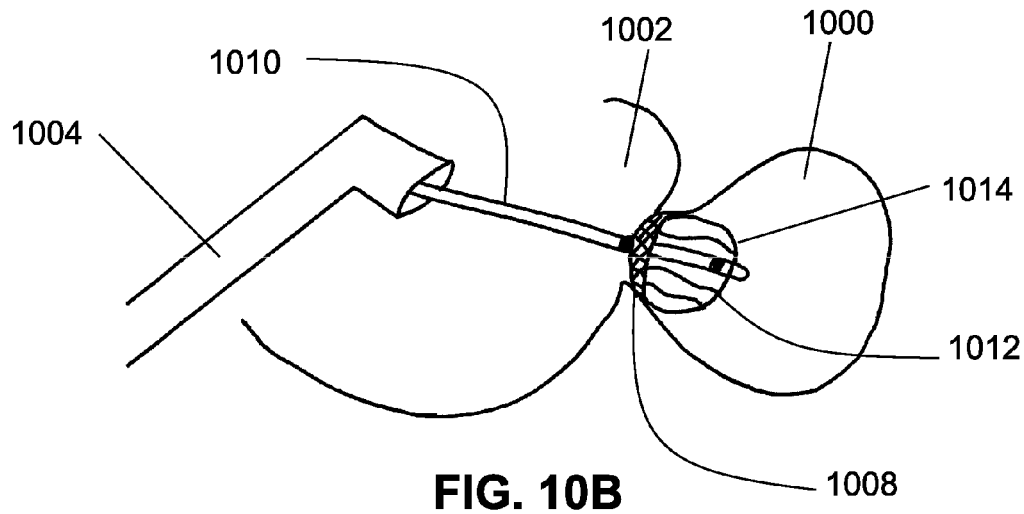
Figure 10C:
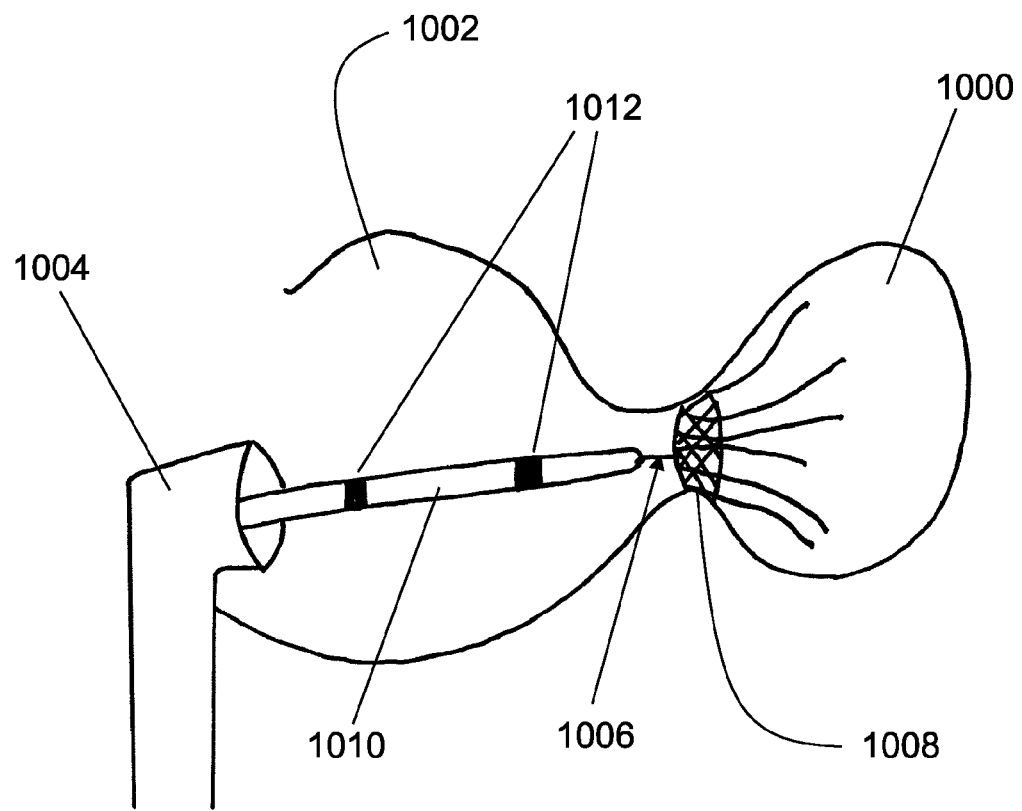

As described above, closure of the left atrial appendage may be attained by encircling the left atrial appendage at the anatomical ostium with a suture loop, and reducing the circumference of the suture loop to close the left atrial appendage. One example of a device that may be advanced to the heart for occluding the left atrial appendage is shown in FIGS. 10A-10C. Devices may be intravascularly delivered to a left atrial appendage (1000) of a heart by entering through the right atrium, crossing the septum to the left atrium (1002) to the left atrial appendage (1000). FIG. 10A depicts a cannula (1004) positioned in the right atrium (1001), against the septum along the right atrium (1002). A catheter (1010) may be advanced over a guide element (1006) through the septum and into the left atrial appendage (1000), where the catheter may be coupled to one or more devices, such as a co-axial expandable member (1014). One or more imaging markers (1012) may be positioned along the catheter (1010), e.g., defining the borders of the expandable member (1014). Imaging markers (1012) may be chosen to permit the desired imaging modality to monitor the position of the catheter (1010) and the expandable member (1014). Once the expandable member (1014) has been confirmed to be in the desired location, it may be expanded to deliver the implantable device (1008). The expandable member (1014) may act to position and/or apposition the implantable device (1008). The implantable device (1008) may be any that effectively closes and/or excludes the left atrial appendage (1000), e.g., a mesh, plug, gel, and the like. FIG. 10C depicts the collapse of the expandable member (1014) after the implantable device (1008) has been positioned, delivered, and deployed. The catheter (1010) may then be retracted over the guide element (1006) into the cannula (1004). The collapsed expandable member may be withdrawn from the left atrial appendage (1000), leaving the implantable device (1008) within the left atrial appendage (1000).

In some variations, a tissue-affecting device may be coupled to the catheter (1010), where after the desired effect has been achieved, the device is then withdrawn. For example, the access pathway as described above may be used to deliver tissue-affecting devices such as ablation devices, suturing devices, excision devices, measurement devices, closure devices, and puncturing devices to the heart. In certain variations, the distal tip of the guide element (1006) may be sharpened and may pierce through the wall of the left atrial appendage. Devices that are external to the heart may be advanced into the heart through the access site created by the guide element. Dilators may be advanced to the access site from a non-vascular pathway to increase the size of the access site for the delivery of additional devices, as described previously.

Figure 11:
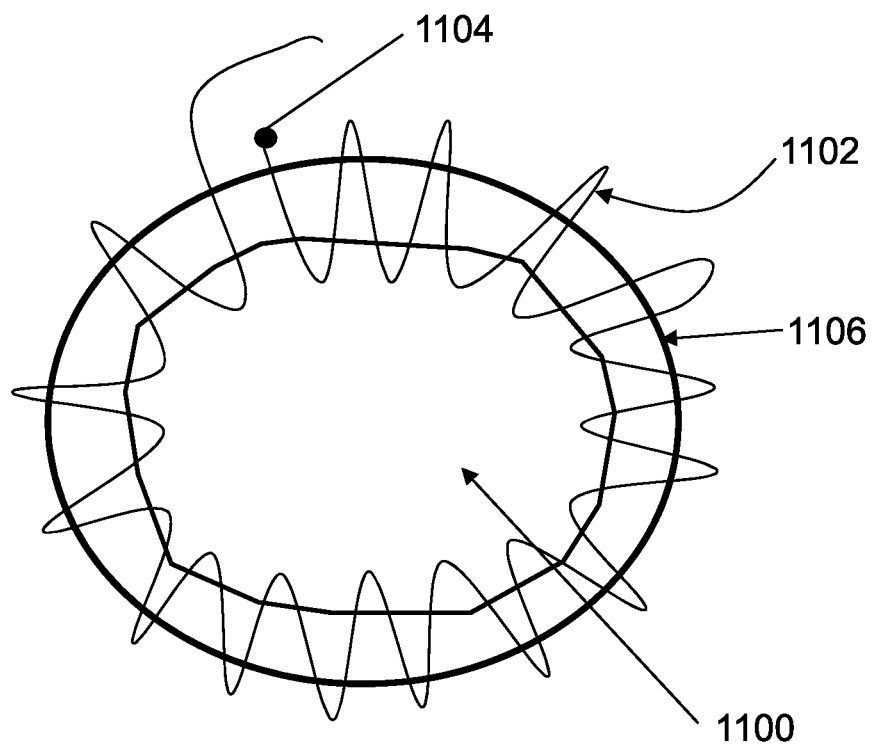
FIG. 11 depicts one variation of a device that may be delivered to a left atrial appendage to close the left atrial appendage by occluding the anatomical ostium.

Another example of a device that may be used with the methods and devices above to close the left atrial appendage is shown in FIG. 11. As shown there, an occlusion device (1100) may be a mesh or other biocompatible sheet that is positioned in the plane of a left atrial appendage ostium (1106). The area of the occlusion device (1100) may be approximately similar to the area of the left atrial appendage ostium (1106). The occlusion device (1100) may be made of any suitable polyermic materials, such as epoxy, chloroprene, polyvinyl chloride, polypropylene, polyimide, and the like. The occlusion device (1100) may be elastic and stretchable. The occlusion device (1100) may be secured in the plane of the left atrial appendage ostium (1106) by a suture (1102), which interlaces between the occlusion device (1100) and tissue around the left atrial appendage ostium (1106) and may be secured by a suture knot (1104). Tensioning the suture (1102) may pull the occlusion device (1100) such that it approximates the shape of the ostium (1106), and may effectively occlude the ostium. Once the desired level of occlusion is attained (which may be confirmed by various imaging methods as previously described), the suture (1102) may be locked by a second knot (not shown).

C. Patent Foramen Ovale

The devices and methods described above may be used in the treatment of a patent foramen ovale or other atrial septal defect. The foramen ovale is a small opening in the wall between the right and left atria that is present in normal fetal development. This opening usually closes within the first or second year of life, however, in at least one out of four people, this opening persists throughout life. Due to this condition, blood may flow between the right and left atria, bypassing the lungs, which may give rise to additional complications such as stroke and/or migraines. Certain treatments for this condition may involve the implantation of devices that seal and/or occlude the patent foramen ovale. Devices for closing the patent foramen ovale may be delivered to the heart via the left atrial appendage and deployed using the methods and devices described above. Examples of implantable devices may include the CardioSEAL® Septal Occlusion devices, STARFlex® devices (NMT Medical Inc, Boston, Mass.) and the Amplatzer® devices (AGA Medical Corp, Golden Valley, Minn.), Helex® devices (GORE Medical Products, Flagstaff, Ariz.), and the like.

Generally, to close or occlude the patent foramen ovale, access to the left atrial appendage may be obtained to form a port or access site across tissue of the left atrial appendage.

Access to the left atrial appendage may be achieved in any suitable manner, such as those described above (e.g., via a pericardial approach, via a combined pericardial and intravascular approach, or the like). In some variations, a device comprising a closure element may be used to stabilize the left atrial appendage and/or help provide hemostasis, as described above. One or more delivery devices containing one or more implants may be advanced to the left atrium via the left atrial appendage access site. In some variations, the delivery device may be advanced over a guidewire placed through the left atrial appendage or through an access catheter or valve placed through the atrial appendage. Additionally, in some variations the delivery devices may advanced across the patent foramen ovale into the right atrium. Once the delivery devices are positioned, the patent foramen ovale may be closed. For example, in some variations, one or more implants may be deployed to seal and/or occlude the foramen. Once appropriate sealing and/or occlusion of the patent foramen ovale has been verified, the access and delivery devices may be withdrawn, and the left atrial appendage may optionally be closed and/or occluded as described above. While described immediately above as being used to close the patent foramen ovale, it should be appreciated that the devices and methods described above may be used to close any suitable atrial septal defect. Additionally, while described above as introducing a delivery device carrying an implant, it should be appreciated that the methods described here may be used to advance any suitable device or devices for closing an atrial septal defect.

Additionally or alternatively, one or more devices for use in closing a patent foramen ovale may be advanced through an access site in the wall of a ventricle or atrium. For example, in some variations, an access site may be formed in the wall of the left ventricle using one or more of the devices or methods described in more detail above, and a guide element or access catheter through the left ventricle access site. One or more devices may be introduced over and/or through the guide element and/or access catheter to introduce the device into the left ventricle. The devices may then be advanced into the left atrium, where it may be used to close or assist in the closure of a patent foramen ovale or other atrial septal defect. In some variations, at least a first device for use in such a closure procedure may be advanced through an access site in the left atrial appendage, while at least a second device for use in such closure may be advanced through an access site in a wall of a ventricle or atrium (e.g., the left ventricle, right ventricle, left atrium, right atrium, etc.).

D. Installation of Cardiac Assist Devices

Congestive heart failure may result in a heart's inability to pump sufficient blood for distribution throughout the body. Depending on the degree to which the pumping capacity of the heart is compromised, cardiac assist devices may be installed. Typically, installation of cardiac assist devices, such as ventricular assist devices, involve connecting inflow and/or outflow tubes between the left ventricle and the aorta. Installation of the flow tubes, and any other peripheral devices such as a flow probes, pumps, etc., may use one or more of the devices and methods described above. For example, access to the exterior of the apex of the left ventricle may be obtained through pericardial access (e.g., using methods described in U.S. Provisional Patent Application Ser. No. 61/323,801, filed on Apr. 13, 2010, and titled "METHODS AND DEVICES FOR PERICARDIAL ACCESS" or U.S. patent application Ser. No. 13/086,328, filed on Apr. 13, 2011, titled "Methods and Devices for Pericardial Access" each of which has been previously incorporated by reference in its entirety), while access to the interior of the left ventricle may be obtained via an access site in the left atrial appendage using the devices and methods described above. Additionally or alternatively, access into the interior of the left ventricle may be obtained via an access site in a wall of the left ventricle and/or a wall of the left atrium. The ability to access multiple locations of the heart may help expedite the installation of cardiac assist devices, and may also help to ensure consistent and precise installment of any peripheral support devices.

E. Implantation of Electrodes

As part of treatment or diagnosis of certain heart conditions, electrodes may be implanted in various locations of the heart. For example, electrodes used in implantable defibrillators may be implanted at multiple locations on the surface of the heart, such as at or near the mid-ventral, mid-dorsal, lateral-apical, lateral-basal left ventricle, etc. Electrodes used for pacemakers may be implanted within the heart, for example, in the right atrium, the right ventricular apex, superior vena cava, etc. The devices and methods described above for accessing the pericardial space of the heart, as well as for accessing various structures within the heart, may be used for implanting electrodes as desired for therapeutic and/or diagnostic purposes.

Generally, access to the left atrial appendage may be obtained to form an access site across tissue of the left atrial appendage. Access to the left atrial appendage may be achieved in any suitable manner, such as those described above (e.g., via a pericardial approach, via a combined pericardial and intravascular approach, or the like). In some variations, a device comprising a closure element may be used to stabilize the left atrial appendage and/or help provide hemostasis, as described above. One or more devices associated with placement or delivery of one or more electrodes may be advanced into the heart through the left atrial appendage. In some variations, one or more electrodes may be advanced into the heart through the left atrial appendage. In other variations, one or more positioning devices may be advanced into the heart through the left atrial appendage, which may help to position an electrode placed inside of the heart. In some variations, the devices may be advanced over a guidewire placed through the left atrial appendage or through an access catheter or valve placed through the atrial appendage. Once in the heart, the electrodes and/or devices may be advanced to any suitable portion of the heart (e.g., the left atrium, right atrium, the right ventricular apex, superior vena cava, etc.) for delivery, placement, and/or removal of one or more electrodes. Once the procedure has been completed, the left atrial appendage may optionally be closed and/or occluded as described above.

Additionally or alternatively, one or more devices for use the placement or delivery of one or more electrodes may be advanced through an access site in the wall of a ventricle or atrium. For example, in some variations, an access site may be formed in the wall of the left ventricle using one or more of the devices or methods described in more detail above, and a guide element or access catheter through the left ventricle access site. One or more devices may be introduced over and/or through the guide element and/or access catheter to introduce the device into the left ventricle. In some variations, at least a first device for placement, visualization, and/or delivery of an electrode may be advanced into the heart through an access site in the left atrial appendage, while at least a second device for placement, visualization, and/or delivery of an electrode may be advanced into the heart through an access site in a wall of a ventricle or atrium (e.g., the left ventricle, right ventricle, left atrium, right atrium, etc.).

F. Valve Repair or Remodelling

Heart valve disorders, such as valvular stenosis, valvular regurgitation, congenital valve disease, mitral valve prolapse, etc., may be treated by remodeling or replacing the defective valve. Access to the mitral valve from the atrial side, for example, may be obtained through the left atrial appendage as described above, where devices for valve remodeling and/or replacement may be delivered through the left atrial appendage. In some valve repair procedures, it may be appropriate to introduce a guide element intravascularly into the left ventricle as described above to provide additional assistance to devices introduced to the left atrium. For example, access to both the ventricular and atrial side of a mitral valve may be useful for valve remodeling procedures that involve stitching sutures around the valve. Guide elements with alignment members may help to ensure proper positioning of suturing and other remodeling devices.

Valve replacement or remodeling procedures may also use one or more of the devices described above. For example, the replacement valve may be introduced from the pericardial space into the heart via an access site in the left atrial appendage. After the replacement valve has been installed, the left atrial appendage may be excluded, closed, and/or occluded to seal the access site. Similarly, the left atrial appendage access site may be used to advance an annuloplasty band or ring (or one or more devices configured to place, adjust, or remove an annuloplasty band or ring) into the heart, using any of the methods described above. Additionally or alternatively, one or more implants or devices associated with chordae tendineae replacement may be advanced through a left atrial appendage access site to assist in a chordinae tendineae replacement procedure. Once the procedure has been completed, the devices may be withdrawn, and the left atrial appendage may optionally be closed and/or occluded as described above.

Additionally or alternatively, one or more devices for use the placement or delivery of one or more electrodes may be advanced through an access site in the wall of a ventricle or atrium. For example, in some variations, an access site may be formed in the wall of the left ventricle using one or more of the devices or methods described in more detail above, and a guide element or access catheter through the left ventricle access site. One or more devices may be introduced over and/or through the guide element and/or access catheter to introduce the device into the left ventricle. In some variations, at least a first device for use in one of the previously mentioned procedures may be advanced into the heart through an access site in the left atrial appendage, while at least a second device for use in one of the previously-mentioned procedures may be advanced into the heart through the left ventricle access site. For example, in some variations, a replacement valve may be advanced into the heart through a left atrial appendage access site, while one or more suture devices may be advanced into the heart through a left ventricle access site.

G. Ablation

As part of treatment or diagnosis of certain heart conditions, one or more portions of the heart may be ablated. For example, methods of ablating or otherwise forming lesions in heart tissue are described in U.S. Provisional Patent Application No. 61/323,796, filed on Apr. 13, 2010 and titled "METHODS AND DEVICES FOR TREATING ATRIAL FIBRILLATION, and U.S. patent application Ser. No. 13/086,389, filed on Apr. 13, 2011, titled "Methods and Devices for Treating Atrial Fibrillation", each of which has been previously incorporated by reference in its entirety. In some methods, it may be desirable to place one or more ablation or lesion-forming devices on the interior of the heart. Accordingly, a left atrial appendage access site may be useful for placing one or more ablation devices.

Generally, access to the left atrial appendage may be obtained to form an access site across tissue of the left atrial appendage. Access to the left atrial appendage may be achieved in any suitable manner, such as those described above (e.g., via a pericardial approach, via a combined pericardial and intravascular approach, or the like). In some variations, a device comprising a closure element may be used to stabilize the left atrial appendage and/or help provide hemostasis, as described above. One or more ablation devices (or devices associated with the placement and/or alignment of ablation devices) may be advanced into the heart through the left atrial appendage. In some variations, the device or devices may be advanced over a guidewire placed through the left atrial appendage or through an access catheter or valve placed through the atrial appendage. Once in the heart, the device or devices may be advanced to any suitable portion of the heart (e.g., the left atrium, right atrium, the right ventricular apex, superior vena cava, etc.) or surrounding vasculature (e.g., left pulmonary veins, right pulmonary veins, or the like), and one or more ablation procedures may be performed using the device or devices. Once the procedure has been completed, the device or devices may be removed and the left atrial appendage may optionally be closed and/or occluded as described above. Additionally or alternatively, one or more ablation devices (or devices associated with the placement and/or alignment of ablation devices) may be advanced into the heart through an access site in a ventricular or atrial wall using one or more of the devices and methods described above.

Although the foregoing invention has, for the purposes of clarity and understanding been described in some detail by way of illustration and example, it will be apparent that certain changes and modifications may be practiced, and are intended to fall within the scope of the appended claims.

What is claimed is:

1. A method for cardiac valve treatment via a left atrial appendage, the method comprising:

advancing a first guide intravascularly to an interior of the left atrial appendage, wherein the first guide comprises a first longitudinal lumen therethrough and a first magnet;

advancing a second guide through the pericardium to an exterior of the left atrial appendage, wherein the second guide comprises a second longitudinal lumen therethrough and a second magnet;

aligning the first and second guides using the first and second magnets such that the first longitudinal lumen is aligned with the second longitudinal lumen and homeostasis is maintained between the magnets;

advancing a piercing element through the left atrial appendage through the first and second longitudinal lumens to access a cardiac valve site;

advancing a guide element through the first and second longitudinal lumens;

advancing a treatment device along the guide element into the heart through the left atrial appendage to the cardiac valve site;

repairing or replacing the cardiac valve with the treatment device;

removing the treatment device through the left atrial appendage; and advancing a closure device to the left atrial appendage; and closing the left atrial appendage with the closure device.

2. The method of claim 1 wherein the treatment device comprises a cardiac valve repair device.

3. The method of claim 2 wherein the valve repair device comprises an annuloplasty band or ring.

4. The method of claim 2 wherein the valve repair device comprises a chordae tendinae replacement device.

5. The method of claim 1 wherein the treatment device comprises a cardiac valve replacement device.

6. The method of claim 1, further comprising advancing a suture device into the heart through a left ventricle access site.

7. The method of claim 1 wherein the cardiac valve is a mitral valve.

8. The method of claim 1 wherein the cardiac valve is a tricuspid valve.

9. The method of claim 1 wherein the cardiac valve is a semilunar valve.

10. The method of claim 1 wherein closing the left atrial appendage comprises ligating the left atrial appendage with a suture loop.

11. The method of claim 1 wherein closing the left atrial appendage comprises occluding the left atrial appendage with an expandable member.

12. The method of claim 1 wherein the closure device comprises a closure element forming a loop and a suture loop.

13. The method of claim 12 wherein the suture loop is releasably connected to the closure element.

14. The method of claim 1 further comprising advancing a guide element intravascularly into the left ventricle to assist in cardiac valve treatment.

15. The method of claim 1 further comprising stabilizing the left atrial appendage with the closure device before the repairing step.

16. The method of claim 15 wherein the closure device comprises a closure element forming a loop and a suture loop, and wherein stabilizing the left atrial appendage with the closure device comprises closing the closure element around the left atrial appendage to help maintain homeostasis.

17. The method of claim 16 further comprising reopening the closure element to allow the treatment device to advance therethrough and reclosing the closure element around the treatment device to help maintain homeostasis.

18. The method of claim 1 wherein a clamp connects the piercing element and the guide element.

19. The method of claim 1 further comprising expanding a balloon in the left atrial appendage to assist in closing the left atrial appendage near an ostium of the left atrial appendage.

20. The method of claim 1 wherein the first and second guides are aligned linearly end-to-end.

* * * * *